US008771424B2

(12) United States Patent
Quanz

(10) Patent No.: US 8,771,424 B2
(45) Date of Patent: Jul. 8, 2014

(54) METHOD FOR THE PRODUCING ALPHA-1, 6-BRANCHED ALPHA-1, 4-GLUCANS FROM SUCROSE

(75) Inventor: Martin Quanz, Berlin (DE)

(73) Assignees: Bayer Bioscience GmbH, Potsdam (DE); Max-Planck-Gesellschaft zur Foderung der Wissenchaften E.V., Berlin (DE)

( * ) Notice: Subject to any disclaimer, the term of this patent is extended or adjusted under 35 U.S.C. 154(b) by 220 days.

(21) Appl. No.: 13/194,719

(22) Filed: Jul. 29, 2011

(65) Prior Publication Data

US 2012/0046458 A1 Feb. 23, 2012

Related U.S. Application Data

(62) Division of application No. 12/905,894, filed on Oct. 15, 2010, now abandoned, which is a division of application No. 11/781,226, filed on Jul. 20, 2007, now Pat. No. 7,833,751, which is a division of application No. 10/705,195, filed on Nov. 10, 2003, now Pat. No. 7,732,164, which is a division of application No. 09/807,063, filed as application No. PCT/EP99/07562 on Oct. 8, 1999, now Pat. No. 6,699,694.

(30) Foreign Application Priority Data

Oct. 9, 1998 (DE) .................................. 198 46 635
May 27, 1999 (DE) .................................. 199 24 342

(51) Int. Cl.
*C08B 30/00* (2006.01)
*C08B 30/02* (2006.01)
*A23L 1/0522* (2006.01)
*C12N 15/82* (2006.01)

(52) U.S. Cl.
USPC ............ 127/32; 127/65; 800/278; 435/320.1; 435/468

(58) Field of Classification Search
None
See application file for complete search history.

(56) References Cited

U.S. PATENT DOCUMENTS

| | | | |
|---|---|---|---|
| 4,454,161 A | 6/1984 | Okada et al. | |
| 5,648,111 A * | 7/1997 | Pearlstein et al. | 426/578 |
| 6,265,635 B1 | 7/2001 | Kossmann et al. | |
| 6,323,265 B1 | 11/2001 | Bengs et al. | |
| 6,566,585 B1 | 5/2003 | Quanz | |
| 6,699,694 B1 | 3/2004 | Buttcher et al. | |
| 7,638,311 B2 | 12/2009 | Buttcher et al. | |
| 2008/0020427 A1 | 1/2008 | Buttcher et al. | |
| 2008/0020432 A1 | 1/2008 | Buttcher et al. | |

FOREIGN PATENT DOCUMENTS

| | | |
|---|---|---|
| DE | 4447388 A1 | 6/1996 |
| EP | 0690170 A1 | 3/1996 |
| EP | 418945 A1 | 3/1997 |
| WO | WO9531553 | 11/1995 |
| WO | WO 9716554 | 5/1997 |
| WO | WO 9844780 A1 | 10/1998 |

OTHER PUBLICATIONS

Birhed et al., Archives of Oral Biology, vol. 24, No. 1, pp. 63-66 (1979).
Lloyd, James R et al., "Simultaneous antisense inhibition . . . ", Biochemical Society, (1999)338, 515-521.
Rumbak, Elaine et al., "Characterization of the . . . ", Journal of Bacteriology, Nov. 1991, vol. 173, No. 21, 6732-6741.
Parodi, Armando J. et al., "In vitro synthesis . . . ", Archives of Biochemistry and Biophysics, 132, (1969), 111-117.
Shewmaker, Christine K. et al., "Expression of *Escherichia coli* glycpgen . . . ", Plant Physiol., (1994) 104, 1159-1166.
Kortstee, Anne J. et al., "Expression of *Escherichia coli* branching . . . ", The Plant Journal, (1996) 10(1), 83-90.
Krisman, Clara R. et al., "Branching enzyme assay . . . ", Analytical Biochemistry, (1985), 147, 491-496.
Doi, Akemi, "ADP-D-Glucose: . . . ," Biochim. Biophys. Acta, 184 (1969), 477-485.
Boyer, Charles et al., "Biosynthesis of bacterial . . . ," Biochemistry, vol. 16, No. 16, (1997), 3693-3699.
Nakamura, Yasunori et al., "Nucleotide sequence of a cDNA . . . ," Plant Physiol., (1992) 99, 1265-1266.
Fiedler, G. et al., "Genetics of a novel . . . ," J. Mol. Biol., (1996) 265, 279-291.
Fiedlerr, G. et al., "Genetics of a novel (sequence listing)," Medline, http://ars.ebi.ac.uk/srs6bin/wgetz?-id+lg4c51GmNut+- e+[EMBL:'KOCYMSCGT], 1-7.
Kormann, Jens et al., "Cloning and expression . . . ," Mol Gen Genet, (1991) 230, 34-44.
Okada, Gentaro et al., "New studies on amylosucrase . . . ," Journal of Biological Chemistry, No. 1, (Jan. 10, 1974), 126-135.
Illingsworth, Barbara et al., "The de novo . . . ," Proc. N.A.S., vol. 47, 1961, 469-478.
Dov Borovsky, Eric E. et al., "Purification and properties . . . ," Eur. J. Biochem., (1975) 59, 615-625.
Baba, Tadashi et al., "Sequence conservation of . . . ," Biochemical and Biophysical Research Communications, Nov. 27, 1991, vol. 181, No. 1, 87-94.
Baeker, Preston A. et al., "Biosynthesis of bacterial . . . ," The Journal of Biological Chemistry, Jul. 5, 1996, vol. 261, No. 19, 8739-8743.
Kiel, J.A.K.W. et al., "Cloning and expression of the branching . . . ," Gene, 78, (1989) 9-17.
Jacobsen, E. et al., "Phenotypic and genotypic . . . ," Euphytica, (1989) 44, 43-48.
Mackenzie, C.R. et al., "Glycogen metabolism in the genus . . . ," Can. J. Microbiol., vol. 24, (1978), 357-362.

(Continued)

*Primary Examiner* — Brent T Page
(74) *Attorney, Agent, or Firm* — Birch, Stewart, Kolasch & Birch, LLP

(57) ABSTRACT

Nucleic acid molecules which encode a branching enzyme from a bacterium of the genus *Neisseria*, vectors, host cell, plant cells and plants containing said nucleic acid molecules as well as starch obtainable from the plants described are described. Furthermore, an in-vitro method for producing α-1,6-branched α-1,4-glucans on the basis of sucrose and a combination of enzymes of an amylosucrase and a branching enzyme as well as the α-1,6-branched α-1,4-glucans obtainable by said method are described.

4 Claims, 20 Drawing Sheets

(56) References Cited

OTHER PUBLICATIONS

Mackenzie, C.R. et al., "Glycogen synthesis by amylosucrase . . . ," Can. J. Microbiol., (1977) vol. 23, 1303-1307.
Riou, Jean-Yves et al., "Structure of the exocellular . . . ," Can. J. Microbiol., (1986) vol. 32, 909-911.
Hovenkamp-Hermelink, J.H.M. et al., "Rapid estimation of the amylase . . . ", Potato Research (1988)31, 241-246.
Buttcher, Volker et al., "Cloning and Characterization . . . ," Journal of Bacteriology, (May 1977) vol. 179, No. 10, 3324-3330.
Brown, B.I. et al., "α-1, 4-Glucan: α-1, 4-Glucan . . . ," Methods of Enzymology, 8(1966, pp. 395-403.
Doi A. Enzymatic Synthesis of Amylopectin Type Polysaccharide in a Two Enzyme System, Biochimia et Biophysics Acta 186 1969, 477-485.
Buttcher V. Cloning and Characterization of the Gene for Amylosucrase from *Neisseria polsaccharea*. J of Bacteriology May 1997, 179(10) 3324-30.
Buttcher V. Molecular Cloning, Functional Expression and Purification of a Glucan Branching Enzyme from *Neisseria denitrificans*. Biochimica et Biophysica Acta 1432(2) 406-412, 1999.
Tomasky, Diana Silva et al., "The degree of branching in (α1,4)-(α1,6)-linked . . . ," Eur. J. Biochem., 1987, 168, pp. 393-398.
Tetlow et al 2004, Journal of Experimental Botany 55(406):2131-2145, pp. 2131 and 2135.
Van Geel-Schutten, G.H. et al., "Biochemical and Structural Characterizations . . . ," Appl. Environ. Microbiol. (1999) vol. 65, No. 7, 3008-3014.
Kirby, "Non-Food Uses of Starch", Alexander and Zobel (Ed.), Developments in Carbohydrate Chemistry, Held During the Annual Meeting of the American Association of Cereal Chemists, 1992, XP009083324, pp. 371-386.
Chica, et al., Curr Opin Biotechnol, (2005), vol. 16(4), pp. 378-384.
Office Action dated Jun. 10, 2008 in copending U.S. Appl. No. 11/781,222.
Office Action dated Jun. 26, 2009 in copending U.S. Appl. No. 11/781,222.
Office Action dated Mar. 27, 2008 in copending U.S. Appl. No. 11/781,228.
Office Action dated May 30, 2008 in copending U.S. Appl. No. 11/781,228.
Office Action dated Dec. 15, 2008 in copending U.S. Appl. No. 11/781,228.
Office Action dated Jun. 8, 2006 in copending U.S. Appl. No. 10/705,195.
Office Action dated Oct. 19, 2006 in copending U.S. Appl. No. 10/705,195.
Office Action dated Apr. 9, 2007 in copending U.S. Appl. No. 10/705,195.
Office Action dated Oct. 10, 2007 in copending U.S. Appl. No. 10/705,195.
Office Action dated Jul. 23, 2008 in copending U.S. Appl. No. 10/705,195.
Office Action dated Jan. 28, 2009 in copending U.S. Appl. No. 10/705,195.
Office Action dated Jun. 5, 2009 in copending U.S. Appl. No. 10/705,195.
Kossmann, J. et al., "Starch Biosynthesis and Modification of Starch Structure in Transgenic Plants", Macromolecular Symposia, vol. 120, Issue 1, pp. 29-38, 1997.

\* cited by examiner

SEQUENCE LISTING

```
<160> NUMBER OF SEQ ID NOS: 34

<210> SEQ ID NO 1
<211> LENGTH: 2475
<212> TYPE: DNA
<213> ORGANISM: Neisseria denitrificans
<220> FEATURE:
<221> NAME/KEY: CDS
<222> LOCATION: (170)..(2458)

<400> SEQUENCE: 1
actgtatgcc gtgcagctgg aaaacctgct gggcgtacgc gacaacctca atattcccgg      60
cgtggccgaa ggctatccga actgggcgcg caaaatgccg cagcctctgg aagcctttgc     120
ccgccacccg caaatgggca agcagcttgc catgatggga gacatccgc atg aac cga    178
                                                     Met Asn Arg
                                                       1 aac cgc cat atc cga cgc ggc tac cac ccg gaa gcc gga gaa cgc caa      226
Asn Arg His Ile Arg Arg Gly Tyr His Pro Glu Ala Gly Glu Arg Gln
         5                  10                  15 atc atc gac agc ctg ttt gcc gcc acc cac agc gat ccg ttt gcc tat      274
Ile Ile Asp Ser Leu Phe Ala Ala Thr His Ser Asp Pro Phe Ala Tyr
 20                  25                  30                  35 ctt ggg cgg cat cgt gtc aac gac gaa cgc gaa gcc gtg cgc gtg ctg      322
Leu Gly Arg His Arg Val Asn Asp Glu Arg Glu Ala Val Arg Val Leu
             40                  45                  50 cgt ccc gac gcg cac cac atc gac atc atc gac cgc cac aca ggc gca      370
Arg Pro Asp Ala His His Ile Asp Ile Ile Asp Arg His Thr Gly Ala
         55                  60                  65 gtc atc atg ccg tct gaa aaa atc gac gag cgc ggc ctg ttt gcc gcc      418
Val Ile Met Pro Ser Glu Lys Ile Asp Glu Arg Gly Leu Phe Ala Ala
     70                  75                  80 gta ttg ccc gaa cac gcg ccc gac tac gcc ctg ctg gtg aca tac cac      466
Val Leu Pro Glu His Ala Pro Asp Tyr Ala Leu Leu Val Thr Tyr His
 85                  90                  95 gag ggc gaa gcc gcc gta cgc gaa gaa gat gac tac cgc ttc ggc agc      514
Glu Gly Glu Ala Ala Val Arg Glu Glu Asp Asp Tyr Arg Phe Gly Ser
100                 105                 110                 115 gcg ctg caa cat acc gat gcc tgg ctg ctg ggc gaa ggc acg cac ctg      562
Ala Leu Gln His Thr Asp Ala Trp Leu Leu Gly Glu Gly Thr His Leu
            120                 125                 130 cgc cct tat gaa acg ctg ggc gca cat ttc gcc gaa atg gac ggc gta      610
Arg Pro Tyr Glu Thr Leu Gly Ala His Phe Ala Glu Met Asp Gly Val
        135                 140                 145 tcc ggc gtg cgc ttt gcc gtt tgg gcg ccc aac gcg cgg gta tcg          658
Ser Gly Val Arg Phe Ala Val Trp Ala Pro Asn Ala Arg Arg Val Ser
```

-continued

```
            150                 155                 160
gtc atc ggc gaa ttc aac ggc tgg gac agc cgc cgc cat gcc atg cgt    706
Val Ile Gly Glu Phe Asn Gly Trp Asp Ser Arg Arg His Ala Met Arg
    165                 170                 175 ccg cac aca ggc aac ggc ctg tgg gac atc ttt atc ccc ggc gtc ggc    754
Pro His Thr Gly Asn Gly Leu Trp Asp Ile Phe Ile Pro Gly Val Gly
180                 185                 190                 195 ctc aac gcg ctg tat aaa ttc tcc gta ctc gat gcc aac ggc aac atc    802
Leu Asn Ala Leu Tyr Lys Phe Ser Val Leu Asp Ala Asn Gly Asn Ile
            200                 205                 210 cgc gaa aaa gcc gac ccc tac gca ttc ggc gcg gag ctg cgc ccg acc    850
Arg Glu Lys Ala Asp Pro Tyr Ala Phe Gly Ala Glu Leu Arg Pro Thr
            215                 220                 225 acc gca tcc gtg gtg cgc ggc ttg ccg gcc aaa gcc gaa gcg ccc gct    898
Thr Ala Ser Val Val Arg Gly Leu Pro Ala Lys Ala Glu Ala Pro Ala
        230                 235                 240 ttc cgc cgc cgc gcc aac tcc gtg gaa gcg ccc atc agc att tac gaa    946
Phe Arg Arg Arg Ala Asn Ser Val Glu Ala Pro Ile Ser Ile Tyr Glu
    245                 250                 255 gtc cat ctc ggc tcg tgg cgg cgc aat ccc gaa aac aac tac tgg ctc    994
Val His Leu Gly Ser Trp Arg Arg Asn Pro Glu Asn Asn Tyr Trp Leu
260                 265                 270                 275 acc tac acg cag ctg gcc gac gaa ttg gtg aac tat gta aaa gac atg    1042
Thr Tyr Thr Gln Leu Ala Asp Glu Leu Val Asn Tyr Val Lys Asp Met
            280                 285                 290 ggc ttc acc cac atc gag ctg ctg ccc ttg tcc gaa tat ccg ttc gac    1090
Gly Phe Thr His Ile Glu Leu Leu Pro Leu Ser Glu Tyr Pro Phe Asp
            295                 300                 305 ggc tca tgg ggc tac caa gcc acc ggc ctg tat gca ccg acc agc cgc    1138
Gly Ser Trp Gly Tyr Gln Ala Thr Gly Leu Tyr Ala Pro Thr Ser Arg
        310                 315                 320 ttc ggc tcg ccc gat gag ctg aaa gcc ctg att gac gcc gcc cac gcc    1186
Phe Gly Ser Pro Asp Glu Leu Lys Ala Leu Ile Asp Ala Ala His Ala
    325                 330                 335 gcc ggc atc agc gtg att ctc gac tgg gta gcg ggg cac ttc ccc acc    1234
Ala Gly Ile Ser Val Ile Leu Asp Trp Val Ala Gly His Phe Pro Thr
340                 345                 350                 355 gac gac cac ggc ctc aac acc ttc gac ggc acg gcg ctt tac gaa cac    1282
Asp Asp His Gly Leu Asn Thr Phe Asp Gly Thr Ala Leu Tyr Glu His
            360                 365                 370 gcc gac ccg cgc gaa ggc tac cat cag gat tgg aac acg ctg att tac    1330
Ala Asp Pro Arg Glu Gly Tyr His Gln Asp Trp Asn Thr Leu Ile Tyr
            375                 380                 385 aac ttc ggc cgc aac gaa gtc aaa aac ttc ctg cag ggc aac gcg ctc    1378
Asn Phe Gly Arg Asn Glu Val Lys Asn Phe Leu Gln Gly Asn Ala Leu
        390                 395                 400 tac tgg att gag cgt ttc ggc ttc gac ggc atc cgc gtg gac gcc gtg    1426
Tyr Trp Ile Glu Arg Phe Gly Phe Asp Gly Ile Arg Val Asp Ala Val
    405                 410                 415 gcc tcg atg att tac cgc aac tac tcg cgc aaa gac ggc gag tgg att    1474
Ala Ser Met Ile Tyr Arg Asn Tyr Ser Arg Lys Asp Gly Glu Trp Ile
420                 425                 430                 435 ccc aac cgc tac ggc ggc agc gaa aat ctg gaa gcc atc gcc ttt ttg    1522
Pro Asn Arg Tyr Gly Gly Ser Glu Asn Leu Glu Ala Ile Ala Phe Leu
            440                 445                 450 cgc caa acc aat gcc gtc tta aaa agc gaa aca ccc ggc gcc ggc tcg    1570
Arg Gln Thr Asn Ala Val Leu Lys Ser Glu Thr Pro Gly Ala Gly Ser
            455                 460                 465 ttt gcc gaa gaa tcg act tcc ttt gcc gac gta acc cgc gaa gcc ggc    1618
```

```
                Phe Ala Glu Glu Ser Thr Ser Phe Ala Asp Val Thr Arg Glu Ala Gly
                                470                 475                 480 ctg aac ttc gat ttc aaa tgg aat atg ggc tgg atg aac gac acc ctg             1666
Leu Asn Phe Asp Phe Lys Trp Asn Met Gly Trp Met Asn Asp Thr Leu
485                 490                 495 cgc tat atg cag gaa gac ccc gtc cac cgc aaa tac cac cac ggc aaa             1714
Arg Tyr Met Gln Glu Asp Pro Val His Arg Lys Tyr His His Gly Lys
500                 505                 510                 515 atg aca ttc ggc atg atg tac caa tac agc gaa aac ttc gtt ctg ccc             1762
Met Thr Phe Gly Met Met Tyr Gln Tyr Ser Glu Asn Phe Val Leu Pro
                520                 525                 530 ctg tcg cac gac gaa gtg gta cac ggc aaa cgc tcg ctg ctg ggc aaa             1810
Leu Ser His Asp Glu Val Val His Gly Lys Arg Ser Leu Leu Gly Lys
                535                 540                 545 atg ccg ggc gac tgc tgg cag cag ttt gcc aac ctg cgc gcc tat tac             1858
Met Pro Gly Asp Cys Trp Gln Gln Phe Ala Asn Leu Arg Ala Tyr Tyr
                550                 555                 560 ggc ttt atg tac ggc ttc ccc ggc aaa aaa ctc cta ttt atg ggc aac             1906
Gly Phe Met Tyr Gly Phe Pro Gly Lys Lys Leu Leu Phe Met Gly Asn
565                 570                 575 gaa ttt gcc caa ggc cgc gag tgg aat tat cag gaa gga ctg gat tgg             1954
Glu Phe Ala Gln Gly Arg Glu Trp Asn Tyr Gln Glu Gly Leu Asp Trp
580                 585                 590                 595 cat ctg ctc gac gaa gcg ggc ggc tgg cac aaa ggc gtg cag gat tat             2002
His Leu Leu Asp Glu Ala Gly Gly Trp His Lys Gly Val Gln Asp Tyr
                600                 605                 610 gta cgc gac ctg aac cac atc tac acc gcc cac gcc ccg ctc tac cag             2050
Val Arg Asp Leu Asn His Ile Tyr Thr Ala His Ala Pro Leu Tyr Gln
                615                 620                 625 ctc gac cag cag ccc gag ggc ttt gaa tgg ctg gtg gcc gac gac agc             2098
Leu Asp Gln Gln Pro Glu Gly Phe Glu Trp Leu Val Ala Asp Asp Ser
630                 635                 640 gac aat tcg gta ttc gta ttc gag cgc cgc gac cgc gca ggc aac cgc             2146
Asp Asn Ser Val Phe Val Phe Glu Arg Arg Asp Arg Ala Gly Asn Arg
645                 650                 655 atc atc gtc atc agc aac ttt acc ccg gtg gtg cgc gaa cac tac cgc             2194
Ile Ile Val Ile Ser Asn Phe Thr Pro Val Val Arg Glu His Tyr Arg
660                 665                 670                 675 ttc ggc gtc aac gcg ccc ggc cgc tat acc gaa atc ctg aat tcc gac             2242
Phe Gly Val Asn Ala Pro Gly Arg Tyr Thr Glu Ile Leu Asn Ser Asp
                680                 685                 690 cgc acg cag tat caa ggc agc ggc atc gca aac ggc gcg gac atc acg             2290
Arg Thr Gln Tyr Gln Gly Ser Gly Ile Ala Asn Gly Ala Asp Ile Thr
                695                 700                 705 gcg gaa aac gtg cct tcg cac ggc aaa gcg cag tcg ctg agc ctg acc             2338
Ala Glu Asn Val Pro Ser His Gly Lys Ala Gln Ser Leu Ser Leu Thr
                710                 715                 720 ctg ccg ccg ctg gcc acg gtc tat ctg tat cag aaa gcc gcg ccc gca             2386
Leu Pro Pro Leu Ala Thr Val Tyr Leu Tyr Gln Lys Ala Ala Pro Ala
725                 730                 735 acg gaa att cag acg gcc ttg cgc gcc gac aag cag ccg gcg gta aaa             2434
Thr Glu Ile Gln Thr Ala Leu Arg Ala Asp Lys Gln Pro Ala Val Lys
740                 745                 750                 755 gat aag cag gca aaa gcc aaa taa agcggcacca tactgcc                          2475
Asp Lys Gln Ala Lys Ala Lys
                760

<210> SEQ ID NO 2
<211> LENGTH: 762
<212> TYPE: PRT
```

<213> ORGANISM: Neisseria denitrificans

<400> SEQUENCE: 2

Met Asn Arg Asn Arg His Ile Arg Arg Gly Tyr His Pro Glu Ala Gly
1               5                   10                  15

Glu Arg Gln Ile Ile Asp Ser Leu Phe Ala Ala Thr His Ser Asp Pro
            20                  25                  30

Phe Ala Tyr Leu Gly Arg His Arg Val Asn Asp Glu Arg Glu Ala Val
        35                  40                  45

Arg Val Leu Arg Pro Asp Ala His His Ile Asp Ile Asp Arg His
    50                  55                  60

Thr Gly Ala Val Ile Met Pro Ser Glu Lys Ile Asp Glu Arg Gly Leu
65                  70                  75                  80

Phe Ala Ala Val Leu Pro Glu His Ala Pro Asp Tyr Ala Leu Leu Val
                85                  90                  95

Thr Tyr His Glu Gly Glu Ala Ala Val Arg Glu Glu Asp Asp Tyr Arg
            100                 105                 110

Phe Gly Ser Ala Leu Gln His Thr Asp Ala Trp Leu Leu Gly Glu Gly
        115                 120                 125

Thr His Leu Arg Pro Tyr Glu Thr Leu Gly Ala His Phe Ala Glu Met
130                 135                 140

Asp Gly Val Ser Gly Val Arg Phe Ala Val Trp Ala Pro Asn Ala Arg
145                 150                 155                 160

Arg Val Ser Val Ile Gly Glu Phe Asn Gly Trp Asp Ser Arg Arg His
                165                 170                 175

Ala Met Arg Pro His Thr Gly Asn Gly Leu Trp Asp Ile Phe Ile Pro
            180                 185                 190

Gly Val Gly Leu Asn Ala Leu Tyr Lys Phe Ser Val Leu Asp Ala Asn
        195                 200                 205

Gly Asn Ile Arg Glu Lys Ala Asp Pro Tyr Ala Phe Gly Ala Glu Leu
    210                 215                 220

Arg Pro Thr Thr Ala Ser Val Val Arg Gly Leu Pro Ala Lys Ala Glu
225                 230                 235                 240

Ala Pro Ala Phe Arg Arg Ala Asn Ser Val Glu Ala Pro Ile Ser
                245                 250                 255

Ile Tyr Glu Val His Leu Gly Ser Trp Arg Arg Asn Pro Glu Asn Asn
            260                 265                 270

Tyr Trp Leu Thr Tyr Thr Gln Leu Ala Asp Glu Leu Val Asn Tyr Val
        275                 280                 285

Lys Asp Met Gly Phe Thr His Ile Glu Leu Leu Pro Leu Ser Glu Tyr
    290                 295                 300

Pro Phe Asp Gly Ser Trp Gly Tyr Gln Ala Thr Gly Leu Tyr Ala Pro
305                 310                 315                 320

Thr Ser Arg Phe Gly Ser Pro Asp Glu Leu Lys Ala Leu Ile Asp Ala
                325                 330                 335

Ala His Ala Ala Gly Ile Ser Val Ile Leu Asp Trp Val Ala Gly His
            340                 345                 350

Phe Pro Thr Asp Asp His Gly Leu Asn Thr Phe Asp Gly Thr Ala Leu
        355                 360                 365

Tyr Glu His Ala Asp Pro Arg Glu Gly Tyr His Gln Asp Trp Asn Thr
    370                 375                 380

Leu Ile Tyr Asn Phe Gly Arg Asn Glu Val Lys Asn Phe Leu Gln Gly
385                 390                 395                 400

```
Asn Ala Leu Tyr Trp Ile Glu Arg Phe Gly Phe Asp Gly Ile Arg Val
                405                 410                 415
Asp Ala Val Ala Ser Met Ile Tyr Arg Asn Tyr Ser Arg Lys Asp Gly
            420                 425                 430
Glu Trp Ile Pro Asn Arg Tyr Gly Gly Ser Glu Asn Leu Glu Ala Ile
        435                 440                 445
Ala Phe Leu Arg Gln Thr Asn Ala Val Leu Lys Ser Glu Thr Pro Gly
    450                 455                 460
Ala Gly Ser Phe Ala Glu Ser Thr Ser Phe Ala Asp Val Thr Arg
465                 470                 475                 480
Glu Ala Gly Leu Asn Phe Asp Phe Lys Trp Asn Met Gly Trp Met Asn
                485                 490                 495
Asp Thr Leu Arg Tyr Met Gln Glu Asp Pro Val His Arg Lys Tyr His
            500                 505                 510
His Gly Lys Met Thr Phe Gly Met Met Tyr Gln Tyr Ser Glu Asn Phe
        515                 520                 525
Val Leu Pro Leu Ser His Asp Glu Val Val His Gly Lys Arg Ser Leu
    530                 535                 540
Leu Gly Lys Met Pro Gly Asp Cys Trp Gln Gln Phe Ala Asn Leu Arg
545                 550                 555                 560
Ala Tyr Tyr Gly Phe Met Tyr Gly Phe Pro Gly Lys Lys Leu Leu Phe
                565                 570                 575
Met Gly Asn Glu Phe Ala Gln Gly Arg Glu Trp Asn Tyr Gln Glu Gly
            580                 585                 590
Leu Asp Trp His Leu Leu Asp Glu Ala Gly Gly Trp His Lys Gly Val
        595                 600                 605
Gln Asp Tyr Val Arg Asp Leu Asn His Ile Tyr Thr Ala His Ala Pro
    610                 615                 620
Leu Tyr Gln Leu Asp Gln Gln Pro Glu Gly Phe Glu Trp Leu Val Ala
625                 630                 635                 640
Asp Asp Ser Asp Asn Ser Val Phe Val Phe Glu Arg Arg Asp Arg Ala
                645                 650                 655
Gly Asn Arg Ile Ile Val Ile Ser Asn Phe Thr Pro Val Val Arg Glu
            660                 665                 670
His Tyr Arg Phe Gly Val Asn Ala Pro Gly Arg Tyr Thr Glu Ile Leu
        675                 680                 685
Asn Ser Asp Arg Thr Gln Tyr Gln Gly Ser Gly Ile Ala Asn Gly Ala
    690                 695                 700
Asp Ile Thr Ala Glu Asn Val Pro Ser His Gly Lys Ala Gln Ser Leu
705                 710                 715                 720
Ser Leu Thr Leu Pro Pro Leu Ala Thr Val Tyr Leu Tyr Gln Lys Ala
                725                 730                 735
Ala Pro Ala Thr Glu Ile Gln Thr Ala Leu Arg Ala Asp Lys Gln Pro
            740                 745                 750
Ala Val Lys Asp Lys Gln Ala Lys Ala Lys
        755                 760

<210> SEQ ID NO 3
<211> LENGTH: 6
<212> TYPE: PRT
<213> ORGANISM: Neisseria denitrificans
<220> FEATURE:
<221> NAME/KEY: UNSURE
<222> LOCATION: (5)..(5)
<223> OTHER INFORMATION: Xaa = any amino acid, unknown or other
```

<400> SEQUENCE: 3

Met Asn Arg Asn Xaa His
 1               5

<210> SEQ ID NO 4
<211> LENGTH: 2914
<212> TYPE: DNA
<213> ORGANISM: Neisseria polysaccharea
<220> FEATURE:
<221> NAME/KEY: CDS
<222> LOCATION: (957)..(2867)

<400> SEQUENCE: 4

| | |
|---|---|
| gagttttgcg ttcccgaacc gaacgtgatg cttgagccga acacctgtcc ggcaaggcgg | 60 |
| ctgaccgccc ccttttgccc catcgacatc gtaacaatcg gtttggtggc aagctctttc | 120 |
| gctttgagcg tggcagaaag caaagtcagc acgtcttccg cgctttgcgg catcaccgca | 180 |
| attttgcaga tgtccgcgcc gcagtcctcc atctgtttca gacggcatac gatttcttct | 240 |
| tgcggcggcg tgcggtgaaa ctcatgattg cagagcaggg cggcgatgcc gttttttga | 300 |
| gcatgcgcca cggcgcgccg gacggcggtt tcgccggaaa aaagctcgat atcgataatg | 360 |
| tcgggcaggc ggctttcaat cagcgagtcg agcagttcaa ataataatc gtccgaacac | 420 |
| gggaacgagc cgccttcgcc atgccgtctg aacgtaaaca gcagcggctt gtcgggcagc | 480 |
| gcgtcgcgga cggtctgcgt gtggcgcaat acttcgccga tgctgcccgc gcattccaaa | 540 |
| aaatcggcgc ggaactcgac gatatcgaag gcaggttttt tgatttggtc aagtacggcg | 600 |
| gaaagtacgg cggcatcgcg ggcgacaagc ggcacgcga ttttggtgcg tccgcttccg | 660 |
| ataacggtgt ttttgacggt caggctggtg tgcatggcgg ttgttgcggc tgaaaggaac | 720 |
| ggtaaagacg caattatagc aaaggcacag gcaatgtttc agacggcatt tctgtgcggc | 780 |
| cggcttgata tgaatcaagc agcatccgca tatcggaatg cagacttggc acaagccctg | 840 |
| tcttttctag tcagtccgca gttcttgcag tatgattgca cgacacgccc tacacggcat | 900 |
| ttgcaggata cggcggcaga ccgccggtcg gaaacttcag aatcggagca ggcatc atg | 959 |
| | Met |
| | 1 |

| | |
|---|---|
| ttg acc ccc acg cag caa gtc ggt ttg att tta cag tac ctc aaa aca | 1007 |
| Leu Thr Pro Thr Gln Gln Val Gly Leu Ile Leu Gln Tyr Leu Lys Thr | |
|      5                  10                  15 | |

| | |
|---|---|
| cgc atc ttg gac atc tac acg ccc gaa cag cgc gcc ggc atc gaa aaa | 1055 |
| Arg Ile Leu Asp Ile Tyr Thr Pro Glu Gln Arg Ala Gly Ile Glu Lys | |
|          20                  25                  30 | |

| | |
|---|---|
| tcc gaa gac tgg cgg cag ttt tcg cgc cgc atg gat acg cat ttc ccc | 1103 |
| Ser Glu Asp Trp Arg Gln Phe Ser Arg Arg Met Asp Thr His Phe Pro | |
|  35                  40                  45 | |

| | |
|---|---|
| aaa ctg atg aac gaa ctc gac agc gtg tac ggc aac aac gaa gcc ctg | 1151 |
| Lys Leu Met Asn Glu Leu Asp Ser Val Tyr Gly Asn Asn Glu Ala Leu | |
| 50                  55                  60                  65 | |

| | |
|---|---|
| ctg cct atg ctg gaa atg ctg ctg gcg cag gca tgg caa agc tat tcc | 1199 |
| Leu Pro Met Leu Glu Met Leu Leu Ala Gln Ala Trp Gln Ser Tyr Ser | |
|              70                  75                  80 | |

| | |
|---|---|
| caa cgc aac tca tcc tta aaa gat atc gat atc gcg cgc gaa aac aac | 1247 |
| Gln Arg Asn Ser Ser Leu Lys Asp Ile Asp Ile Ala Arg Glu Asn Asn | |
|              85                  90                  95 | |

| | |
|---|---|
| ccc gat tgg att ttg tcc aac aaa caa gtc ggc ggc gtg tgc tac gtt | 1295 |
| Pro Asp Trp Ile Leu Ser Asn Lys Gln Val Gly Gly Val Cys Tyr Val | |
|         100                 105                 110 | |

| | |
|---|---|
| gat ttg ttt gcc ggc gat ttg aag ggc ttg aaa gat aaa att cct tat | 1343 |

```
                Asp Leu Phe Ala Gly Asp Leu Lys Gly Leu Lys Asp Lys Ile Pro Tyr
                    115                 120                 125 ttt caa gag ctt ggt ttg act tat ctg cac ctg atg ccg ctg ttt aaa       1391
Phe Gln Glu Leu Gly Leu Thr Tyr Leu His Leu Met Pro Leu Phe Lys
130                 135                 140                 145 tgc cct gaa ggc aaa agc gac ggc ggt tat gcg gtc agc agc tac cgc       1439
Cys Pro Glu Gly Lys Ser Asp Gly Gly Tyr Ala Val Ser Ser Tyr Arg
                150                 155                 160 gat gtc aat ccg gca ctg ggc aca ata ggc gac ttg cgc gaa gtc att       1487
Asp Val Asn Pro Ala Leu Gly Thr Ile Gly Asp Leu Arg Glu Val Ile
            165                 170                 175 gct gcg ctg cac gaa gcc ggc att tcc gcc gtc gtc gat ttt atc ttc       1535
Ala Ala Leu His Glu Ala Gly Ile Ser Ala Val Val Asp Phe Ile Phe
        180                 185                 190 aac cac acc tcc aac gaa cac gaa tgg gcg caa cgc tgc gcc gcc ggc       1583
Asn His Thr Ser Asn Glu His Glu Trp Ala Gln Arg Cys Ala Ala Gly
    195                 200                 205 gac ccg ctt ttc gac aat ttc tac tat att ttc ccc gac cgc cgg atg       1631
Asp Pro Leu Phe Asp Asn Phe Tyr Tyr Ile Phe Pro Asp Arg Arg Met
210                 215                 220                 225 ccc gac caa tac gac cgc acc ctg cgc gaa atc ttc ccc gac cag cac       1679
Pro Asp Gln Tyr Asp Arg Thr Leu Arg Glu Ile Phe Pro Asp Gln His
                230                 235                 240 ccg ggc ggc ttc tcg caa ctg gaa gac gga cgc tgg gtg tgg acg acc       1727
Pro Gly Gly Phe Ser Gln Leu Glu Asp Gly Arg Trp Val Trp Thr Thr
                245                 250                 255 ttc aat tcc ttc caa tgg gac ttg aat tac agc aac ccg tgg gta ttc       1775
Phe Asn Ser Phe Gln Trp Asp Leu Asn Tyr Ser Asn Pro Trp Val Phe
            260                 265                 270 cgc gca atg gcg ggc gaa atg ctg ttc ctt gcc aac ttg ggc gtt gac       1823
Arg Ala Met Ala Gly Glu Met Leu Phe Leu Ala Asn Leu Gly Val Asp
        275                 280                 285 atc ctg cgt atg gat gcg gtt gcc ttt att tgg aaa caa atg ggg aca       1871
Ile Leu Arg Met Asp Ala Val Ala Phe Ile Trp Lys Gln Met Gly Thr
    290                 295                 300                 305 agc tgc gaa aac ctg ccg cag gcg cac gcc ctc atc cgc gcg ttc aat       1919
Ser Cys Glu Asn Leu Pro Gln Ala His Ala Leu Ile Arg Ala Phe Asn
                310                 315                 320 gcc gtt atg cgt att gcc gcg ccc gcc gtg ttc ttc aaa tcc gaa gcc       1967
Ala Val Met Arg Ile Ala Ala Pro Ala Val Phe Phe Lys Ser Glu Ala
                325                 330                 335 atc gtc cac ccc gac caa gtc gtc caa tac atc ggg cag gac gaa tgc       2015
Ile Val His Pro Asp Gln Val Val Gln Tyr Ile Gly Gln Asp Glu Cys
            340                 345                 350 caa atc ggt tac aac ccc ctg caa atg gca ttg ttg tgg aac acc ctt       2063
Gln Ile Gly Tyr Asn Pro Leu Gln Met Ala Leu Leu Trp Asn Thr Leu
355                 360                 365 gcc acg cgc gaa gtc aac ctg ctc cat cag gcg ctg acc tac cgc cac       2111
Ala Thr Arg Glu Val Asn Leu Leu His Gln Ala Leu Thr Tyr Arg His
370                 375                 380                 385 aac ctg ccc gag cat acc gcc tgg gtc aac tac gtc cgc agc cac gac       2159
Asn Leu Pro Glu His Thr Ala Trp Val Asn Tyr Val Arg Ser His Asp
                390                 395                 400 gac atc ggc tgg acg ttt gcc gat gaa gac gcg gca tat ctg ggc ata       2207
Asp Ile Gly Trp Thr Phe Ala Asp Glu Asp Ala Ala Tyr Leu Gly Ile
                405                 410                 415 agc ggc tac gac cac cgc caa ttc ctc aac cgc ttc ttc gtc aac cgt       2255
Ser Gly Tyr Asp His Arg Gln Phe Leu Asn Arg Phe Phe Val Asn Arg
            420                 425                 430
```

-continued

| | | |
|---|---|---|
| ttc gac ggc agc ttc gct cgt ggc gta ccg ttc caa tac aac cca agc<br>Phe Asp Gly Ser Phe Ala Arg Gly Val Pro Phe Gln Tyr Asn Pro Ser<br>435                      440                        445 | | 2303 |
| aca ggc gac tgc cgt gtc agt ggt aca gcc gcg gca ttg gtc ggc ttg<br>Thr Gly Asp Cys Arg Val Ser Gly Thr Ala Ala Ala Leu Val Gly Leu<br>450                      455                    460                        465 | | 2351 |
| gcg caa gac gat ccc cac gcc gtt gac cgc atc aaa ctc ttg tac agc<br>Ala Gln Asp Asp Pro His Ala Val Asp Arg Ile Lys Leu Leu Tyr Ser<br>                    470                        475                    480 | | 2399 |
| att gct ttg agt acc ggc ggt ctg ccg ctg att tac cta ggc gac gaa<br>Ile Ala Leu Ser Thr Gly Gly Leu Pro Leu Ile Tyr Leu Gly Asp Glu<br>485                      490                    495 | | 2447 |
| gtg ggt acg ctc aat gac gac gac tgg tcg caa gac agc aat aag agc<br>Val Gly Thr Leu Asn Asp Asp Asp Trp Ser Gln Asp Ser Asn Lys Ser<br>                  500                    505                    510 | | 2495 |
| gac gac agc cgt tgg gcg cac cgt ccg cgc tac aac gaa gcc ctg tac<br>Asp Asp Ser Arg Trp Ala His Arg Pro Arg Tyr Asn Glu Ala Leu Tyr<br>515                      520                    525 | | 2543 |
| gcg caa cgc aac gat ccg tcg acc gca gcc ggg caa atc tat cag ggc<br>Ala Gln Arg Asn Asp Pro Ser Thr Ala Ala Gly Gln Ile Tyr Gln Gly<br>530                      535                    540                    545 | | 2591 |
| ttg cgc cat atg att gcc gtc cgc caa agc aat ccg cgc ttc gac ggc<br>Leu Arg His Met Ile Ala Val Arg Gln Ser Asn Pro Arg Phe Asp Gly<br>                  550                    555                    560 | | 2639 |
| ggc agg ctg gtt aca ttc aac acc aac aac aag cac atc atc ggc tac<br>Gly Arg Leu Val Thr Phe Asn Thr Asn Asn Lys His Ile Ile Gly Tyr<br>565                      570                    575 | | 2687 |
| atc cgc aac aat gcg ctt ttg gca ttc ggt aac ttc agc gaa tat ccg<br>Ile Arg Asn Asn Ala Leu Leu Ala Phe Gly Asn Phe Ser Glu Tyr Pro<br>580                      585                    590 | | 2735 |
| caa acc gtt acc gcg cat acc ctg caa gcc atg ccc ttc aag gcg cac<br>Gln Thr Val Thr Ala His Thr Leu Gln Ala Met Pro Phe Lys Ala His<br>595                      600                    605 | | 2783 |
| gac ctc atc ggt ggc aaa act gtc agc ctg aat cag gat ttg acg ctt<br>Asp Leu Ile Gly Gly Lys Thr Val Ser Leu Asn Gln Asp Leu Thr Leu<br>610                      615                    620                    625 | | 2831 |
| cag ccc tat cag gtc atg tgg ctc gaa atc gcc tga cgcacgcttc<br>Gln Pro Tyr Gln Val Met Trp Leu Glu Ile Ala<br>                  630                    635 | | 2877 |
| ccaaatgccg tctgaaccgt ttcagacggc atttgcg | | 2914 |

<210> SEQ ID NO 5
<211> LENGTH: 636
<212> TYPE: PRT
<213> ORGANISM: Neisseria polysaccharea

<400> SEQUENCE: 5

Met Leu Thr Pro Thr Gln Gln Val Gly Leu Ile Leu Gln Tyr Leu Lys
1                   5                   10                  15

Thr Arg Ile Leu Asp Ile Tyr Thr Pro Glu Gln Arg Ala Gly Ile Glu
                20                   25                   30

Lys Ser Glu Asp Trp Arg Gln Phe Ser Arg Arg Met Asp Thr His Phe
              35                   40                   45

Pro Lys Leu Met Asn Glu Leu Asp Ser Val Tyr Gly Asn Asn Glu Ala
        50                   55                   60

Leu Leu Pro Met Leu Glu Met Leu Leu Ala Gln Ala Trp Gln Ser Tyr
65                   70                   75                  80

Ser Gln Arg Asn Ser Ser Leu Lys Asp Ile Asp Ile Ala Arg Glu Asn
                    85                   90                   95

```
Asn Pro Asp Trp Ile Leu Ser Asn Lys Gln Val Gly Val Cys Tyr
            100                 105                 110
Val Asp Leu Phe Ala Gly Asp Leu Lys Gly Leu Lys Asp Lys Ile Pro
115             120                 125
Tyr Phe Gln Glu Leu Gly Leu Thr Tyr Leu His Leu Met Pro Leu Phe
            130                 135                 140
Lys Cys Pro Glu Gly Lys Ser Asp Gly Gly Tyr Ala Val Ser Ser Tyr
145             150                 155                 160
Arg Asp Val Asn Pro Ala Leu Gly Thr Ile Gly Asp Leu Arg Glu Val
            165                 170                 175
Ile Ala Ala Leu His Glu Ala Gly Ile Ser Ala Val Val Asp Phe Ile
            180                 185                 190
Phe Asn His Thr Ser Asn Glu His Glu Trp Ala Gln Arg Cys Ala Ala
            195                 200                 205
Gly Asp Pro Leu Phe Asp Asn Phe Tyr Tyr Ile Phe Pro Asp Arg Arg
            210                 215                 220
Met Pro Asp Gln Tyr Asp Arg Thr Leu Arg Glu Ile Phe Pro Asp Gln
225             230                 235                 240
His Pro Gly Gly Phe Ser Gln Leu Glu Asp Gly Arg Trp Val Trp Thr
            245                 250                 255
Thr Phe Asn Ser Phe Gln Trp Asp Leu Asn Tyr Ser Asn Pro Trp Val
            260                 265                 270
Phe Arg Ala Met Ala Gly Glu Met Leu Phe Leu Ala Asn Leu Gly Val
            275                 280                 285
Asp Ile Leu Arg Met Asp Ala Val Ala Phe Ile Trp Lys Gln Met Gly
            290                 295                 300
Thr Ser Cys Glu Asn Leu Pro Gln Ala His Ala Leu Ile Arg Ala Phe
305             310                 315                 320
Asn Ala Val Met Arg Ile Ala Ala Pro Ala Val Phe Phe Lys Ser Glu
            325                 330                 335
Ala Ile Val His Pro Asp Gln Val Val Gln Tyr Ile Gly Gln Asp Glu
            340                 345                 350
Cys Gln Ile Gly Tyr Asn Pro Leu Gln Met Ala Leu Leu Trp Asn Thr
            355                 360                 365
Leu Ala Thr Arg Glu Val Asn Leu Leu His Gln Ala Leu Thr Tyr Arg
            370                 375                 380
His Asn Leu Pro Glu His Thr Ala Trp Val Asn Tyr Val Arg Ser His
385             390                 395                 400
Asp Asp Ile Gly Trp Thr Phe Ala Asp Glu Ala Ala Tyr Leu Gly
            405                 410                 415
Ile Ser Gly Tyr Asp His Arg Gln Phe Leu Asn Arg Phe Phe Val Asn
            420                 425                 430
Arg Phe Asp Gly Ser Phe Ala Arg Gly Val Pro Phe Gln Tyr Asn Pro
            435                 440                 445
Ser Thr Gly Asp Cys Arg Val Ser Gly Thr Ala Ala Ala Leu Val Gly
            450                 455                 460
Leu Ala Gln Asp Asp Pro His Ala Val Asp Arg Ile Lys Leu Leu Tyr
465             470                 475                 480
Ser Ile Ala Leu Ser Thr Gly Gly Leu Pro Leu Ile Tyr Leu Gly Asp
            485                 490                 495
Glu Val Gly Thr Leu Asn Asp Asp Asp Trp Ser Gln Asp Ser Asn Lys
            500                 505                 510
```

-continued

Ser Asp Asp Ser Arg Trp Ala His Arg Pro Arg Tyr Asn Glu Ala Leu
            515                 520                 525

Tyr Ala Gln Arg Asn Asp Pro Ser Thr Ala Ala Gly Gln Ile Tyr Gln
        530                 535                 540

Gly Leu Arg His Met Ile Ala Val Arg Gln Ser Asn Pro Arg Phe Asp
545                 550                 555                 560

Gly Gly Arg Leu Val Thr Phe Asn Thr Asn Lys His Ile Ile Gly
                565                 570                 575

Tyr Ile Arg Asn Asn Ala Leu Leu Ala Phe Gly Asn Phe Ser Glu Tyr
            580                 585                 590

Pro Gln Thr Val Thr Ala His Thr Leu Gln Ala Met Pro Phe Lys Ala
        595                 600                 605

His Asp Leu Ile Gly Gly Lys Thr Val Ser Leu Asn Gln Asp Leu Thr
610                 615                 620

Leu Gln Pro Tyr Gln Val Met Trp Leu Glu Ile Ala
625                 630                 635

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: artificial
      sequence

<400> SEQUENCE: 6
gtcgacatga accgaaaccg ccatatc                                         27

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: artificial
      sequence

<400> SEQUENCE: 7
cctgcaggta tggtgccgct ttatttggc                                       29

<210> SEQ ID NO 8
<211> LENGTH: 7
<212> TYPE: PRT
<213> ORGANISM: Neisseria denitrificans

<400> SEQUENCE: 8

Met Asn Arg Asn Arg His Ile
1               5

<210> SEQ ID NO 9
<211> LENGTH: 6
<212> TYPE: PRT
<213> ORGANISM: Neisseria denitrificans

<400> SEQUENCE: 9

Arg Pro Asp Ala His His
1               5

<210> SEQ ID NO 10
<211> LENGTH: 7
<212> TYPE: PRT
<213> ORGANISM: Neisseria denitrificans

<400> SEQUENCE: 10

His Ala Pro Asp Tyr Ala Leu
1               5

<210> SEQ ID NO 11
<211> LENGTH: 5
<212> TYPE: PRT
<213> ORGANISM: Neisseria denitrificans

<400> SEQUENCE: 11

Glu Gly Glu Ala Ala
1               5

<210> SEQ ID NO 12
<211> LENGTH: 5
<212> TYPE: PRT
<213> ORGANISM: Neisseria denitrificans

<400> SEQUENCE: 12

Asp Asp Tyr Arg Phe
1               5

<210> SEQ ID NO 13
<211> LENGTH: 5
<212> TYPE: PRT
<213> ORGANISM: Neisseria denitrificans

<400> SEQUENCE: 13

Ser Ala Leu Gln His
1               5

<210> SEQ ID NO 14
<211> LENGTH: 5
<212> TYPE: PRT
<213> ORGANISM: Neisseria denitrificans

<400> SEQUENCE: 14

Tyr Glu Thr Leu Gly
1               5

<210> SEQ ID NO 15
<211> LENGTH: 5
<212> TYPE: PRT
<213> ORGANISM: Neisseria denitrificans

<400> SEQUENCE: 15

Val Ser Gly Val Arg
1               5

<210> SEQ ID NO 16
<211> LENGTH: 5
<212> TYPE: PRT
<213> ORGANISM: Neisseria denitrificans

<400> SEQUENCE: 16

Val Ser Val Ile Gly
1               5

<210> SEQ ID NO 17
<211> LENGTH: 5
<212> TYPE: PRT
<213> ORGANISM: Neisseria denitrificans

<400> SEQUENCE: 17

Phe Asn Gly Trp Asp

```
                  1               5

<210> SEQ ID NO 18
<211> LENGTH: 5
<212> TYPE: PRT
<213> ORGANISM: Neisseria denitrificans

<400> SEQUENCE: 18

Leu Tyr Lys Phe Ser
  1               5

<210> SEQ ID NO 19
<211> LENGTH: 5
<212> TYPE: PRT
<213> ORGANISM: Neisseria denitrificans

<400> SEQUENCE: 19

Pro Tyr Ala Phe Gly
  1               5

<210> SEQ ID NO 20
<211> LENGTH: 6
<212> TYPE: PRT
<213> ORGANISM: Neisseria denitrificans

<400> SEQUENCE: 20

Arg Pro Thr Thr Ala Ser
  1               5

<210> SEQ ID NO 21
<211> LENGTH: 5
<212> TYPE: PRT
<213> ORGANISM: Neisseria denitrificans

<400> SEQUENCE: 21

Phe Arg Arg Arg Ala
  1               5

<210> SEQ ID NO 22
<211> LENGTH: 6
<212> TYPE: PRT
<213> ORGANISM: Neisseria denitrificans

<400> SEQUENCE: 22

Asp Glu Leu Val Asn Tyr
  1               5

<210> SEQ ID NO 23
<211> LENGTH: 6
<212> TYPE: PRT
<213> ORGANISM: Neisseria denitrificans

<400> SEQUENCE: 23

Leu Pro Leu Ser Glu Tyr
  1               5

<210> SEQ ID NO 24
<211> LENGTH: 6
<212> TYPE: PRT
<213> ORGANISM: Neisseria denitrificans

<400> SEQUENCE: 24

Tyr Gln Ala Thr Gly Leu
  1               5
```

```
<210> SEQ ID NO 25
<211> LENGTH: 5
<212> TYPE: PRT
<213> ORGANISM: Neisseria denitrificans

<400> SEQUENCE: 25

Asp Asp His Gly Leu
 1               5

<210> SEQ ID NO 26
<211> LENGTH: 5
<212> TYPE: PRT
<213> ORGANISM: Neisseria denitrificans

<400> SEQUENCE: 26

His Gln Asp Trp Asn
 1               5

<210> SEQ ID NO 27
<211> LENGTH: 5
<212> TYPE: PRT
<213> ORGANISM: Neisseria denitrificans

<400> SEQUENCE: 27

Asp Gly Ile Arg Val
 1               5

<210> SEQ ID NO 28
<211> LENGTH: 6
<212> TYPE: PRT
<213> ORGANISM: Neisseria denitrificans

<400> SEQUENCE: 28

Tyr Gly Gly Ser Glu Asn
 1               5

<210> SEQ ID NO 29
<211> LENGTH: 6
<212> TYPE: PRT
<213> ORGANISM: Neisseria denitrificans

<400> SEQUENCE: 29

Ser Phe Ala Glu Glu Ser
 1               5

<210> SEQ ID NO 30
<211> LENGTH: 5
<212> TYPE: PRT
<213> ORGANISM: Neisseria denitrificans

<400> SEQUENCE: 30

Asp Pro Val His Arg
 1               5

<210> SEQ ID NO 31
<211> LENGTH: 6
<212> TYPE: PRT
<213> ORGANISM: Neisseria denitrificans

<400> SEQUENCE: 31

Trp Gln Gln Phe Ala Asn
 1               5

<210> SEQ ID NO 32
```

```
<211> LENGTH: 5
<212> TYPE: PRT
<213> ORGANISM: Neisseria denitrificans

<400> SEQUENCE: 32

Glu Ile Leu Asn Ser
 1               5

<210> SEQ ID NO 33
<211> LENGTH: 8
<212> TYPE: PRT
<213> ORGANISM: Neisseria denitrificans

<400> SEQUENCE: 33

Ala Thr Glu Ile Gln Thr Ala Leu
 1               5

<210> SEQ ID NO 34
<211> LENGTH: 9
<212> TYPE: PRT
<213> ORGANISM: Neisseria denitrificans

<400> SEQUENCE: 34

Val Lys Asp Lys Gln Ala Lys Ala Lys
 1               5
```

METHOD FOR THE PRODUCING ALPHA-1, 6-BRANCHED ALPHA-1, 4-GLUCANS FROM SUCROSE

This application is a Divisional of co-pending U.S. application Ser. No. 12/905,894 filed on Oct. 15, 2010, which is a Divisional of U.S. application Ser. No. 11/781,226 filed on Jul. 20, 2007 and now issued as U.S. Pat. No. 7,833,751, which is a Divisional of U.S. Ser. No. 10/705,195 filed Nov. 10, 2003 and now issued as U.S. Pat. No. 7,732,164, which is a Divisional of U.S. application Ser. No. 09/807,063, filed on Jun. 11, 2001 and now issued as U.S. Pat. No. 6,699,694 B1 which is a national phase under 35 U.S.C. §371 of PCT International Application No. PCT/EP99/07562 which has an International filing date of Oct. 8, 1999, which designated the United States and on which priority is claimed under 35 U.S.C. §120, the entire contents of which are hereby incorporated by reference. This divisional application claims priority under 35 U.S.C. §119 on Application No. 198 46 635.8 filed in Germany on Oct. 9, 1998 and Application No. 199 24 342.5 filed in Germany on May 27, 1999, the entire contents of which are hereby incorporated by reference.

The present invention relates to nucleic acid molecules encoding a branching enzyme from bacteria of the genus *Neisseria*, vectors, host cells, plant cells and plants containing such nucleic acid molecules as well as starch obtainable from the plants described. Furthermore, the present invention relates to in-vitro methods for the production of α-1,6-branched α-1,4-glucans on the basis of sucrose and a combination of enzymes of an amylosucrase and a branching enzyme. Moreover, the invention relates to glucans that are obtainable by the method described.

In many respects, α-1,6-branched α-1,4-glucans are of enormous interest since they are suitable, for instance, as regards the production of products in the pharmaceutical and cosmetic industry. They can be used, e.g. as binding agent for tablets, as carrier substances for pharmaceutical agents, as packaging material, as carrier substance for powder additives, as UV-absorbing additive in sun creme and as carrier substance of flavourings and scents.

In plants, α-1,6-branched α-1,4-glucans can mainly be found as amylopectin, a component of starch. In animals and in bacteria, glucans mainly occur in form of glycogen.

The polysaccharide starch is formed of chemically uniform basic building blocks, i.e. the glucose molecules, it is, however, a complex mixture of different forms of molecules which differ with regard to the degree of polymerization and branching and which, thus, differ strongly in their physico-chemical properties. It has to be differentiated between amylose starch, which is an essentially non-branched polymer of α-1,4-glycosidically linked glucose units, and the amylopectin starch, which is a branched polymer in which the branchings are formed due to the presence of additional α-1,6-glycosidical linkings. According to textbooks (Voet and Voet, Biochemistry, John Wiley & Sons, 1990), the α-1,6-branchings occur after every 24 to 30 glucose residues on average, which corresponds to a branching degree of approximately 3% to 4%. The indications as to the branching degree vary and depend on the origin of the respective starch (e.g. plant species, plant variety). In plants that are typically used for the industrial production of starch the share of amylose in the overall share of starch varies between 10% and 25%. Various approaches for the production of α-1,6-branched α-1,4-glucans with different branching degrees have already been described, with these approaches comprising the use of (transgenic) plants.

The heterologous expression of a bacterial glycogen synthase in potato plants, for instance, leads to a slight decrease of the amylose content, to an increase in the branching degree and to a modification of the branching pattern of the amylopectin when compared to wild type plants (Shewmaker et al., Plant. Physiol. 104 (1994), 1159-1166). Furthermore, it was observed that the heterologous expression of the branching enzyme from *E. coli* (glgB) in amylose-free potato mutants (amf) (Jacobsen et al., Euphytica 44 (1989), 43-48) leads to amylopectin molecules which have 25% more branching points (Kortstee et al., Plant J. 10 (1996), 83-90) than the control (amf). For isolating the glucans with different branching degrees, which were produced in transgenic plants, it is necessary to carry out additional purification steps in order to remove, for example, the amylose component. These purification steps are laborious and, therefore, time-consuming and cost-intensive. Furthermore, it is not possible to achieve a particular branching degree by means of these approaches. What is more, due to varying experimental conditions (environmental factors, location), such in-vivo methods vary considerably with regard to the quality of the product.

Glycogen has a higher branching degree than the amylopectin. This polysaccharide, too, contains α-1,6-branched α-1,4-glucans. Glycogen also differs from starch in the average length of the side-chains and in the degree of polymerization. According to textbooks (Voet and Voet, Biochemistry, John Wiley & Sons, 1990), glycogen contains, on average, an α-1,6-branching point after every 8 to 12 glucose residues. This corresponds to a branching degree of approximately 8% to 12%. There are varying indications as to the molecular weight of glycogen, which range from 1 million to more than 1000 millions (D. J. Manners in: Advances in Carbohydrate Chemistry, Ed. M. L. Wolfrom, Academic Press, New York (1957), 261-298; Geddes et al., Carbohydr. Res. 261 (1994), 79-89). These indications, too, strongly depend on the respective organism of origin, its state of nutrition and the kind of isolation of the glycogen. Glycogen is usually recovered from mussels (e.g. *Mytillus edulis*), from mammalian liver or muscles (e.g. rabbit, rat) (Bell et al., Biochem. J. 28 (1934), 882; Bueding and Orrell, J. Biol. Chem. 236 (1961), 2854). This renders the production on an industrial scale very time-consuming and cost-intensive.

The naturally-occurring α-1,6-branched α-1,4-glucans described, starch and glycogen, are very different depending on their content of 1,6-glycosidic branchings. This holds true, amongst others, with regard to solubility, transparency, enzymatic hydrolysis, rheology, gel formation and retrogradation properties. For many industrial applications, such variations in the properties, however, cannot always be tolerated.

In-vitro approaches are an alternative to the recovery of α-1,6-branched α-1,4-glucans from plants or animal organisms. Compared to in-vivo methods, in-vitro methods are generally better to control and are reproducible to a greater extent since the reaction conditions in vitro can be exactly adjusted in comparison with the conditions in a living organism. This usually allows the production of invariable products with a high degree of uniformity and purity and, thus, of high quality, which is very important for any further industrial application. The preparation of products of a steady quality leads to a reduction of costs since the procedural parameter that are necessary for the preparation do not have to be optimised for every preparation set-up. Another advantage of certain in-vitro methods is the fact that the products are free of the organisms used in the in-vivo method. This is absolutely necessary for particular applications in the food and pharmaceutical industries.

In general, in-vitro methods can be divided into two different groups.

In the first group of methods, various substrates, such as amylose, amylopectin and glycogen, are subjected to the activity of a branching enzyme.

Borovsky et al. (Eur. J. Biochem. 59 (1975), 615-625) were able to prove that using the branching enzyme from potato in connection with the substrate amylose leads to products that are similar to amylopectin, but that differ from it in their structure.

Boyer and Preiss (Biochemistry 16 (1977), 3693-3699) showed, in addition, that a purified branching enzyme (α-1,4-glucan: α-1,4-glucan 6-glycosyltransferase) from *E. coli* may be used to increase the branching degree of amylose or amylopectin.

If, however, glycogen from *E. coli* or rabbit liver is incubated with the branching enzyme from *E. coli*, only a slight increase in the branching degree can be achieved (Boyer and Preiss, loc. cit.).

Rumbak et al. (J. Bacteriol. 173 (1991), 6732-6741), too, could subsequently increase the branching degree of amylose, amylopectin and glycogen by incubating these substrates with the branching enzyme from *Butyrivibrio fibrisolvens*.

Okada et al. made a similar approach (U.S. Pat. No. 4,454,161) to improve the properties of starch-containing foodstuffs. They incubated substances, such as amylose, amylopectin, starch or dextrin with a branching enzyme. This had advantageous effects on the durability of foodstuffs containing substances that were modified correspondingly. Furthermore, the patent application EP-A1 0 690 170 describes the reaction of jellied starch in an aqueous solution using a branching enzyme. This results in starches having advantageous properties in the production of paper.

However, the aforementioned in-vitro methods have the disadvantage that they, due to the varying branching degree of the educts (e.g. starch, amylopectin, etc.), make it impossible to produce uniform products. In addition, it is not possible to intentionally control the branching degree and, what is more, the substrates used are quite expensive.

The other group of in-vitro methods comprises the de-novo synthesis of α-1,6-branched α-1,4-glucans starting from various substrates (glucose-1-phosphate, ADP glucose, UDP glucose) using a combination of enzymes that consists of a 1,4-glucan-chain-forming enzyme (phosphorylase, starch synthase, glycogen synthase) and a branching enzyme.

Illingwort et al. (Proc. Nat. Acad. Sci. USA 47 (1961), 469-478) were able to show for an in-vitro method using a phosphorylase A from muscles (organism unknown) in combination with a branching enzyme (organism unknown) that the de-novo synthesis of molecules similar to glycogen using the substrate glucose-1-phosphate was possible. Boyer and Preiss (loc. cit.) combined the enzymatic activity of a phosphorylase from rabbit muscles or a glycogen synthase from *E. coli* with the activity of a branching enzyme from *E. coli* using the substrate glucose-1-phosphate or UDP glucose and in this way generated branched α-glucans. Borovsky et al. (Eur. J. Biochem. 59 (1975), 615-625), too, analysed the de-novo synthesis of α-1,6-branched α-1,4-glucans from glucose-1-phosphate using a branching enzyme from potato in combination with a phosphorylase (1,4-α-D-glucan: orthophosphate α-glycosyltransferase [EC 2.4.1.1]) from maize. Doi (Biochimica et Biophysica Acta 184 (1969), 477-485) showed that the enzyme combination of a starch synthase (ADP-D-glucose: α-1,4-glucan α-4-glucosyltransferase) from spinach and a branching enzyme from potato using the substrate ADP glucose resulted in products similar to amylopectin. Parodi et al. (Arch. Biochem. Biophys. 132 (1969), 11-117) used a glycogen synthase from rat liver combined with a branching enzyme from rat liver for the de-novo synthesis of branched glucans from UDP glucose. They obtained a polymer which was similar to native glycogen and which differs from the polymers that are based on glucose-1-phosphate.

This second group of in-vitro methods, too, has the disadvantage that the substrates, e.g. glucose-1-phosphate, UDP glucose and ADP glucose, are very expensive. Furthermore, it does not seem to be possible either to intentionally control the branching degree.

Büttcher et al. (J. Bacteriol. 179 (1997), 3324-3330) describe an in-vitro method for the production of water-insoluble α-1,4-glucans using an amylosucrase and sucrose as substrates. However, only linear α-1,4-glucans without branchings are synthesized.

Thus, the technical problem underlying the present invention is to provide a method allowing the cheap production of α-1,6-branched α-1,4-glucans for industrial purposes, as well as nucleic acid molecules encoding the enzymes that may be used in said methods, in particular branching enzymes.

This technical problem has been solved by providing the embodiments characterised in the claims.

From left to right: amylosucrase (left), amylosucrase+decreasing amounts of branching enzyme activity. The maximum absorption of the corresponding samples were: 615 nm, 483 nm, 500 nm, 526 nm, 534 nm, 560 nm, 577 nm.

Figure 3:
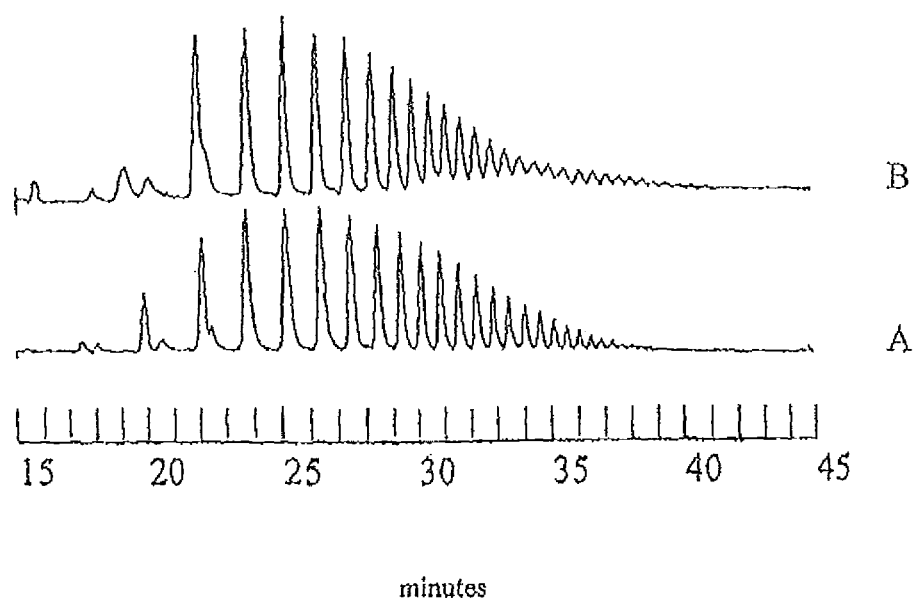

FIG. 3 shows a HPLC chromatograph of a highly branched process product (A) which has been debranched with isoamylase and a rat liver glycogen sample (B) which has been debranched with isoamylase.

Figure 4:
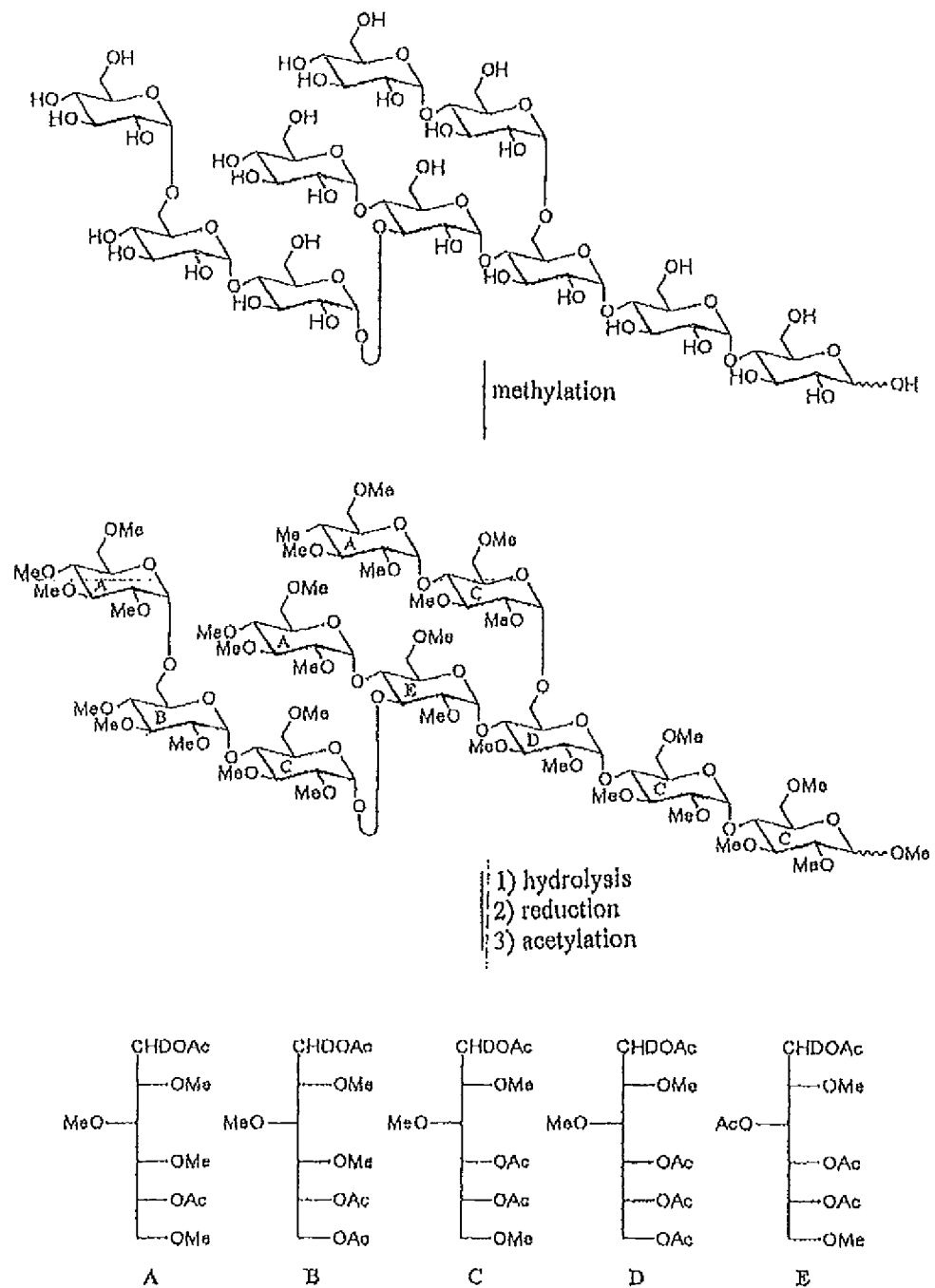

FIG. 4 shows the scheme of the methylation analysis.

Figure 5:
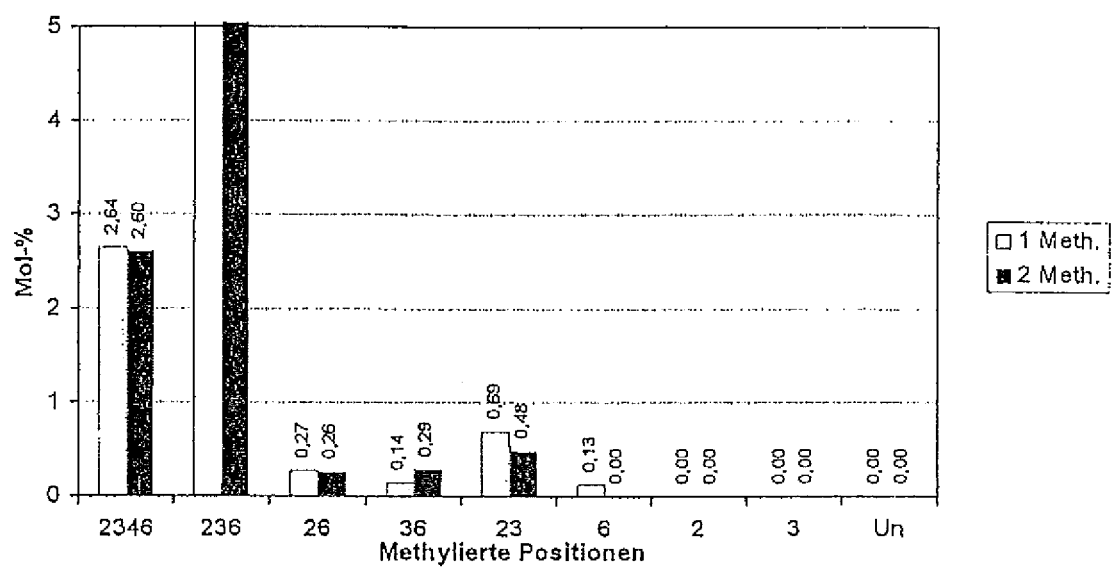

FIG. 5 shows a diagram of the results of the analysis of sample 7 described in Examples 9 and 10 after one and after two methylation steps. The values for the 2,3,6-methylation are 96.12% and 96.36%, respectively.

Figure 6:
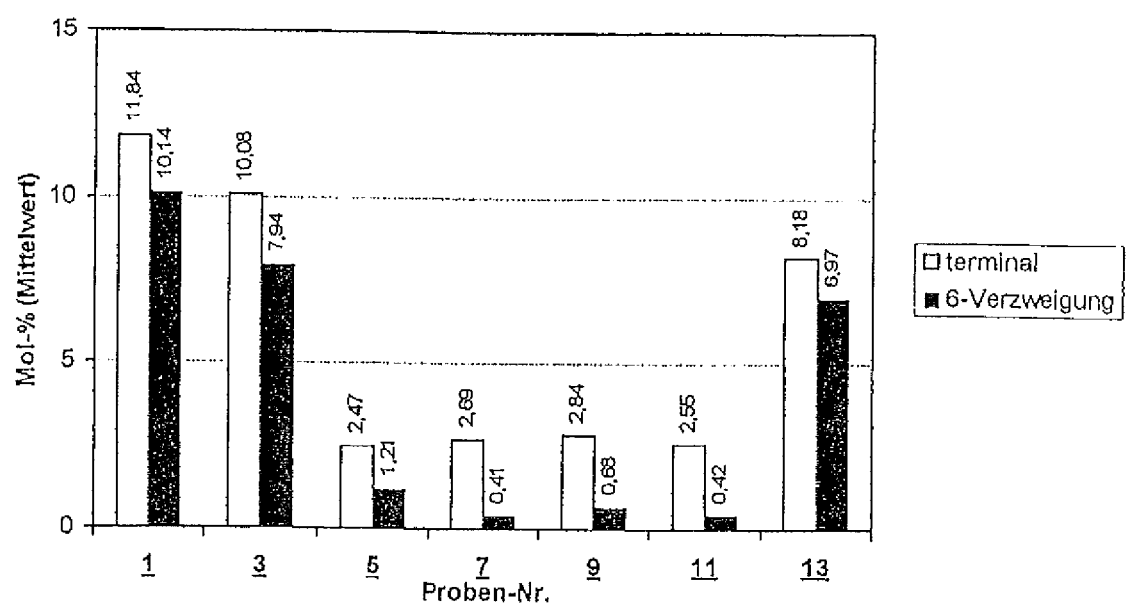

FIG. 6 shows a graphic illustration of the shares in terminal ("2346 Me") and 6-linked ("23 Me") glucose units of the glucan samples examined.

Figure 7:
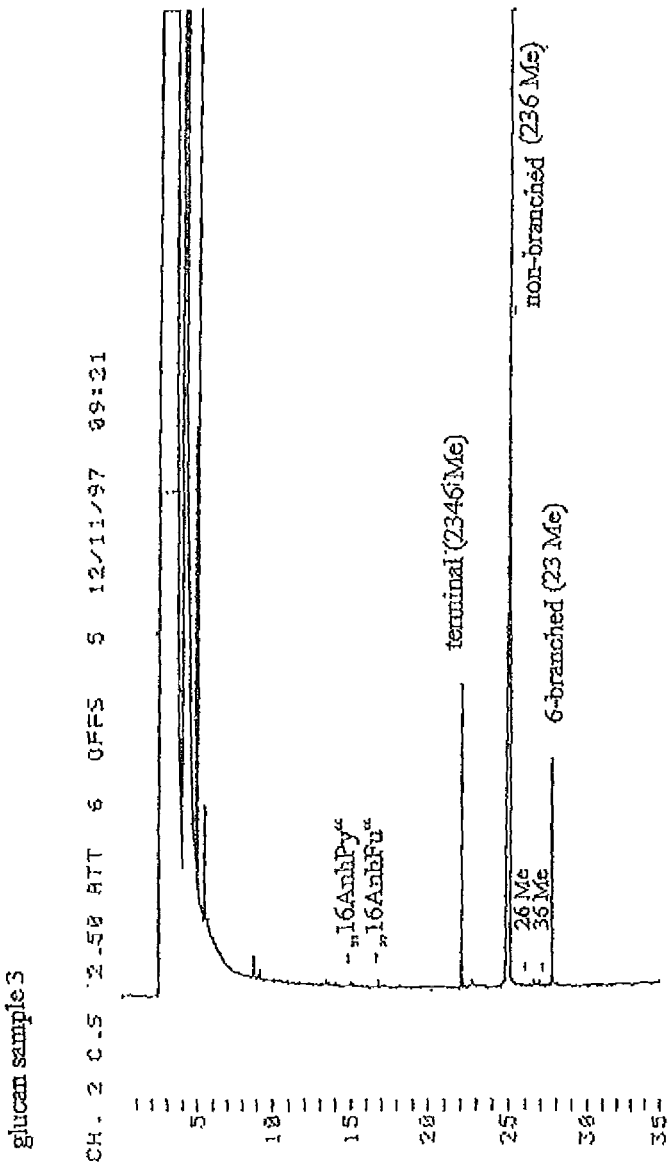
Figure 8:
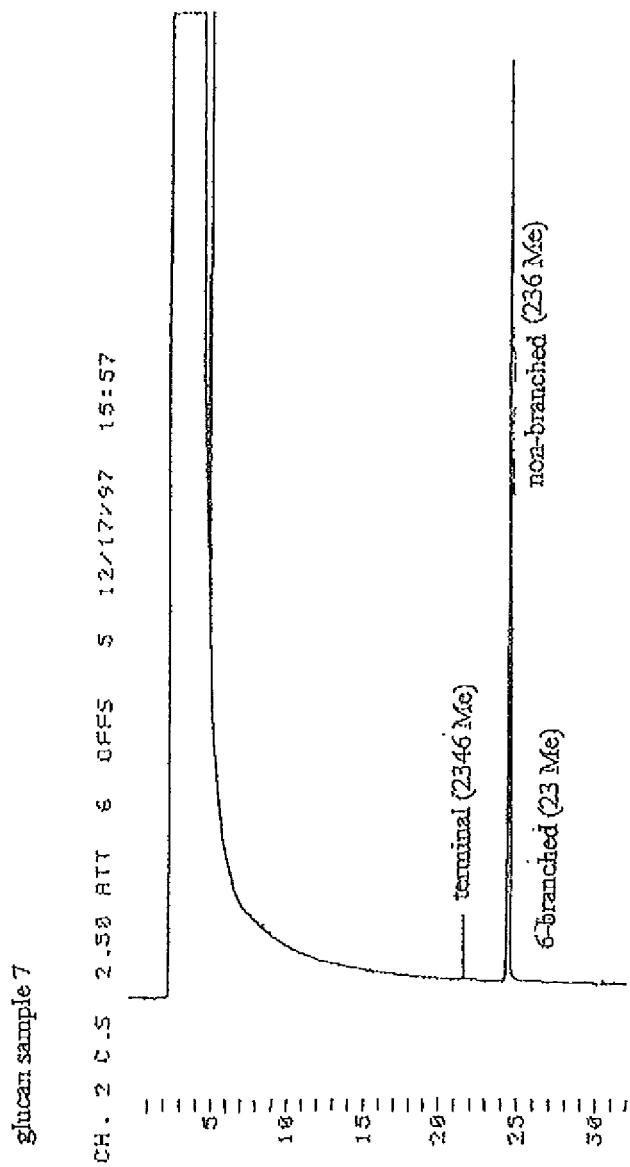

FIGS. 7 and 8 show gas chromatographs of the samples 3 and 7 described in the Examples.

Figure 9:
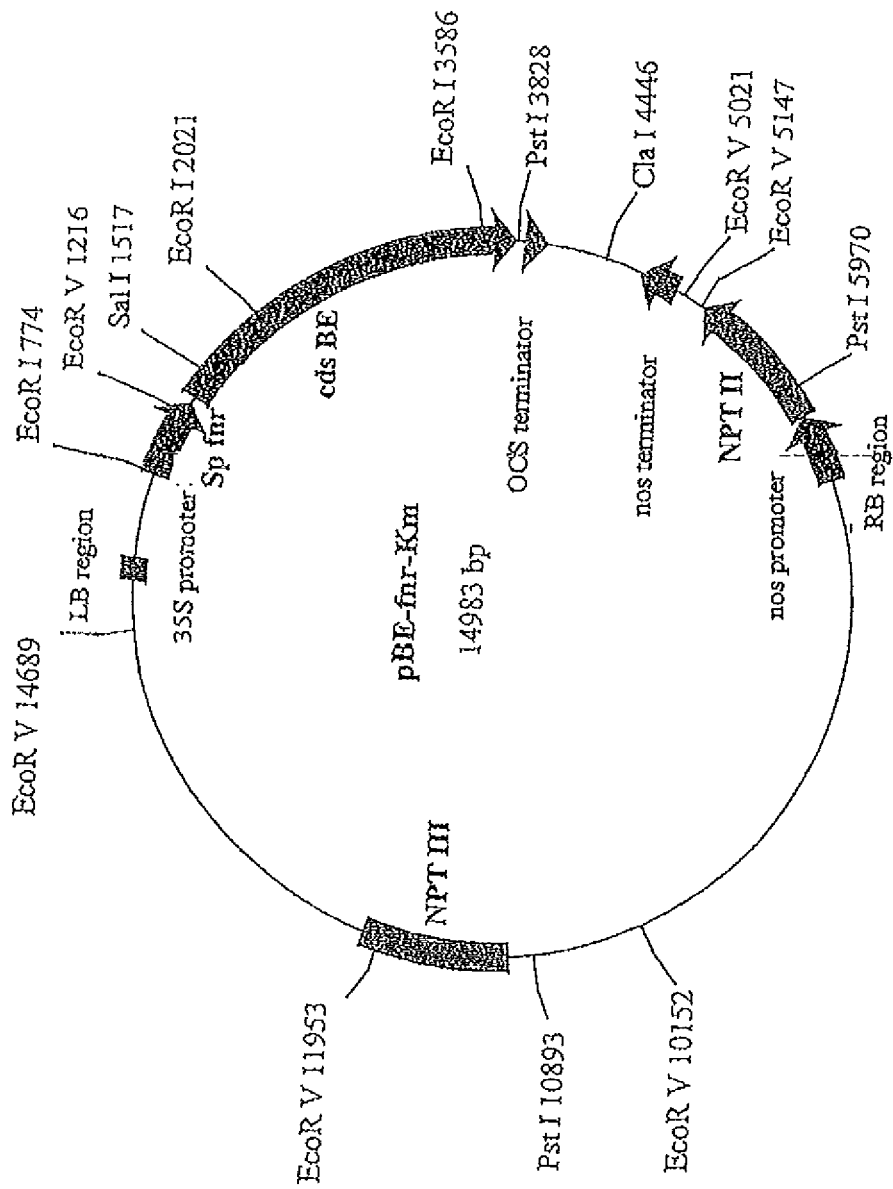

FIG. 9 schematically shows the plasmid pBE-fnr-Km.

Figure 10:
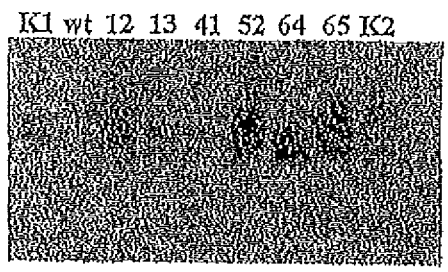

FIG. 10 shows an activity gel for the branching enzyme.

Figure 11:
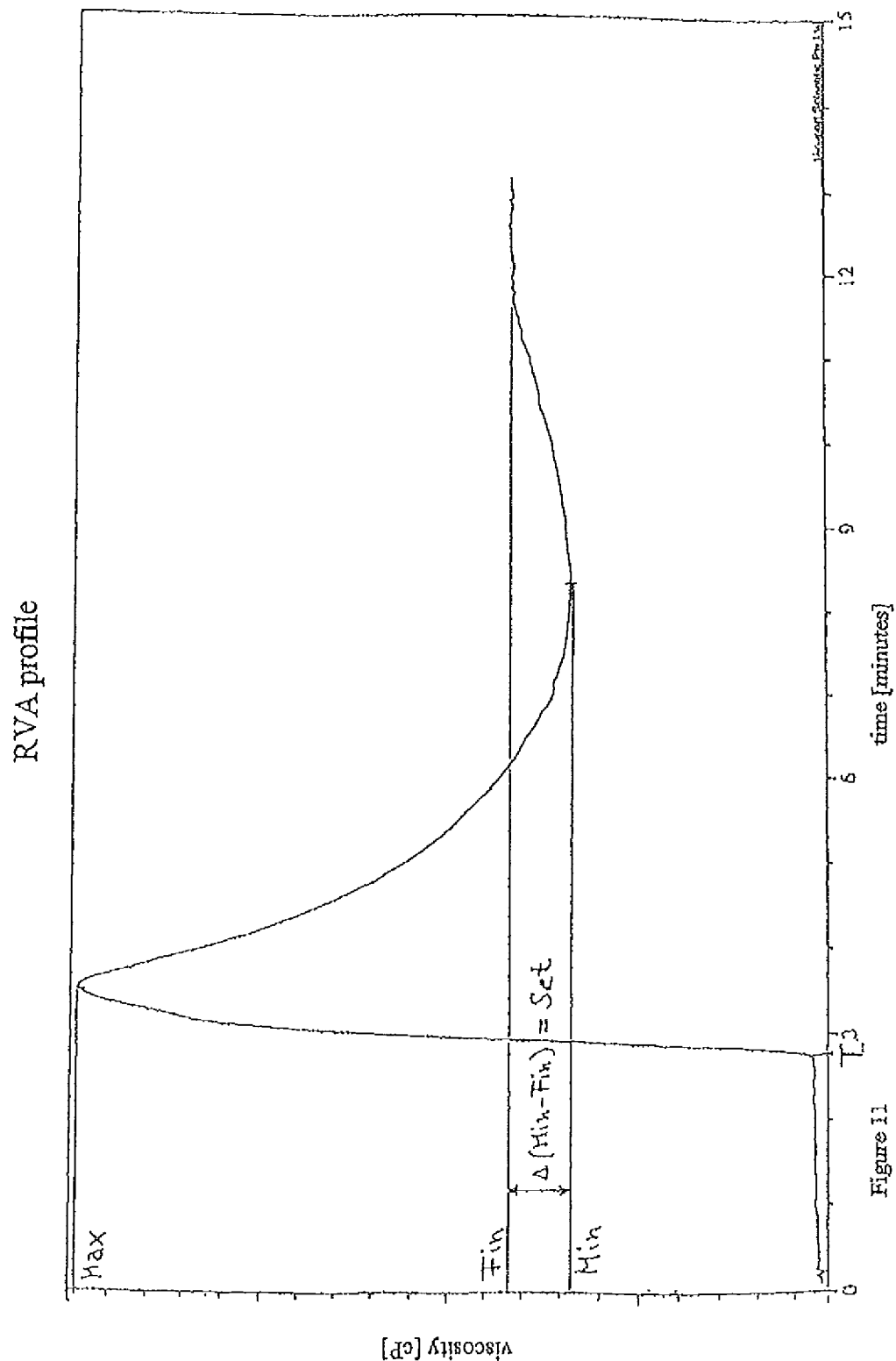

FIG. 11 shows the schematic illustration of an RVA profile.

Figure 12:
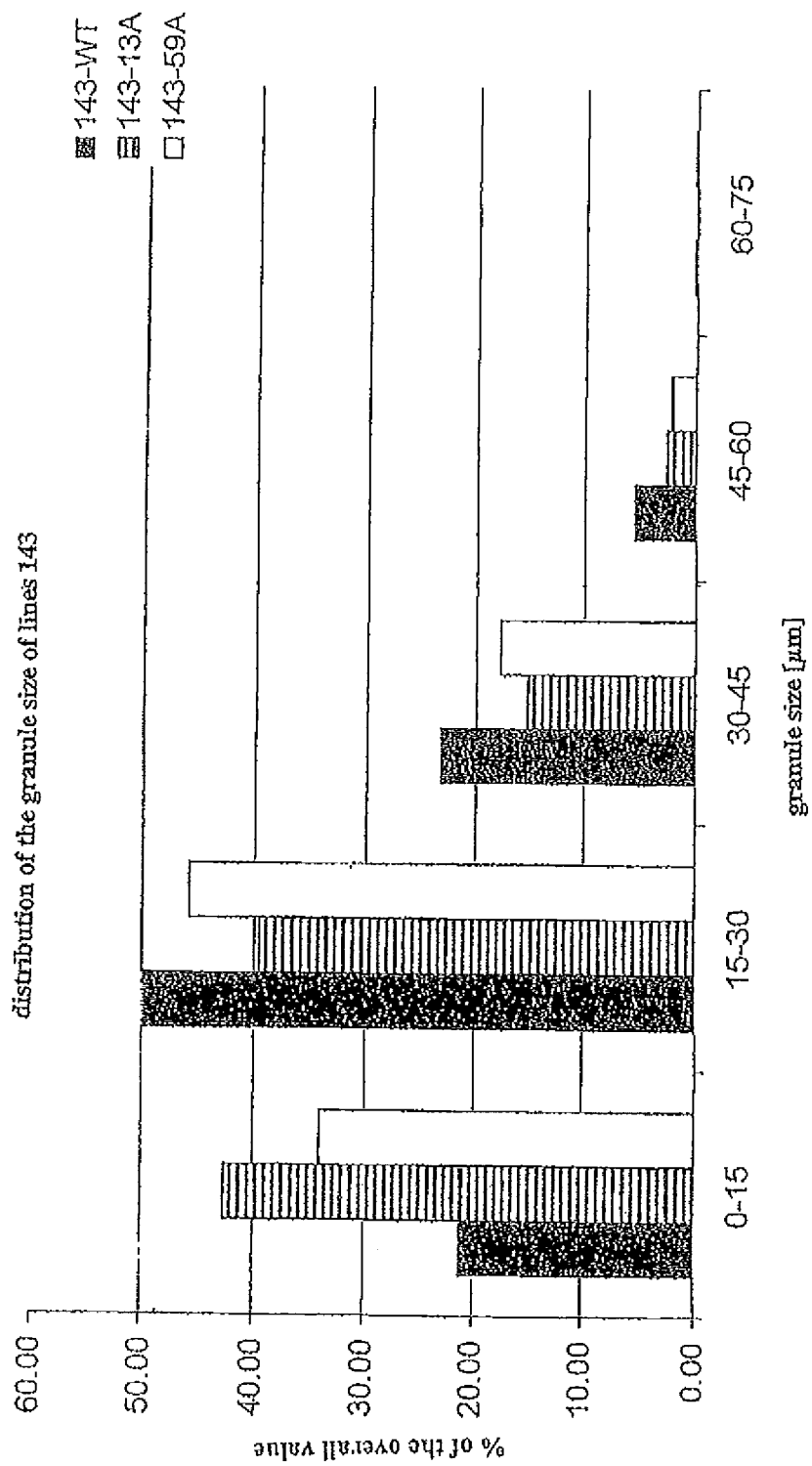

FIG. 12 shows the distribution of granule size of the lines 143-13A and 143-59A compared to the wild type.

Figure 13:
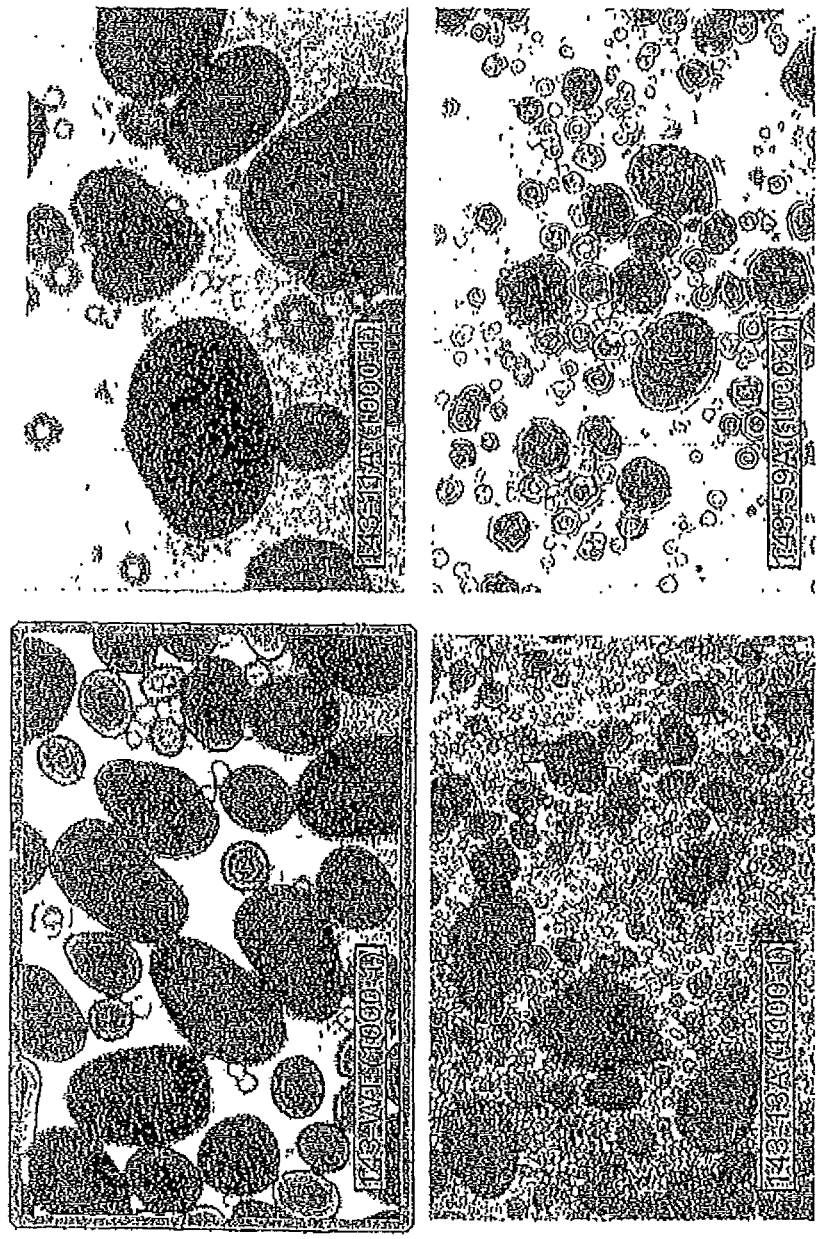

FIG. 13 shows the microscopic magnification of the starch granules of the lines 143-13A, 143-34A and 143-59A in comparison with the starch granules of wild type plants (light microscope by Leitz, Germany).

Figure 14:
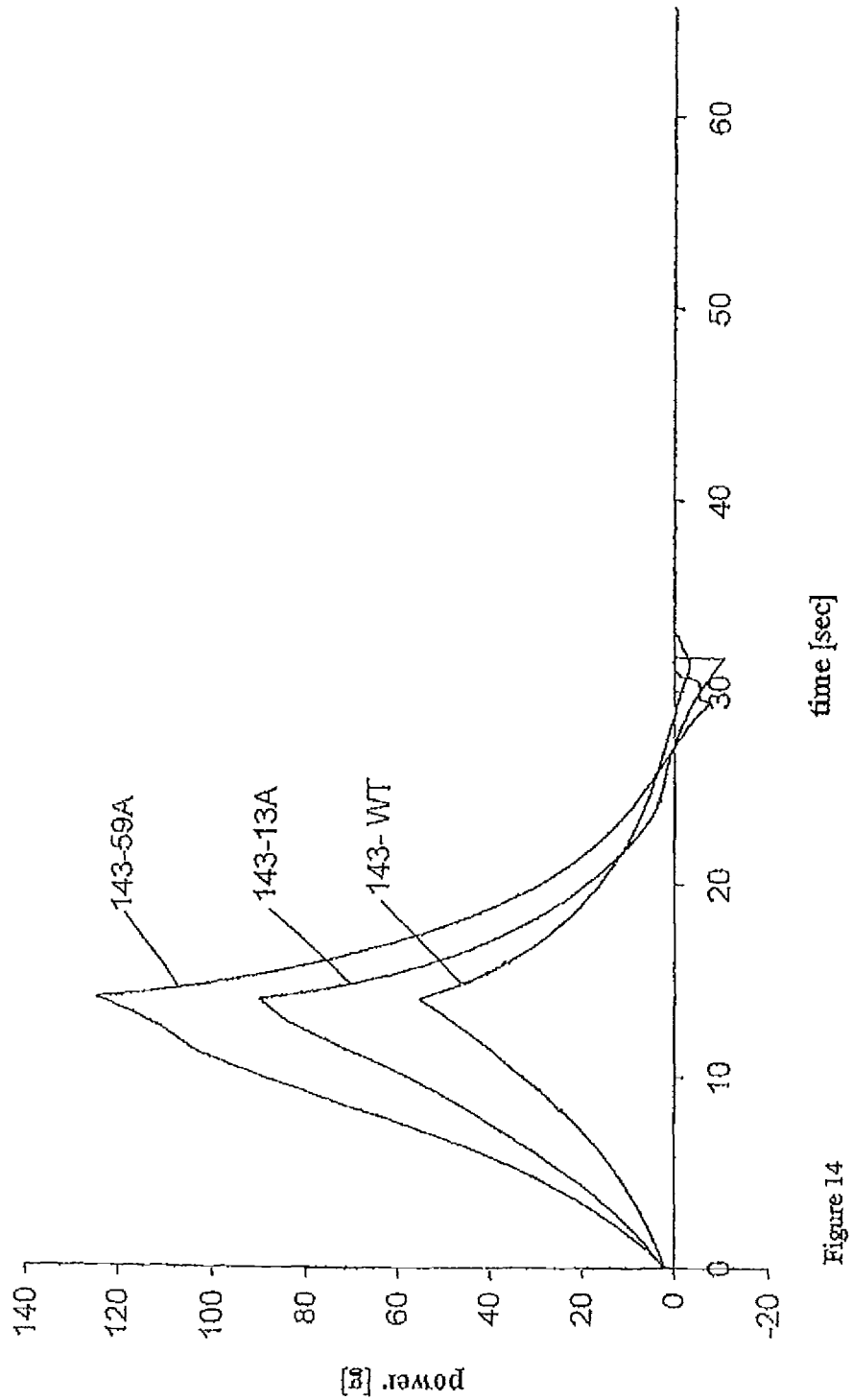

FIG. 14 shows the gel texture of the starches of different transgenic lines compared to starches from wild type plants. The texture was determined by means of a texture analyzer.

Figure 15:
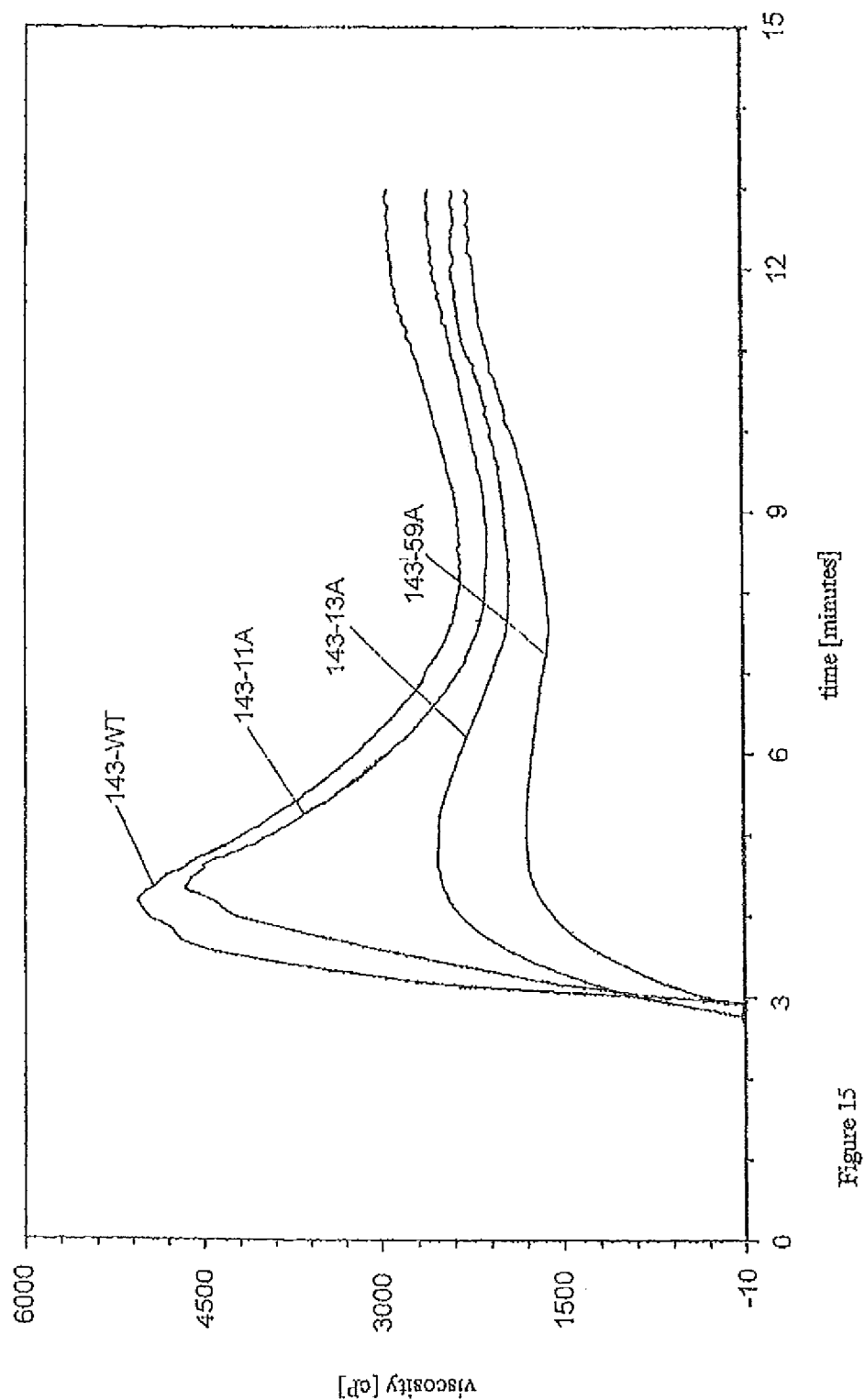

FIG. 15 shows the RVA profile of the starches of the lines 143-11A, 143-13A, 143-59A compared to the wild type.

Figure 16:
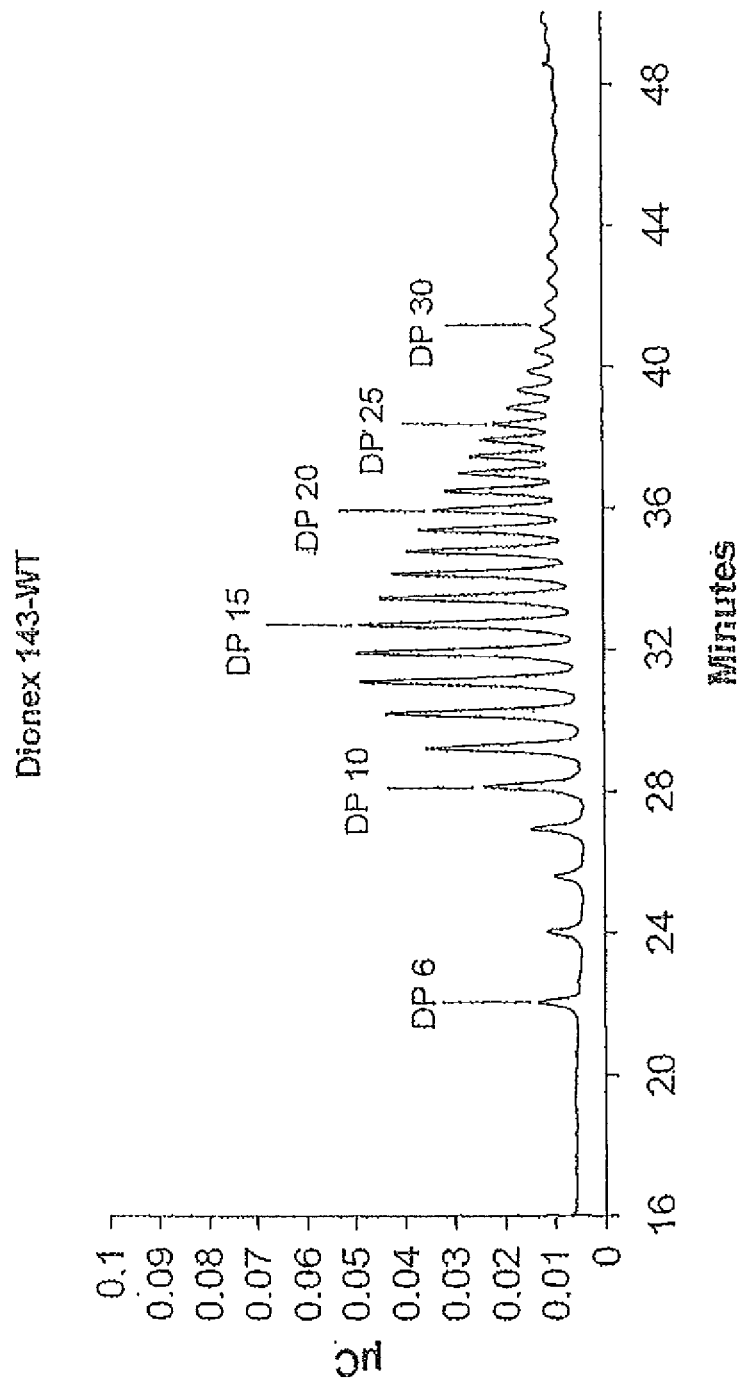
Figure 17:
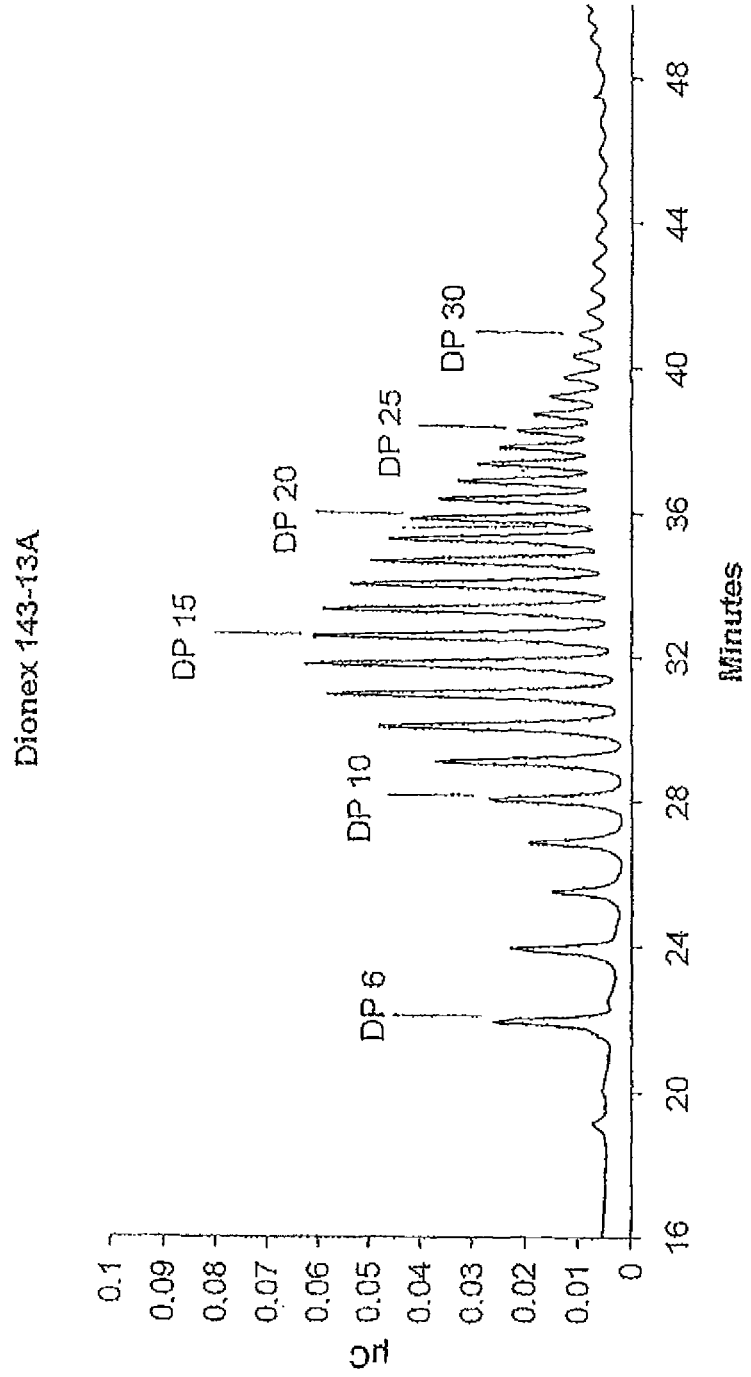
Figure 18:
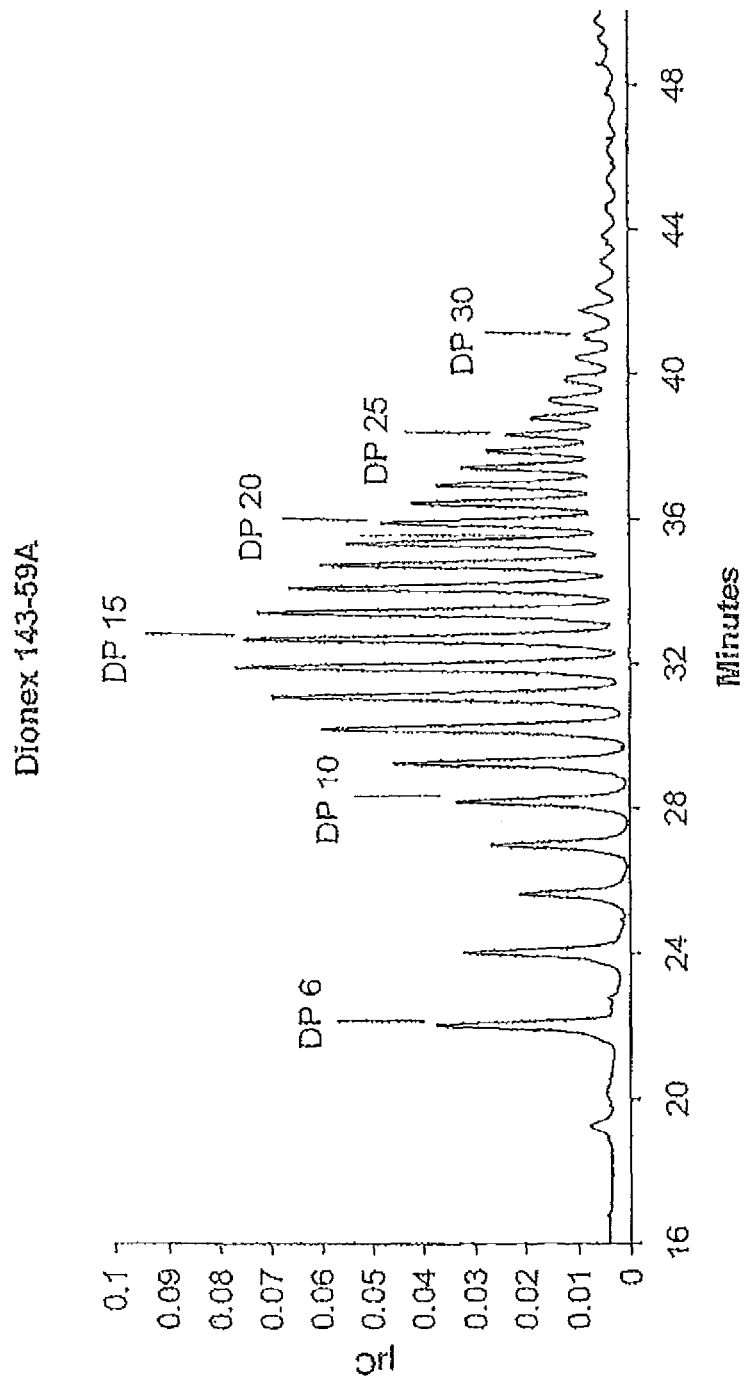

FIGS. 16 to 18 show the results of HPLC chromatographies which represent the pattern of the distribution of the side-chains of the lines 143-WT (=wild type), 143-13A and 143-59A.

Figure 19:
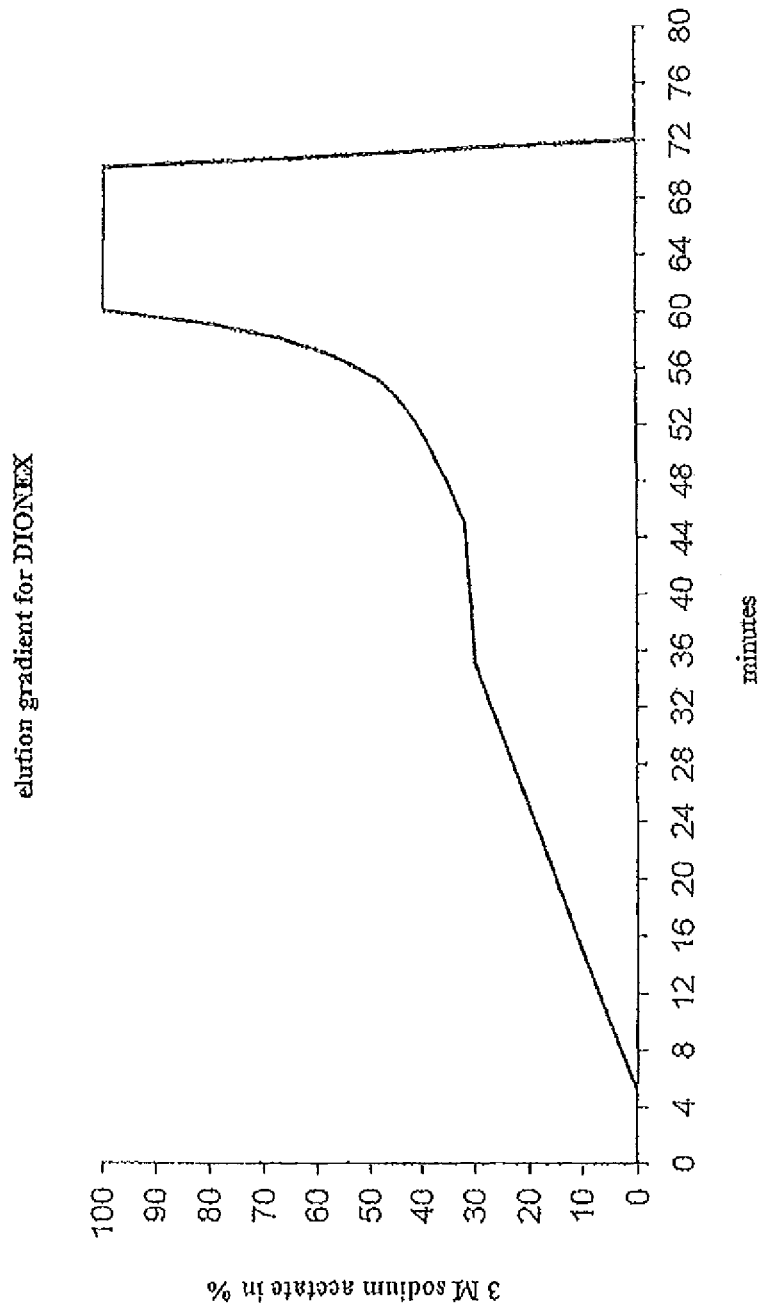

FIG. 19 shows the elution gradient that was used for the chromatographies depicted in FIGS. 16 to 18.

Figure 20:
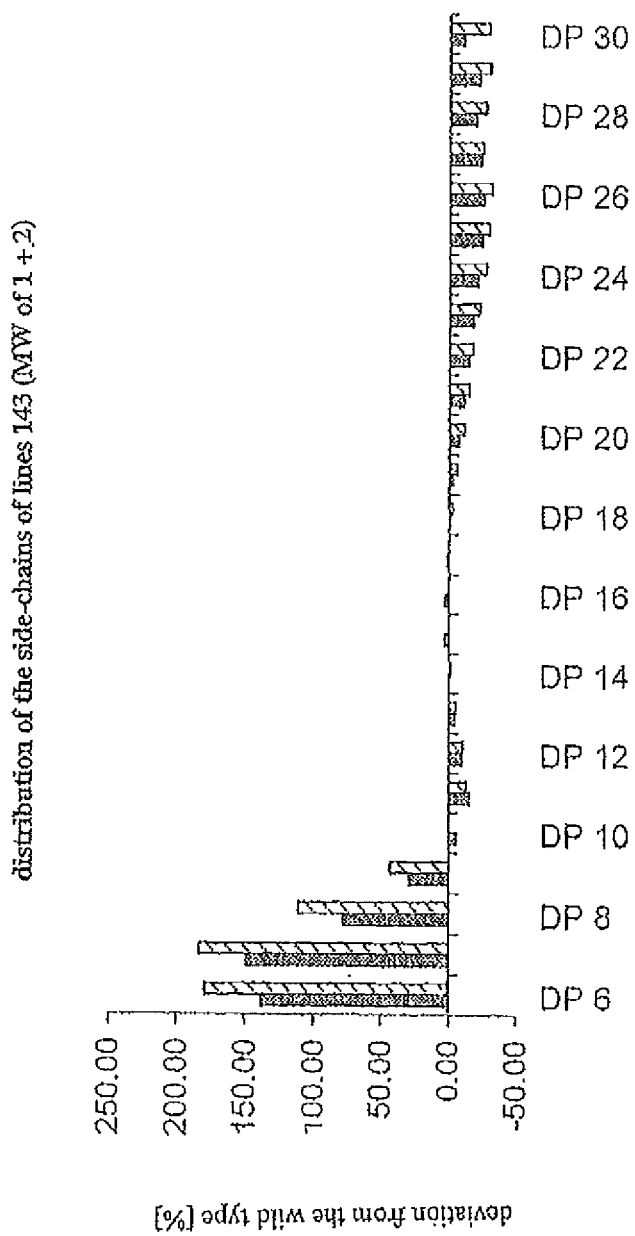

FIG. 20 shows the percentage deviation of side-chains having certain chain lengths of the starches analysed in FIGS. 16 to 18 from the wild type.

Therefore, the present invention relates to nucleic acid molecules encoding a branching enzyme (EC 2.4.1.18) from bacteria of the genus *Neisseria* selected from the group consisting of (a) nucleic acid molecules encoding a protein which comprises the amino acid sequence depicted in SEQ ID NO. 2;

(b) nucleic acid molecules comprising the nucleotide sequence of the coding region which is depicted in SEQ ID NO. 1;

(c) nucleic acid molecules encoding a protein which comprises the amino acid sequence that is encoded by the insert of the plasmid DSM 12425;

(d) nucleic acid molecules comprising the region of the insert of the plasmid DSM 12425, which encodes a branching enzyme from *Neisseria denitrificans*;

(e) nucleic acid molecules encoding a protein the sequence of which has within the first 100 amino acids a homology of at least 65% with regard to the sequence depicted in SEQ ID NO. 2;

(f) nucleic acid molecules the complementary strand of which hybridizes to a nucleic acid molecule according to (a), (b), (c), (d) and/or (e) and which encode a branching enzyme from a bacterium of the genus *Neisseria*; and (g) nucleic acid molecules the nucleic acid sequence of which differs from the sequence of a nucleic acid molecule according to (f) due to the degeneracy of the genetic code.

The nucleic acid sequence depicted in SEQ ID NO. 1 is a genomic sequence which comprises a coding region for a branching enzyme from *Neisseria denitrificans*. A plasmid containing said DNA sequence has been deposited as DSM 12425. By means of said sequence or said molecule, the person skilled in the art can now isolate homologous sequences from other *Neisseria* species or *Neisseria* strains. He/she may do so using conventional methods, like screening of cDNA or genomic libraries with suitable hybridization probes. The homologous sequences may also be isolated as described in Example 1. Thus, it is possible, for example, to identify and isolate nucleic acid molecules that hybridize to the sequence depicted in SEQ ID NO. 1 and that encode a branching enzyme.

The nucleic acid molecules of the invention may, in principle, encode a branching enzyme from any bacterium of the genus *Neisseria*, they preferably encode a branching enzyme from *Neisseria denitrificans*.

According to the present invention, the term "hybridization" means hybridization under conventional hybridization conditions, preferably under stringent conditions as have been described, e.g. in Sambrook et al., Molecular Cloning, A Laboratory Manual, 2$^{nd}$ edition (1989) Cold Spring Harbor Laboratory Press, Cold Spring Harbor, N.Y. The term "hybridization" is particularly preferred to mean a hybridization under the following conditions:

hybridization buffer: 2×SSC; 10×Denhardt solution (Fikoll 400+PEG+BSA; at a ratio of 1:1:1); 0.1% SDS; 5 mM EDTA; 50 mM Na$_2$HPO$_4$; 250 µg/ml herring sperm DNA; 50 µg/ml tRNA; or 25 M sodium phosphate buffer, pH 7.2; 1 mM EDTA; 7% SDS hybridization temperature: T=65 to 68° C.
washing buffer: 0.2×SSC; 0.1% SDS
washing temperature: T=65 to 68° C.

Nucleic acid molecules hybridizing to the nucleic acid molecules of the invention may, in principle, be derived from any bacterium of the genus *Neisseria* which expresses a corresponding protein, preferably they are derived from *Neisseria denitrificans*. Nucleic acid molecules hybridizing to the molecules of the invention, may, for instance, be isolated from genomic or from cDNA libraries. Such nucleic acid molecules can be identified and isolated using the nucleic acid molecules of the invention or parts of said molecules or the reverse complements of said molecules, e.g. by hybridizing according to standard techniques (cf. Sambrook et al., Molecular Cloning, A Laboratory Manual, 2$^{nd}$ edition (1989) Cold Spring Harbor Laboratory Press, Cold Spring Harbor, N.Y.) or by amplification by means of PCR.

As hybridization probe nucleic acid molecules can be used which have exactly or essentially the nucleotide sequence depicted in SEQ ID NO. 1 or parts thereof. The fragments used as hybridization probes may also be synthetic fragments which have been produced by means of conventional synthesis techniques and the sequence of which is essentially identical to the one of a nucleic acid molecule of the invention. If genes have been identified and isolated to which the nucleic acid sequences of the invention hybridize, the sequence should be determined and the properties of the proteins encoded by said sequence should be analysed to find out whether they are branching enzymes. For this purpose, it is particularly suitable to compare the homology on the nucleic acid and amino acid sequence level and to determine the enzymatic activity.

The molecules hybridizing to the nucleic acid molecules of the invention comprise, in particular, fragments, derivatives and allelic variants of the above-described nucleic acid molecules encoding a branching enzyme from bacteria of the genus *Neisseria*, preferably from *Neisseria denitirificans*. In this context, the term "derivative" means that the sequences of said molecules differ from the sequences of the aforementioned nucleic acid molecules in one of more positions and have a high degree of homology to said sequences. Homology, in this context, means that there is, over the entire length, a sequence identity of at least 60%, in particular an identity of at least 70%, preferably of more than 80%, more preferably of more than 90% and most preferably of at least 95%. The deviations from the above-described nucleic acid molecules may be caused by, e.g. deletion, addition, substitution, insertion or recombination.

Furthermore, homology means that there is a functional and/or structural equivalence between the respective nucleic acid molecules or the proteins encoded by these. The nucleic acid molecules which are homologous to the aforementioned molecules and which are derivatives of said molecules are usually variations of said molecules which are modifications that have the same biological functions. These may be both naturally-occurring variations, e.g. sequences from other *Neisseria* species or *Neisseria* strains and mutations with these mutations occurring naturally or being introduced by directed mutagenesis. Furthermore, the variations may be sequences produced synthetically. The allelic variants may be both naturally-occurring variants and variants that have been produced synthetically or by recombinant DNA techniques.

The proteins encoded by the different variants of the nucleic acid molecules of the invention have certain characteristics in common. These may include, for instance, biological activity, molecular weight, immunological reactivity, conformation, etc., as well as physical properties, such as the migration behaviour in gel electrophoreses, chromatographic behaviour, sedimentation coefficients, solubility, spectroscopic properties, stability; pH optimum, temperature optimum, etc.

The molecular weight of the branching enzyme from *Neisseria denitrificans* is 86.3 kDa, with the molecular weight being deduced from the amino acid sequence. Hence, the deduced molecular weight of a protein of the invention preferably ranges from 70 kDa to 100 kDa, more preferably from 77 kDa to 95 kDa and most preferably it is about 86 kDa.

The present invention also relates to nucleic acid molecules encoding a protein having the enzymatic activity of a branching enzyme with the encoding protein having a homology of at least 65%, preferably of at least 80% and most preferably of at least 95% in the region of the N-terminus, preferably in the first 100 amino acids, more preferably in the first 110 amino acids and most preferably in the first 120 amino acids to the amino acid sequence depicted in SEQ ID NO. 2.

In another embodiment, the present application relates to nucleic acid molecules encoding a protein having activity of a branching enzyme, the protein comprising at least one, preferably at least 5, more preferably at least 10 and most preferably at least 20 of the following peptide motifs:

| | | |
|---|---|---|
| (a) | MNRNRHI, | (SEQ ID NO. 8) |
| (b) | RPDAHH, | (SEQ ID NO. 9) |
| (c) | HAPDYAL, | (SEQ ID NO. 10) |
| (d) | EGEAA, | (SEQ ID NO. 11) |
| (e) | DDYRF, | (SEQ ID NO. 12) |
| (f) | SALQH, | (SEQ ID NO. 13) |
| (g) | YETLG, | (SEQ ID NO. 14) |
| (h) | VSGVR, | (SEQ ID NO. 15) |
| (i) | VSVIG, | (SEQ ID NO. 16) |
| (j) | FNGWD, | (SEQ ID NO. 17) |
| (k) | LYKFS, | (SEQ ID NO. 18) |
| (l) | PYAFG, | (SEQ ID NO. 19) |
| (m) | RPTTAS, | (SEQ ID NO. 20) |
| (n) | FRRRA, | (SEQ ID NO. 21) |
| (o) | DELVNY, | (SEQ ID NO. 22) |
| (p) | LPLSEY, | (SEQ ID NO. 23) |
| (q) | YQATGL, | (SEQ ID NO. 24) |
| (r) | DDHGL, | (SEQ ID NO. 25) |
| (s) | HQDWN, | (SEQ ID NO. 26) |
| (t) | DGIRV, | (SEQ ID NO. 27) |
| (u) | YGGSEN, | (SEQ ID NO. 28) |
| (v) | SFAEES, | (SEQ ID NO. 29) |
| (w) | DPVHR, | (SEQ ID NO. 30) |
| (x) | WQQFAN, | (SEQ ID NO. 31) |
| (y) | EILNS, | (SEQ ID NO. 32) |
| (z) | ATEIQTAL, | (SEQ ID NO. 33) |
| (aa) | VKDKQAKAK. | (SEQ ID NO. 34) |

The nucleic acid molecules of the invention may be any nucleic acid molecules, in particular DNA or RNA molecules, e.g. cDNA, genomic DNA, mRNA, etc. They may be naturally-occurring molecules or molecules produced by means of genetic or chemical synthesis techniques. They may be single-stranded molecules which either contain the coding or the non-coding strand, or they may also be double-stranded molecules.

Furthermore, the present invention relates to nucleic acid molecules which are at least 15, preferably more than 50 and most preferably more than 200 nucleotides in length, these nucleic acid molecules specifically hybridizing to at least one nucleic acid molecule of the invention. In this context, the term "specifically hybridizing" means that said molecules hybridize to nucleic acid molecules encoding a protein of the invention, however, not to nucleic acid molecules encoding other proteins. The term "hybridizing" means preferably hybridizing under stringent conditions (see above). In particular, the invention relates to nucleic acid molecules which hybridize to transcripts of nucleic acid molecules of the invention and which, thus, can prevent the translation thereof. Such nucleic acid molecules which specifically hybridize to the nucleic acid molecules of the invention may, for instance, be components of anti-sense constructs or ribozymes or may be used as primers for amplification by means of PCR.

Moreover, the invention relates to vectors, in particular plasmids, cosmids, viruses, bacteriophages and other vectors that are usually used in genetic engineering and that contain the above-described nucleic acid molecules of the invention.

In a preferred embodiment, the nucleic acid molecules contained in the vectors are linked in sense-orientation to regulatory elements guaranteeing expression in prokaryotic or eukaryotic cells. In this context, the term "expression" means both transcription or transcription and translation.

The expression of the nucleic acid molecules of the invention in prokaryotic cells, e.g. in *Escherichia coli*, allows, for instance, a more exact characterisation of the enzymatic activities of the proteins encoded. In addition, it is possible to introduce various mutations into the nucleic acid molecules of the invention by means of conventional techniques of molecular biology (cf. e.g. Sambrook et al., loc. cit.). This leads to the synthesis of proteins the properties of which have optionally been modified. It is also possible to produce deletion mutants by continued deletion of the 5' or 3' end of the encoding DNA sequence, which results in the generation of nucleic acid molecules leading to the synthesis of correspondingly shortened proteins. Moreover, it is possible to introduce point mutations at positions that influence, for instance, the enzyme activity or the regulation of the enzyme. In this way, mutants may be generated that have a modified Km value or that are no longer subjected to the usual regulation mechanisms in the cells via allosteric regulation or covalent modification. In addition, mutants may be produced which have a modified substrate or product specificity. Furthermore, mutants may be produced which have a modified activity-temperature profile. The genetic manipulation in prokaryotic cells may be carried out according to methods known to the skilled person (cf. Sambrook et al., loc. cit.).

Regulatory sequences for the expression in prokaryotic organisms, e.g. *E. coli*, and in eukaryotic organisms have been sufficiently described in the literature, in particular sequences for the expression in yeast, such as *Saccharomyces cerevisiae*. Methods in Enzymology 153 (1987), 383-516 and Bitter et al. (Methods in Enzymology 153 (1987), 516-544) give an overview of various systems for the expression for proteins in various host organisms.

Preferably, the nucleic acid molecule of the invention which has been inserted in a vector of the invention is modified in such a way that it is easier to isolate the encoded protein from the culture medium after it had been expressed in a suitable host organism. There is, for instance, the possibility of expressing the encoded branching enzyme as a fusion protein together with a further polypeptide sequence the specific binding properties of which allow the isolation of the fusion protein by means of affinity chromatography (cf. Chong et al., Gene 192 (1997), 271-281; Hopp et al., Bio/Technology 6 (1988), 1204-1210; Sassenfeld, Trends Biotechnol. 8 (1990), 88-93).

Furthermore, the nucleic acid molecule contained in vector of the invention is preferred to comprise nucleotide sequences which allow the secretion of the branching enzyme into the culture medium. Preferably, a sequence is used which codes for the signal peptide of the α-CGTase from *Klebsiella oxytoca* M5A1 (Fiedler et al., J. Mol. Biol. 256 (1996), 279-291; Genebank acc. no. X86014, CDS 11529-11618). The recovery and the purification is made easier by the secretion of the enzyme into the culture medium. A disruption of the cells is avoided and the enzyme can be recovered from the culture medium with conventional methods, such as dialysis, osmosis, chromatographic methods, etc. being used for removing residuary components of the culture medium.

Furthermore, the vectors of the invention may comprise other functional units which may bring about a stabilisation of the vector in a host organism, such as a bacterial replication origin or the 2μ-DNA for the stabilisation in *S. cerevisiae*.

In another embodiment, the invention relates to host cells, in particular to prokaryotic or eukaryotic cells which have been transformed with a nucleic acid molecule or a vector as described above, as well as to cells which are derived from said host cells and which contain the described nucleic acid molecules or vectors. The host cells may be bacterial cells (e.g. *E. coli*) or fungal cells (e.g. yeast, in particular *S. cerevisiae*), as well as plant or animal cells. The term "transformed" means that the cells of the invention have been genetically modified with a nucleic acid molecule of the invention in so far as they contain at least one nucleic acid molecule of the invention in addition to their natural genome. Said nucleic acid molecule may be present free in the cell, optionally as self-replicating molecule, or it may be stably integrated into the genome of the host cell.

The host cells are preferred to be microorganisms. Within the present invention, such microorganisms may be all bacteria and all protista (e.g. fungi, in particular yeasts and algae) as have been defined, for instance, in Schlegel "Allgemeine Mikrobiologie" (Georg Thieme Verlag (1985), 1-2).

The host cells of the invention are particularly preferred to be plant cells. In principle, these may include plant cells from any plant species, i.e. both from monocotyledonous and dicotyledonous plants. Preferably, said cells are plant cells from agricultural useful plants, i.e. plants that people cultivate for nutritional or technical purposes, in particular, for industrial purposes. The invention preferably relates to plants cells from fibre-forming plants (e.g. flax, hemp, cotton), oil-storing plants (e.g. rape, sunflower, soy bean), sugar-storing plants (e.g. sugar beat, sugar cane, sugar millet, banana) and protein-storing plants (e.g. leguminoses).

In another embodiment, the invention relates to plant cells from forage plants (e.g. forage grass and pasture grass (alfalfa, clover, etc.)), vegetable plants (e.g. tomato, lettuce, chicory).

In a preferred embodiment, the invention relates to plant cells from starch-storing plants (e.g. wheat, barley, oat, rye, potato, maize, rice, pea, cassava, mung bean). Plant cells from maize, rice, wheat and potato plants are particularly preferred.

Moreover, the present invention relates to a method for producing a branching enzyme from bacteria of the genus *Neisseria*. In said method, the host cells of the invention are cultivated under conditions allowing the protein to be expressed and the protein is recovered from the culture, i.e. from the cells and/or the culture medium. Preferably, a host organism that secretes the branching enzyme is used.

Furthermore, the present invention relates to a method for producing a branching enzyme from bacteria of the genus *Neisseria* with the protein being produced in an in-vitro transcription and translation system using a nucleic acid molecule of the invention. The person skilled in the art is familiar with such systems.

The invention also relates to proteins which are encoded by the nucleic acid molecules of the invention or which are obtainable by a method of the invention.

Furthermore, the present invention relates to antibodies which specifically recognise a protein of the invention. These antibodies may be, for instance, monoclonal or polyclonal antibodies. They may also be fragments of antibodies which recognise the proteins of the invention. The person skilled in the art is familiar with methods for producing said antibodies or fragments.

Furthermore, the present invention relates to the use of a branching enzyme of the invention for the production of α-1,6-branched α-1,4-glucans in in-vitro systems.

In particular, the present invention also relates to transgenic plant cells which contain the nucleic acid molecules or vectors of the invention. Preferably, the cells of the invention are characterised in that the nucleic acid molecule of the invention which has been introduced is stably integrated into the genome and is controlled by a promoter active in plant cells.

There is a plurality of promoters or regulatory elements at disposal for expressing a nucleic acid molecule of the invention in plant cells. In principle, all promoters, enhancers, terminators, etc. that are active in plants are regulatory elements for the expression in plant cells. Basically any promoter which is functional in the plants selected for the transformation can be used. With regard to the plant species used, the promoter can be homologous or heterologous. Said promoter may be selected in such a way that the expression takes place in a constitutive manner or only in a particular tissue, at a certain time in the development of the plant or at a time that is determined by external influence. Examples of suitable promoters are the 35S promoter of the cauliflower mosaic virus (Odell et al., Nature 313 (1985), 810-812 or U.S. Pat. No. 5,352,605), which ensures a constitutive expression in all tissues of a plant, and the promoter construct described in WO/9401571. The ubiquitin promoter (cf. e.g. U.S. Pat. No. 5,614,399) and the promoters of the polyubiquitin genes from maize (Christensen et al., loc. cit.) are further examples. However, also promoters which are only activated at a time determined by external influence (cf. e.g. WO/9307279) can be used. Promoters of heat shock proteins allowing a simple induction may be of particular interest. Furthermore, promoters can be used which lead to the expression of downstream sequences in a certain tissue of the plant, e.g. in photosynthetically active tissue. Examples thereof are the ST-LS1 promoter (Stockhaus et al., Proc. Natl. Acad. Sci. USA 84 (1987), 7943-7947; Stockhaus et al., EMBO J. 8 (1989), 2445-2451), the Ca/b promoter (cf. e.g. U.S. Pat. No. 5,656, 496, U.S. Pat. No. 5,639,952, Bansal et al., Proc. Natl. Acad. Sci. USA 89 (1992), 3654-3658) and the Rubisco SSU promoter (cf. e.g. U.S. Pat. No. 5,034,322 and U.S. Pat. No. 4,962,028). In addition, promoters that are active in the starch-storing organs of plants to be transformed are to be mentioned. It is, for instance, the maize kernels in maize, whereas in potatoes, it is the tubers. For over-expressing the nucleic acid molecules of the invention in potato, the tuber-specific patatin gene promoter B33 (Rocha-Sosa et al., EMBO J. 8 (1989), 23-29) can, for example, be used. Seed-specific promoters have already been described for various plant species. The USP promoter from *Vicia faba*, which guarantees a seed-specific expression in *V. faba* and other plants (Fiedler et al., Plant Mol. Biol. 22 (1993), 669-679; Bäumlein et al., Mol. Gen. Genet. 225 (1991), 459-467) is an example thereof.

Moreover, fruit-specific promoters as described in WO 91/01373 can also be used. Promoters for an endosperm-specific expression, such as the glutelin promoter (Leisy et al., Plant Mol. Biol. 14 (1990), 41-50; Zheng et al., Plant J. 4 (1993), 357-366), the HMG promoter from wheat, the USP promoter, the phaseolin promoter or promoters of zein genes from maize (Pedersen et al., Cell 29 (1982), 1015-1026; Quatroccio et al., Plant Mol. Biol. 15 (1990), 81-93) are particularly preferred. By means of endosperm-specific promoters it is possible to increase the amounts of transcripts of the nucleic acid molecules of the invention in the endosperm in comparison with the endosperm of corresponding wild type plants.

The shrunken-1-promoter (sh-1) from maize (Werr et al., EMBO J. 4 (1985), 1373-1380) is particularly preferred.

In addition, there may be a terminator sequence which is responsible for the correct termination of the transcription and the addition of a poly-A tail to the transcript having the function of stabilising the transcripts. Such elements have been described in the literature (cf. e.g. Gielen et al., EMBO J. 8 (1989), 23-29) and may be exchanged at will.

Therefore, it is possible to express the nucleic acid molecules of the invention in plant cells.

Thus, the present invention also relates to a method for producing transgenic plant cells comprising introducing a nucleic acid molecule or a vector of the invention into plant cells. The person skilled in the art has various plant transformation systems at disposal, e.g. the use of T-DNA for transforming plant cells has been examined extensively and has been described in EP-A-120 516; Hoekema: The Binary Plant Vector System, Offsetdrukkerij Kanters B. V., Alblasserdam (1985), Chapter V, Fraley, Crit. Rev. Plant. Sci., 4, 1-46 and An, EMBO J. 4 (1985), 277-287.

For transferring the DNA in the plant cells, plant explants may suitably be co-cultivated with *Agrobacterium tumefaciens* or *Agrobacterium rhizogenes*. Whole plants may then be regenerated from the infected plant material (e.g. parts of leaves, stem segments, roots and protoplasts or plant cells cultivated in suspensions) in a suitable medium which can contain antibiotics or biocides for selecting transformed cells. The plants obtained in that way can then be examined for the presence of the DNA introduced. Other possibilities of introducing foreign DNA using the biolistic method or by protoplast transformation are known (cf. Willmitzer, L. 1993 Transgenic plants. In: Biotechnology, A Multi-Volume Comprehensive Treatise (H. J. Rehm, G. Reed, A. Pühler, P. Stadler, eds.), Vol. 2, 627-659, VCH Weinheim-New York-Basel-Cambridge).

Alternative systems for transforming monocotyledonous plants are the transformation by means of the biolistic method, the electrically or chemically induced DNA absorption in protoplasts, the electroporation of partially permeabilised cells, the microinjection of DNA in the inflorescence, the microinjection of DNA in microspores and pro-embryos, the DNA absorption through germinating pollens and the DNA absorption in embryos by swelling (cf. e.g. Lusardi, Plant J. 5 (1994), 571-582; Paszowski, Biotechnology 24 (1992), 387-392).

While the transformation of dicotyledonous plants via Ti-plasmid vector systems by means of *Agrobacterium tumefaciens* is well established, more recent studies point to the fact that monocotyledonous plants, too, can indeed be transformed by means of vectors based on *Agrobacterium* (Chan, Plant Mol. Biol. 22 (1993), 491-506; Hiei, Plant J. 6 (1994), 271-282; Bytebier, Proc. Natl. Acad. Sci. USA 84 (1987), 5345-5349; Raineri, Bio/Technology 8 (1990), 33-38; Gould, Plant Physiol. 95 (1991), 426-434; Mooney, Plant, Cell Tiss. & Org. Cult. 25 (1991), 209-218; Li, Plant Mol. Biol. 20 (1992), 1037-1048).

In the past, three of the above transformation systems could be established for various cereals: the electroporation of tissue, the transformation of protoplasts and the DNA transfer by particle bombardment in regenerable tissue and cells (for an overview see Jane, Euphytica 85 (1995), 35-44). The transformation of wheat has been described several times in the literature (for an overview see Maheshwari, Critical Reviews in Plant Science 14 (2) (1995), 149-178).

In particular, the transformation of maize has been described several times in the literature (cf. e.g. WO 95/06128, EP 0513849, EO 0465875, EP 292435; Fromm et al., Biotechnology 8 (1990), 833-844; Gordon-Kamm et al., Plant Cell 2 (1990), 603-618; Koziel et al., Biotechnology 11 (1993), 194-200; Moroc et al., Theor. Appl. Genet. 80 (1990), 721-726).

The successful transformation of other kinds of cereals has also been described, e.g. for barley (Wan and Lemaux, loc. cit.; Ritala et al., loc. cit.; Krens et al., Nature 296 (1982), 72-74) and for wheat (Nehra et al., Plant J. 5 (1994), 285-297).

For expressing the nucleic acid molecules of the invention in plants it is, in principle, possible for the synthesized protein to be located in any compartment of the plant cell. The coding region must optionally be linked to DNA sequences which guarantee the localisation in the respective compartment in order to achieve localisation in a particular compartment. Such sequences are known (cf. e.g. Braun, EMBO J. 11 (1992), 3219-3227; Sonnewald, Plant J. 1 (1991), 95-106; Rocha-Sosa, EMBO J. 8 (1989), 23-29).

As plastidial signal sequence, for instance, the one of ferrodoxin:NADP+oxidoreductase (FNR) from spinach can be used. Said sequence contains the 5' non-translated region and the flanking transit peptide sequence of the cDNA of the plastidial protein ferrodoxin:NADP+oxidoreductase from spinach (nucleotide −171 to +165; Jansen et al., Current Genetics 13 (1988), 517-522).

Furthermore, the transit peptide of the waxy protein from maize plus the first 34 amino acids of the mature waxy protein (Klösgen et al., Mol. Gen. Genet. 217 (1989), 155-161) may also be used as plastidial signal sequence. In addition, the transit peptide of the waxy protein from maize (cf. above) may also be used without the 34 amino acids of the mature waxy protein.

Moreover, it is also thinkable to use to following plastidial signal sequences: the signal sequence of the ribulose biphosphate carboxylase small subunit (Wolter et al., Proc. Natl. Acad. Sci. USA 85 (1988), 846-850; Nawrath et al., Proc. Natl. Acad. Sci. USA 91 (1994), 12760-12764); the signal sequence of the NADP malate dehydrogenase (Gallardo et al., Planta 197 (1995), 324-332); the signal sequence of the glutathione reductase (Creissen et al., Plant J. 8 (1995), 167-175).

Therefore, the present invention also relates to transgenic plant cells that were transformed with one or more of the nucleic acid molecule(s) of the invention, as well as to transgenic plant cells that are derived from cells transformed in such a way. Such cells contain one or more nucleic acid molecule(s) of the invention with said molecule(s) preferably being linked to regulatory DNA elements which guarantee the transcription in plant cells, in particular with a promoter. Such cells can be differentiated from naturally-occurring plant cells in that they contain at least one nucleic acid molecule of the invention.

The transgenic plant cells may be regenerated to whole plants using techniques well-known to the person skilled in the art. The plants obtainable by means of regeneration of the transgenic plant cells of the invention are also a subject matter of the present invention.

Moreover, plants containing the aforementioned plant cells are a subject matter of the present invention. The plants of the invention may, in principle, be plants of any plant species, i.e. both monocotyledonous and dicotyledonous plants. They are preferred to be useful plants, i.e. plants which are cultivated for nutritional or technical, in particular, industrial purposes. Preferably, the invention relates to plant cells from fibre-forming plants (e.g. flax, hemp, cotton), oil-storing plants (e.g. rape, sunflower, soy bean), sugar-storing plants (e.g. sugar beat, sugar cane, sugar millet, banana) and protein-storing plants (e.g. leguminoses).

In another embodiment, the invention relates to forage plants (e.g. forage grass and pasture grass (alfalfa, clover, etc.)), vegetable plants (e.g. tomato, lettuce, chicory).

In a preferred embodiment, the invention relates to starch-storing plants (e.g. wheat, barley, oat, rye, potato, maize, rice, pea, cassava, mung bean), plant cells from maize, rice, wheat and potato plants are particularly preferred.

In a preferred embodiment, the cells of the plants of the invention have an increased activity of the protein of the invention in comparison with corresponding plant cells of wild type plants that have not been genetically modified. These are preferably cells of starch-storing tissue, in particular cells of tubers or of the endosperm, most preferably cells of potato tubers or the endosperm of maize, wheat or rice plants.

Within the meaning of the present invention, the term "increase of the activity" means an increase in the expression of a nucleic acid molecule of the invention which encodes a protein with branching enzyme activity, an increase in the amount of protein with branching enzyme activity and/or an increase in the activity of a protein with branching enzyme activity in the plants.

The increase in the expression can, for instance, be determined by measuring the amount of transcripts coding for said proteins, e.g. by means of Northern blot analysis or RT-PCR. In this context, the term "increase" preferably means an increase in the amount of transcripts by at least 10%, preferably by at least 20%, more preferably by at least 50% and most preferably by at least 75% in comparison with plant cells that have not been genetically modified.

The amount of proteins with branching enzyme activity may, for example, be determined by Western blot analysis. In this context, the term "increase" preferably means that the amount of proteins with branching enzyme activity is increased by at least 10%, preferably by at least 20%, more preferably by at least 50% and most preferably by at least 75% in comparison with corresponding cells that have not been genetically modified.

An increase in the activity of the branching enzyme can, for instance, be determined according to the method described in Lloyd et al. (Biochem. J. 338 (1999), 515-521). In this context, the term "increase" preferably means that the branching enzyme activity is increased by at least 10%, preferably by at least 20%, more preferably by at least 50% and most preferably by at least 75%.

Surprisingly, it was found that plants containing plant cells of the invention with an increased activity of a branching enzyme synthesize a modified starch compared to corresponding wild type plants that have not been genetically modified. The modified starch may, for instance, be modified with regard to its physio-chemical properties, in particular the amylose/amylopectin ratio, the branching degree, the average chain length, the phosphate content, the viscosity, the size of the starch granule, the distribution of the side-chains and/or the form of the starch granule in comparison with starch synthesized in wild type plants. As a consequence, this modified starch is more suitable for particular purposes.

Furthermore, it was surprisingly found that in plant cells in which the activity of the branching enzyme of the invention is increased, the composition of the starch is modified in such a way that it has a higher gel texture and/or a reduced phosphate content and/or a reduced peak viscosity and/or a reduced pastification temperature and/or a reduced size of the starch granule and/or a modified distribution of the side-chains in comparison with starch from corresponding wild type plants.

In this context, the term "increased gel texture" means an increase by at least 10%, preferably by at least 50%, more preferably by at least 100%, by at least 200% and most preferably by at least 300% in comparison with the gel texture of starch from wild type plants. The gel texture is determined as described below.

Within the meaning of the present invention, the term "reduced phosphate content" means that the overall content of covalently bound phosphate and/or the content of phosphate in the C-6 position of the starch synthesized in the plant cells of the invention is reduced by at least 20%, preferably by at least 40%, more preferably by at least 60% and most preferably by at least 80% in comparison with the starch from plant cells of corresponding wild type plants.

The overall phosphate content or the content of phosphate in the C-6 position may be determined according to the method as described below.

Within the meaning of the present invention, the term "reduced peak viscosity" means that the peak viscosity is reduced by at least 10%, preferably by at least 25%, more preferably by at least 50% and most preferably by at least 75% in comparison with the peak viscosity of starches from wild type plants.

Within the meaning of the present invention, the term "reduced pastification temperature" means that the pastification temperature is reduced by at least 0.5° C., preferably by at least 1.0° C., more preferably by at least 2.0° C., most preferably by at least 3.0° C. in comparison with the pastification temperature of starches from wild type plants.

The peak viscosity and the pastification temperature can be determined with a Rapid Visco Analyzer in the manner described below.

The skilled person is familiar with the terms "peak viscosity" and "pastification temperature".

The term "reduced size of the starch granule" means that the percentage proportion of the starch granules having a size of up to 15 μm is increased by at least 10%, preferably by at least 30%, more preferably by at least 50%, 100% and most preferably by at least 150% in comparison with wild type plants.

The size of the starch granules is determined by means of a photosedimentometer of the type "Lumosed" by Retsch, GmbH, Germany in the manner described below.

In this context, the term "modified distribution of the side-chains" means that the proportion of side-chains with a DP of 6 to 9 is increased by at least 25%, preferably by at least 50%, more preferably by at least 100% and most preferably by at least 200% in comparison with the proportion of side-chains with a DP of 6 to 9 of amylopectin from wild type plants.

In another embodiment of the invention, the term a "modified distribution of side-chains" means that the proportion of side-chains with a DP of 6 to 8, preferably of 6 to 7 is increased by at least 25%, preferably by at least 50%, more preferably by at least 100% and most preferably by at least 200% in comparison to the proportion of side-chains with the corresponding degree of polymerization of amylopectin from wild type plants.

The proportion of side chains is established by determining the percentage proportion of a particular side-chain with regard to the overall share of all side-chains. The overall share of all side-chains is established by determining the overall area below the peaks which represent the polymerization degrees of DP 6 to 30 in the HPLC chromatograph. The percentage proportion of a particular side-chain with regard to the overall share of all side-chains is established by determining the ratio of the area below the peak that represents said side-chain in the HPLC chromatograph to the overall area. Preferably, the program AI-450, version 3.31 by Dionex, USA, is used.

In another embodiment, the present invention relates to a starch the amylopectin of which has side-chains with a DP of 5 compared to the amylopectin of starches of wild type plants.

Furthermore, the present invention relates to a method for producing a transgenic plant which synthesizes a modified starch, wherein
(a) a plant cell is genetically modified by introducing a nucleic acid molecule of the invention and/or a vector of the invention the presence or expression of which leads to an increase in the activity of a protein having the activity of a branching enzyme;
(b) a plant is regenerated from the cell produced according to step (a); and
(c) optionally further plants are produced from the plant produced according to step (c).

In a preferred embodiment of the method, the starch is modified in such a way that it has an increased gel texture and/or a reduced phosphate content and/or a reduced peak viscosity and/or a reduced pastification temperature and/or a reduced size of the starch granules and/or a modified distribution of the side-chains compared to the starch of corresponding wild type plants.

In this context, the terms "increased gel texture", "reduced phosphate content", "reduced peak viscosity", "reduced pastification temperature", "reduced size of the starch granules" and "modified distribution of the side-chains" are defined as above.

As regards the genetic modification introduced according to step (a), the same applies as has been explained in a different context with regard to the plants of the invention.

The regeneration of plants according to step (b) can be achieved by methods known to the skilled person.

Further plants according to step (b) of the method of the invention may, for instance, be produced by vegetative propagation (e.g. by means of cuttings, tubers or through callus culture and regeneration of whole plants) or by sexual reproduction. Preferably, the sexual reproduction is controlled, i.e. selected plants having particular properties are cross-bred and propagated.

The present invention also relates to the plants obtainable by the method of the invention.

The present invention also relates to propagation material of plants of the invention as well as of the transgenic plants produced according to the method of the invention. In this context, the term "propagation material" comprises those components of the plant that are suitable for producing progenies in a vegetative or generative way are, for example, cuttings, callus cultures, rhizomes or tubers are suitable for the vegetative propagation. Other propagation material comprises, for example, fruit, seeds, seedlings, protoplasts, cell cultures, etc. The propagation material is preferred to be tubers and seeds.

Starch obtainable from the transgenic plant cells and plants of the invention as well as from the propagation material is a further subject matter of the invention.

Due to the expression of a nucleic acid molecule of the invention or of a vector of the invention, the presence of expression of which leads to an increase in the activity of a branching enzyme compared to plant cells of wild type plants that have not been genetically modified, the transgenic plant cells and plants of the invention synthesize a starch which is modified with regard to its physio-chemical properties, in particular with regard to gel texture and/or pastification behaviour and/or the size of the starch granule and/or the phosphate content and/or the distribution of the side-chains in comparison with starch synthesized in wild type plants.

Moreover, the present invention also relates to starches characterised in that they have an increased gel texture and/or a reduced phosphate content and/or a reduced peak viscosity and/or a reduced pastification temperature and/or a reduced sized of the starch granules and/or a modified distribution of the side-chains.

In a particularly preferred embodiment, the present invention relates to potato starches.

In this context, the terms "increased gel texture", "reduced phosphate content", "reduced peak viscosity", "reduced pastification temperature", "reduced size of the starch granules" and "modified distribution of the side-chains" are defined as above.

In addition, the present invention relates to a method for producing a modified starch comprising the step of extracting the starch from a plant (cell) of the invention as described above and/or from starch-storing parts of such a plant. Preferably, such a method also comprises the step of harvesting the cultivated plants and/or the starch-storing parts of said plants before the starch is extracted and, more preferably, also the step of cultivating plants of the invention prior to harvesting them. The skilled person is familiar with methods for extracting the starch of plants or of starch-storing parts of plants. Furthermore, methods for extracting the starch from various starch-storing plants have been described, e.g. in "Starch: Chemistry and Technology (ed.: Whistler, BeMiller and Paschall (1994), $2^{nd}$ edition, Academic Press Inc. London Ltd.; ISBN 0-12-746270-8; cf. e.g. chapter XII, page 412-

468: Maize and *Sorghum* Starches: Production; by Watson; chapter XIII, page 469-479; Tapioca, Arrow Root and Sago Starches: Production; by Corbishley and Miller; chapter XIV, page 479-490: Potato Starch: Production and Applications; by Mitch; chapter XV, page 491 to 506: Wheat Starch Production, Modification and Applications; by Knight and Oson; and chapter XVI, page 507-528: Rice Starch: Production and Applications; by Rohmer and Klem; Maize Starch: Eckhoff et al., Cereal Chem. 73 (1996), 54-57, the extraction of maize starch on an industrial scale is usually achieved by means of the so-called wet milling)). Appliances that are usually used for methods for extracting starch from plant material include separators, decanters, hydrocyclones, spray dryers and fluid-bed dryers.

Starch obtainable by the method described above is also a subject matter of the present invention.

The starches of the invention can be modified according to methods known to the person skilled in the art and are suitable for various applications in the foodstuff or non-foodstuff industry in an unmodified or modified form.

In principle, possibilities of use can be divided into two large areas. One area comprises hydrolysis products of the starch, mainly glucose and glucan building blocks obtained via enzymatic or chemical methods. They serve as starting material for further chemical modifications and processes such as fermentation. For a reduction of costs the simplicity and inexpensive carrying out of a hydrolysis method can be of importance. At present, the method is essentially enzymatic with use of amyloglucosidase. It would be possible to save costs by reducing use of enzymes. This could be achieved by changing the structure of the starch, e.g. surface enlargement of the granule, easier digestibility due to low branching degree or a steric structure limiting the accessibility for the enzymes used.

The other area where starch is used as so-called native starch due to its polymeric structure can be subdivided into two further fields of application:

1. Use in Foodstuffs

Starch is a classic additive for various foodstuffs, in which it essentially serves the purpose of binding aqueous additives and/or causes an increased viscosity or an increased gel formation. Important characteristic properties are flowing and sorption behaviour, swelling and pastification temperature, viscosity and thickening performance, solubility of the starch, transparency and paste structure, heat, shear and acid resistance, tendency to retrogradation, capability of film formation, resistance to freezing/thawing, digestibility as well as the capability of complex formation with e.g. inorganic or organic ions.

2. Use in Non-Foodstuffs

The other major field of application is the use of starch as an adjuvant in various production processes or as an additive in technical products. The major fields of application for the use of starch as an adjuvant are, first of all, the paper and cardboard industry. In this field, the starch is mainly used for retention (holding back solids), for sizing filler and fine particles, as solidifying substance and for dehydration. In addition, the advantageous properties of starch with regard to stiffness, hardness, sound, grip, gloss, smoothness, tear strength as well as the surfaces are utilized.

2.1 Paper and Cardboard Industry

Within the paper production process, a differentiation can be made between four fields of application, namely surface, coating, mass and spraying.

The requirements on starch with regard to surface treatment are essentially a high degree of brightness, corresponding viscosity, high viscosity stability, good film formation as well as low formation of dust. When used in coating the solid content, a corresponding viscosity, a high capability to bind as well as a high pigment affinity play an important role. As an additive to the mass rapid, uniform, loss-free dispersion, high mechanical stability and complete retention in the paper pulp are of importance. When using the starch in spraying, corresponding content of solids, high viscosity as well as high capability to bind are also significant.

2.2 Adhesive Industry

A major field of application is, for instance, in the adhesive industry, where the fields of application are subdivided into four areas: the use as pure starch glue, the use in starch glues prepared with special chemicals, the use of starch as an additive to synthetic resins and polymer dispersions as well as the use of starches as extenders for synthetic adhesives. 90% of all starch-based adhesives are used in the production of corrugated board, paper sacks and bags, composite materials for paper and aluminum, boxes and wetting glue for envelopes, stamps, etc.

2.3 Textiles and Textile Care Products

Another possible use as adjuvant and additive is in the production of textiles and textile care products. Within the textile industry, a differentiation can be made between the following four fields of application: the use of starch as a sizing agent, i.e. as an adjuvant for smoothing and strengthening the burring behaviour for the protection against tensile forces active in weaving as well as for the increase of wear resistance during weaving, as an agent for textile improvement mainly after quality-deteriorating pretreatments, such as bleaching, dying, etc., as thickener in the production of dye pastes for the prevention of dye diffusion and as an additive for warping agents for sewing yarns.

2.4 Building Industry

Furthermore, starch may be used as an additive in building materials. One example is the production of gypsum plaster boards, in which the starch mixed in the thin plaster pastifies with the water, diffuses at the surface of the gypsum board and thus binds the cardboard to the board. Other fields of application are admixing it to plaster and mineral fibers. In ready-mixed concrete, starch may be used for the deceleration of the sizing process.

2.5 Ground Stabilisation

Furthermore, the starch is advantageous for the production of means for ground stabilisation used for the temporary protection of ground particles against water in artificial earth shifting. According to state-of-the-art knowledge, combination products consisting of starch and polymer emulsions can be considered to have the same erosion- and encrustation-reducing effect as the products used so far; however, they are considerably less expensive.

2.6 Use in Plant Protectives and Fertilizers

Another field of application is the use of starch in plant protectives for the modification of the specific properties of these preparations. For instance, starch is used for improving the wetting of plant protectives and fertilizers, for the dosed release of the active ingredients, for the conversion of liquid, volatile and/or odorous active ingredients into microcristalline, stable, deformable substances, for mixing incompatible compositions and for the prolongation of the duration of the effect due to a reduced disintegration.

2.7 Drugs, Medicine and Cosmetics Industry

Starch may also be used in the fields of drugs, medicine and in the cosmetics industry. In the pharmaceutical industry, starch may be used as a binder for tablets or for the dilution of the binder in capsules. Furthermore, starch is suitable as disintegrant for tablets since, upon swallowing, it absorbs fluid and after a short time it swells so much that the active ingredient is released. For qualitative reasons, medical lubricating and vulnerary dusting powders are further fields of application. In the field of cosmetics, the starch may for example be used as a carrier of powder additives, such as scents and salicylic acid. A relatively extensive field of application for the starch is toothpaste.

2.8 Starch as an Additive in Coal and Briquettes

Starch can also be used as an additive in coal and briquettes. By adding starch, coal can be quantitatively agglomerated and/or briquetted in high quality, thus preventing premature disintegration of the briquettes. Barbecue coal contains between 4 and 6% added starch, calorated coal between 0.1 and 0.5%. Furthermore, starch is suitable as a binding agent since adding it to coal and briquette can considerably reduce the emission of toxic substances.

2.9 Processing of Ore and Coal Slurry

Furthermore, starch may be used as a flocculant in the processing of ore and coal slurry.

2.10 Additive for Casting Materials

Another field of application is the use as an additive to process materials in casting. For various casting processes cores produced from sands mixed with binding agents are needed. Nowadays, the most commonly used binding agent is bentonite mixed with modified starches, mostly swelling starches.

The purpose of adding starch is increased flow resistance as well as improved binding strength. Moreover, swelling starches may fulfil more prerequisites for the production process, such as dispersability in cold water, rehydratisability, good mixability in sand and high capability of binding water.

2.11 Rubber Industry

In the rubber industry starch may be used for improving the technical and optical quality. Reasons for this are improved surface gloss, grip and appearance. For this purpose, starch is dispersed on the sticky rubberised surfaces of rubber substances before the cold vulcanization. It may also be used for improving the printability of rubber.

2.12 Production of Leather Substitutes

Another field of application for modified starch is the production of leather substitutes.

2.13 Starch in Synthetic Polymers

In the plastics market the following fields of application are emerging: the integration of products derived from starch into the processing process (starch is only a filler, there is no direct bond between synthetic polymer and starch) or, alternatively, the integration of products derived from starch into the production of polymers (starch and polymer form a stable bond).

The use of the starch as a pure filler cannot compete with other substances such as talcum. This situation is different when the specific starch properties become effective and the property profile of the end products is thus clearly changed. One example is the use of starch products in the processing of thermoplastic materials, such as polyethylene. Thereby, starch and the synthetic polymer are combined in a ratio of 1:1 by means of coexpression to form a 'master batch', from which various products are produced by means of common techniques using granulated polyethylene. The integration of starch in polyethylene films may cause an increased substance permeability in hollow bodies, improved water vapor permeability, improved antistatic behaviour, improved anti-block behaviour as well as improved printability with aqueous dyes.

Another possibility is the use of the starch in polyurethane foams. Due to the adaptation of starch derivatives as well as due to the optimisation of processing techniques, it is possible to specifically control the reaction between synthetic polymers and the hydroxy groups of the starch. The results are polyurethane films having the following property profiles due to the use of starch: a reduced coefficient of thermal expansion, decreased shrinking behaviour, improved pressure/tension behaviour, increased water vapour permeability without a change in water acceptance, reduced flammability and cracking density, no drop off of combustible parts, no halides and reduced aging. Disadvantages that presently still exist are reduced pressure and impact strength.

Product development of film is not the only option. Also solid plastics products, such as pots, plates and bowls can be produced by means of a starch content of more than 50%. Furthermore, the starch/polymer mixtures offer the advantage that they are much easier biodegradable.

Furthermore, due to their extreme capability to bind water, starch graft polymers have gained utmost importance. These are products having a backbone of starch and a side lattice of a synthetic monomer grafted on according to the principle of radical chain mechanism. The starch graft polymers available nowadays are characterised by an improved binding and retaining capability of up to 1000 g water per g starch at a high viscosity. These super absorbers are used mainly in the hygiene field, e.g. in products such as nappies and sheets, as well as in the agricultural sector, e.g. in seed pellets.

What is decisive for the use of the novel starch modified by recombinant DNA techniques are, on the one hand, structure, water content, protein content, lipid content, fibre content, ashes/phosphate content, amylose/amylopectin ratio, distribution of the relative molar mass, branching degree, granule size and shape as well as crystallization, and on the other hand, the properties resulting in the following features: flow and sorption behaviour, pastification temperature, viscosity, thickening performance, solubility, paste structure, transparency, heat, shear and acid resistance, tendency to retrogradation, capability of gel formation, resistance to freezing/thawing, capability of complex formation, iodine binding, film formation, adhesive strength, enzyme stability, digestibility and reactivity.

The production of modified starch by genetically operating with a transgenic plant may modify the properties of the starch obtained from the plant in such a way as to render further modifications by means of chemical or physical methods superfluous. On the other hand, the starches modified by means of recombinant DNA techniques might be subjected to further chemical modification, which will result in further improvement of the quality for certain of the above-described fields of application. These chemical modifications are principally known. These are particularly modifications by means of heat treatment
    acid treatment
    formation of starch ethers
    starch alkyl ether, O-allyl ether, hydroxylalkyl ether, O-carboxylmethyl ether, N-containing starch ethers, P-containing starch ethers and S-containing starch ethers.
    formation of branched starches
    formation of starch graft polymers.
    oxidation and
    esterification
    leading to the formation of phosphate, nitrate, sulfate, xanthate, acetate and citrate starches. Other organic acids may also be used for the esterification.

In another embodiment, the present invention relates to parts of plants of the invention that can be harvested, e.g. fruit, storage roots, roots, blossoms, buds, sprouts or stems, preferably seeds or tubers with said parts that can be harvested containing plants cells of the invention.

In another aspect, the present invention relates to a regulatory region which naturally controls, in bacterial cells, the transcription of an above-described nucleic acid molecule of the invention encoding a branching enzyme from bacteria of the genus *Neisseria*.

Within the meaning of the present invention, the term "regulatory region" relates to a region that influences the specificity and/or the extent of the expression of a gene sequence, e.g. in such a way that the expression takes place in response to certain external stimuli or at a certain time. Such regulatory regions usually are located in a region that is called promoter. Within the meaning of the present invention, the term "promoter" comprises nucleotide sequences that are necessary for initiating the transcription, i.e. for binding the RNA polymerase, and may also comprise the TATA box(es).

In a preferred embodiment, the regulatory region of the invention comprises a nucleotide sequence selected from the group consisting of:
(a) nucleotide sequences comprising the nucleotides 1 to 169 of the nucleotide sequence depicted in SEQ ID NO. 1;
(b) the nucleotide sequence of the regulatory region contained in the insert of the plasmid DSM 12425 or parts thereof; and
(c) nucleotide sequences hybridizing with the sequences of (a) or (b) under stringent conditions.

The nucleotides 1 to 169 of the sequence depicted in SEQ ID NO. 1 form part of the regulatory region of the gene of the branching enzyme from *Neisseria denitrificans*. Putative promoter sequences are located at the positions 36 to 44, 51 to 55 and 157 to 162, wherein the sequence "GGGAGA" possibly is a Shine-Dalgarno sequence.

The present invention also relates to regulatory regions having a homology to the aforementioned regulatory regions that is so high that they hybridize to at least one of said regions, preferably under stringent conditions. Regulatory regions that have a sequence identity of at least 80%, preferably of at least 90% and most preferably of at least 95% to any of the aforementioned regulatory regions, in particular to the one depicted in SEQ ID NO. 1, are particularly preferred.

They also comprise regulatory regions which are modified with regard to the above-described regulatory regions, for instance due to deletion(s), insertion(s), substitution(s), addition(s) and/or recombination(s) and/or modification(s).

The skilled person is familiar with methods for introducing such modifications into the regulatory regions. Moreover, the person skilled in the art knows that the regulatory regions of the invention may be coupled with further elements which influence the transcription in bacterial cells, e.g. with enhancer elements.

The present invention also relates to recombinant DNA molecules comprising a regulatory region of the invention.

In such a recombinant DNA molecule, the regulatory region is preferred to be linked to a heterologous DNA sequence. In this context, the term "heterologous" means that said sequence is naturally not linked to the regulatory region. In addition, a recombinant DNA molecule of the invention may contain further regulatory elements which are of importance as regards transcription and/or translation in bacterial cells, e.g. transcription or translation enhancers.

Moreover, the present invention relates to host cells that are transformed with a regulatory region, a recombinant DNA molecule or a vector of the invention.

Furthermore, the present invention relates to vectors containing a regulatory region of the invention or a recombinant DNA molecule of the invention. Said vectors comprise, for instance, also plasmids, cosmids, bacteriophages, viruses, etc. which usually are used for methods in molecular genetics.

In addition, the invention relates to an in-vitro method for producing α-1,6-branched α-1,4-glucans using the substrate sucrose and an enzyme combination of an amylosucrase and a branching enzyme. Within the meaning of the present invention, the term "in-vitro method" relates to a conversion, i.e. a reaction, which takes place outside the living organism. In particular, the term "in vitro" means that the method of the invention takes place in a reaction vessel. Most preferably, the term "in vitro" means that the reaction takes place in absence of living cells.

The advantage of the method of the invention is that it is possible to control the branching degree and that it is possible, by means of said control, to adapt the properties of the glucans synthesized to the planned use of the glucans. Thus, as regards the application as capsulation material in pharmaceutics, there is the possibility of optimising the release rate of pharmaceutical agents by purposefully adjusting the branching degree.

Within the meaning of the present invention, an amylosucrase (sucrose:1,4-α-D-glucan 4-α-glucosyltransferase, E.C. 2.4.1.4) is an enzyme which catalyses the conversion of sucrose to water-insoluble α-1,4-glucans and fructose. For said enzyme, the following reaction scheme is suggested:

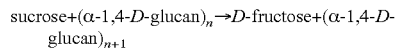

This is a transglycosylation reaction. The products of said reaction are water-insoluble α-1,4-glucans and fructose. The transglycosylation may take place in the absence or in the presence of acceptor molecules. Such acceptor molecules may be, for instance, polysaccharides like malto-oligosaccharides, dextrin or glycogen. If said acceptor molecule is a linear, oligomeric α-1,4-glucan, the product resulting from the transglycosylation reaction by means of the amylosucrase is a polymeric linear α-1,4-glucan. If the transglycosylation reaction by means of amylosucrase is carried out without any acceptor molecules, a glucan having a terminal fructose molecule is obtained. Within the meaning of the present invention, all products obtained by means of an amylosucrase in the absence or in the presence of acceptor molecules are called α-1,4-glucans.

For the reaction mechanism of a transglycosylation by means of an amylosucrase in the absence of an acceptor molecule, the following reaction scheme is suggested:

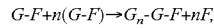

wherein G-F is sucrose, G is glucose, F is fructose and $G_n$-G-F is an α-1,4-glucan.

For the reaction mechanism of a transglycosylation by means of amylosucrase in the presence of an acceptor molecule, the following reaction scheme is suggested:

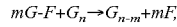

wherein $G_n$ is a polysaccharide acceptor molecule, $G_{n-m}$ is a polysaccharide consisting of an acceptor plus an α-1,4-glucan chain synthesized thereto, G-F is sucrose, F is fructose and G is glucose.

No co-factors are necessary for the transglycosylation by means of an amylosucrase.

In principle, all amylosucrases which catalyse the synthesis of linear α-1,4-glucans starting from sucrose are suitable for carrying out the method of the invention.

Up to now, amylosucrases from several bacteria species have been known, in particular mainly from *Neisseria* species (MacKenzie et al., Can. J. Microbiol. 24 (1978), 357-362).

Thus, an amylosucrase of prokaryotic origin is preferred to be used. Amylosucrases have been known, for example, from *Neisseria perflava* (Okada and Hehre, J. Biol. Chem. 249 (1974), 126-135; MacKenzie et al., Can. J. Microbiol. 23 (1977), 1303-1307) or from *Neisseria canis, Neisseria cinerea, Neisseria denitrificans, Neisseria sicca* and *Neisseria subflava* (MacKenzie et al., Can. J. Microbiol. 24 (1978), 357-362). Furthermore, WO 95/31553 describes an amylosucrase from *Neisseria polysaccharea*. An amylosucrase that is naturally secreted by a prokaryote is preferred to be used.

In a preferred embodiment of the invention, an amylosucrase from *Neisseria polysaccharea* is used.

The enzyme that is expressed in *Neisseria polysaccharea* is extremely stable and binds very tight to the polymerization products and is competitively inhibited by the reaction product fructose (MacKenzie et al., Can. J. Microbiol. 23 (1977), 1303-1307). As regards the *Neisseria* species *Neisseria polysaccharea*, the amylosucrase is secreted (Riou et al., Can. J. Microbiol. 32 (1986), 909-911), whereas in other *Neisseria* species, it remains in the cell. An amylosucrase having the amino acid sequence depicted in SEQ ID NO. 5 is particularly preferred to be used.

In another preferred embodiment of the invention, a purified amylosucrase is used.

In this context, a purified amylosucrase is an enzyme which is substantially free of cellular components of the cells in which the protein is synthesized. Preferably, the term "purified amylosucrase" relates to an amylosucrase which has a degree of purity of at least 70%, preferably of at least 85% and most preferably of at least 90%.

The use of a purified protein for producing α-1,4-glucans has various advantages. In contrast to methods using partially purified protein extracts, the reaction medium of the method of the invention does not contain any residues of the production strain (microorganism) that is used to purify the protein or to produce it by means of genetic engineering.

What is more, there are advantages in the food and pharmaceutical industries if the purified protein is used. The components of the product are defined more exactly, too, if the reaction medium is defined and if all unnecessary components have been removed. This leads to a less extensive procedure for marketing authorisation for these products, which have been manufactured by means of biotechnology, in the food and pharmaceutical industry, in particular, since said products are supposed to show no traces of a transgenic microorganism.

Within the meaning of the present invention, a branching enzyme (α-1,4-glucan:α-1,4-glucan 6-glycosyltransferase, E.C. 2.4.1.18) is a protein catalysing a transglycosylation reaction in which the α-1,4-linkings of an α-1,4-glucan donor are hydrolyzed and the released α-1,4-glucan chains are transferred to an α-1,4-glucan acceptor chain and converted into α-1,6-linkings.

In principle, all branching enzymes of any origin (bacterial, fungal, plant, animal) are suitable for carrying out the method of the invention (cf. e.g. Baba et al., Biochem. Biophys. Res. Commun. 181 (1991), 87-94; Kossmann et al., Mol. Gen. Genet. 203 (1991), 237-244; Nakamura and Yamanouchi, Plant Physiol. 99 (1992), 1265-1266; Baecker et al., J. Biol. Chem. 261 (1986), 8738-8743; Kiel et al., Gene (1989), 9-17, etc.).

The person skilled in the art can isolate corresponding genes by means of standard methods of molecular biology, as have been described, amongst others, in Sambrook et al. (Sambrook et al., Molecular Cloning, A Laboratory Manual, $2^{nd}$ edition, Cold Spring Harbor Laboratory Press, NY, USA (1989)).

In a preferred embodiment of the invention, the branching enzyme is a branching enzyme from a prokaryote, preferably from a bacterium of the genus *Neisseria*, more preferably from *Neisseria denitrificans* and most preferably from a branching enzyme of the invention as is described below. A branching enzyme having the amino acid sequence depicted in SEQ ID NO. 1 is particularly preferred.

In another preferred embodiment, the branching enzyme is a purified branching enzyme. In this context, a purified branching enzyme is an enzyme which is substantially free of cellular components of the cells in which the protein is synthesized. Preferably, the term "purified branching enzyme" means that the enzyme has a degree of purity of at least 70%, preferably of at least 85% and most preferably of at least 90%.

Moreover, in the method of the invention, proteins are preferred to be used which have been produced recombinantly. Within the meaning of the present invention, said proteins are proteins which have been produced by introducing a DNA sequence encoding said protein into a host cell and expressing it there. The protein may subsequently be recovered from the host cell and/or the culture medium. The host cell is preferred to be a bacterium or a protist (e.g. fungi, in particular yeasts, algae), such as defined, for example in Schlegel "Allgemeine Mikrobiologie" (Georg Thieme Verlag, 1985, 1-2). In particular, the proteins are preferred to be secreted by the host cell. Such host cells for producing a recombinant protein can be generated using methods that are known to the person skilled in the art.

Methods in Enzymology 153 (1987), 385-516, Bitter et al. (Methods in Enzymology 153 (1987), 516-544; Sawers et al., Applied Microbiology and Biotechnology 46 (1996), 1-9; Billmann-Jacobe, Current Opinion in Biotechnology 7 (1996), 500-504; Hockney, Trends in Biotechnology 12 (1994), 456-463 and Griffiths et al., Methods in Molecular Biology 75 (1997), 427-440 give an overview of different expression systems. Expression vectors have been described extensively in the literature. Apart from a selection marker gene and a replication origin guaranteeing the replication in the selected host, they usually contain a bacterial or a viral promoter, and mostly a termination signal for the transcription. Between the promoter and the termination signal, there is at least one restriction site or a polylinker which allow the insertion of an encoding DNA sequence. The DNA sequence which naturally controls the transcription of the corresponding gene can be used as promoter sequence if it is active in the selected host organism. Said sequence, however, may also be exchanged for other promoter sequences. Both promoters effecting the constitutive expression of the gene and inducible promoters allowing a directed regulation of the expression of the downstream gene can be used. Bacterial and viral promoter sequences having these properties have been described extensively in the literature. Regulatory sequences for the expression in microorganisms (e.g. *E. coli, S. cerevisiae*) have been described sufficiently in the literature. Promoters allowing a particularly strong expression of the downstream gene include, for example, the T7 promoter (Studier et al., Methods in Enzymology 185 (1990), 60-89), lacuv5, trp, trp-lacUV5 (DeBoer et al., in Rodriguez and Chamberlin (eds.) Promoters, Structure and Function; Praeger, N.Y. (1982), 462-481; DeBoer et al., Proc. Natl. Acad. Sci. USA (1983), 21-25), ⊠p1, rac (Boros et al., Gene 42 (1986), 97-100). Normally, the amounts of proteins reach their top level from the middle to about the end of the logarithmic phase of the growth cycle of the microorganisms. Therefore, preferably inducible promoters are used for the synthesis of proteins. These inducible promoters often result in a higher yield of proteins than the constitutive promoters. Due to the constant transcription and translation of a cloned gene, the use of strong constitutive promoters often has the effect that the energy for other essential cell functions is lost and that, thus, the cell growth is slowed down (Bernard R. Glick/Jack J. Pasternak, Molekulare Biotechnologie (1995), Spektrum Akademischer Verlag GmbH, Heidelberg Berlin Oxford, p. 342). Hence, a two-step method is often used to achieve the optimum amount of proteins. First, the host cells are cultivated under optimum conditions until they reach a relatively high cell density. In the second step, the transcription is induced depending on the kind of promoter used. In this context, a tac promoter that is inducible by lactose or IPTG (=isopropyl-β-D-thiogalactopyranoside) is particularly suitable (DeBoer et al., Proc. Natl. Acad. Sci. USA 80 (1983), 21-25). Termination signals for the transcription have also been described in the literature.

The transformation of the host cell with the DNA encoding a corresponding protein DNA can normally be carried out according to standard methods, as described, for instance, in Sambrook et al. (Molecular Cloning: A Laboratory Course Manual, $2^{nd}$ edition (1989), Cold Spring Harbor Press, New York). The host cell is cultivated in culture media which correspond to the needs of the respective host cell. In particular, pH value, temperature, salt concentration, aeration, antibiotics, vitamins and trace elements, etc. are taken into consideration.

The enzyme produced by the host cells can be purified according to standard purification techniques, such as precipitation, ion exchange chromatography, affinity chromatography, gel filtration, HPLC reverse phase chromatography, etc.

By modifying the DNA expressed in the host cells, it is possible to produce a polypeptide in the host cell, which is easier to be isolated from the culture medium due to certain properties. Thus, there is the possibility of expressing the protein to be expressed as a fusion protein together with another polypeptide sequence the specific binding property of which allows the isolation of the fusion protein through affinity chromatography (e.g. Hopp et al., Bio/Technology 6 (1988), 1204-1210; Sassenfeld, Trends Biotechnol. 8 (1990), 88-93).

In a preferred embodiment of the method of the invention, enzymes are used which have been produced recombinantly and which have been secreted by the host cell into the culture medium so that it is not necessary to disrupt cells or to purify the protein any further since the secreted protein may be recovered from the supernatant. Methods known in process engineering, such as dialysis, reverse osmosis, chromatographic methods, etc. may be used for removing residual components of the culture medium. The same applies to the reconcentration of the protein secreted into the culture medium. Normally, the secretion of proteins by microorganisms is mediated by N-terminal signal peptides (signal sequence, leader peptide). Proteins having said signal sequence may pass through the cell membrane of the microorganism. Secretion of proteins may be achieved by linking the DNA sequence that encodes said signal peptide to the corresponding region encoding the enzyme.

A signal peptide that optionally occurs naturally is preferred, e.g. the signal peptide of the amylosucrase from *Neisseria polysaccharea*.

The signal peptide of the α-CGTase from *Klebsiella oxytoca* M5A1 (Fiedler et al., J. Mol. Biol. 256 (1996), 279-291) or a signal peptide as is encoded by the nucleotides 11529-11618 of the sequence accessible in the GenBank under the accession number X86014 is particularly preferred.

As an alternative, the enzymes used in the method of the invention may also have been produced using an in-vitro transcription and translation system which leads to the expression of the proteins without using microorganisms.

In another preferred embodiment, the amylosucrase and/or the branching enzyme are immobilized on a support material.

Immobilizing the enzymes has the advantage that the enzymes can be recovered from the reaction mixture in a simple manner as catalysts of the synthesis reaction and can be used several times. Since the purification of enzymes usually requires much time and money, immobilization and recycling can save costs considerably. The degree of purity of the reaction products which do not contain any remaining proteins is another advantage.

There is a plurality of support materials at disposal for immobilizing proteins wherein the coupling with the support material may take place via covalent or non-covalent bindings (for an overview see: Methods in Enzymology 135, 136, 137). For example, agarose, alginate, cellulose, polyacrylamide, silica or nylon are extensively used as support material.

In another preferred embodiment of the method, a (partially purified) enzyme crude extract of an amylosucrase and/ or a branching enzyme is used. In this context, a crude extract is an amylosucrase and/or branching enzyme preparation having a reduced degree of purity in comparison with a purified enzyme (cf. Examples 5 and 6).

In a preferred embodiment, in the method of the invention the branching degree of the α1,6-branched α-1,4-glucans is modified by changing the ratio of the protein activity of branching enzyme and amylosucrase. In this context, the ratio of the protein activity is the ratio of the protein activities (u) from amylosucrase and branching enzyme. The protein activities may be determined as described in Examples 7 and 8. When the method of the invention is carried out (cf. Example 9), the ratio of protein activity (units of amylosucrase/units of branching enzyme) may range from 1/4000 to 2000/1.

In a preferred embodiment, the ratio of the protein activity ranges from 1/1500 to 1500/1.

In another preferred embodiment, the ratio of the protein activity ranges from 1/800 to 1300/1.

In a particularly preferred embodiment, the ratio of the protein activity ranges from 1/400 to 1200/1.

It is possible to modify the branching degree of the α-1,6-branched α-1,4-glucans obtained from 0.05% to 35% by changing the ratio of the protein activity.

In a preferred embodiment, it is possible to change the branching degree of the α-1,6-branched α-1,4-glucans in 6-position from 0.15% to 25%, more preferably from 0.20% to 15% and most preferably from 0.25% to 12%.

If the method of the invention is used, it is possible, in particular, to produce products having a higher branching degree than glycogen.

Within the meaning of the present invention, the branching degree is the average share of branchings in O-6 position compared to all glucose units linked differently. The branching degree can be determined by methylation analysis (cf. Example 10).

In another preferred embodiment, in the method of the invention, the molecular weight of the products is modified by changing the protein activity ratio. It is, in particular, possible to change the protein activity ratio during the reaction that leads to the synthesis of the α-1,6-branched α-1,4-glucans.

In another preferred embodiment of the method of the invention, the method is to be carried out at different sucrose concentrations. In principle, it is possible for the method to be carried out at a concentration preferably ranging from 1% to 80% sucrose (w/v), more preferably ranging from 5% to 50% and most preferably from 10% to 40%.

In the present invention, the molecular weight is determined by light scattering experiments (Light Scattering from Polymer Solutions, editor: Huglin, M. B., Academic Press, London, 1972) according to Berry (J. Chem. Phys. 44 (1966), pp. 4550). By means of the method of the invention, it is possible, in particular, to adjust the molecular weight of the α-1,6-branched α-1,4-glucans produced by said method to a range of 1000 to 3000×10$_6$. Preferably, the α-1,6-branched α-1,4-glucans have a molecular weight ranging from 100,000 to 1500×10$_6$, more preferably from 100,000 to 1000×10$_6$, even more preferably from 262,000 to 1000×10$_6$ and most preferably from 262,000 to 499×10$_6$.

Furthermore, the invention relates to α-1,6-branched α-1,4-glucans obtainable by the above-described method of the invention. Said α-1,6-branched α-1,4-glucans have a branching degree which is higher than the one that is achieved if only the activity of an amylosucrase is used and which is 25 mol % at the most.

In a preferred embodiment of the invention, these are α-1,6-branched α-1,4-glucans having a branching degree ranging from 0.05% to 20%, preferably from 0.15% to 17%, more preferably from 0.2% to 15%, even more preferably from 0.25% to 13% and most preferably from 0.3% to 12%. In another preferred embodiment of the invention, the branching degree ranges from 0.35% to 11% and, in particular, from 0.4% to 10.5%.

The α-1,6-branched α-1,4-glucans of the invention can be used in the food and non-food industries as has been described above with regard to the starch of the invention.

The plasmid pBB48, which has been produced within the present invention, was deposited with the Deutsche Sammlung von Mikroorganismen and Zellkulturen (DSMZ, German Collection of microorganisms and cell cultures) in Braunschweig, which is approved as international depository, on 25 Sep. 1998 with the accession number DSM 12425 according to the requirements of the Budapest Treaty.

Figure 1:
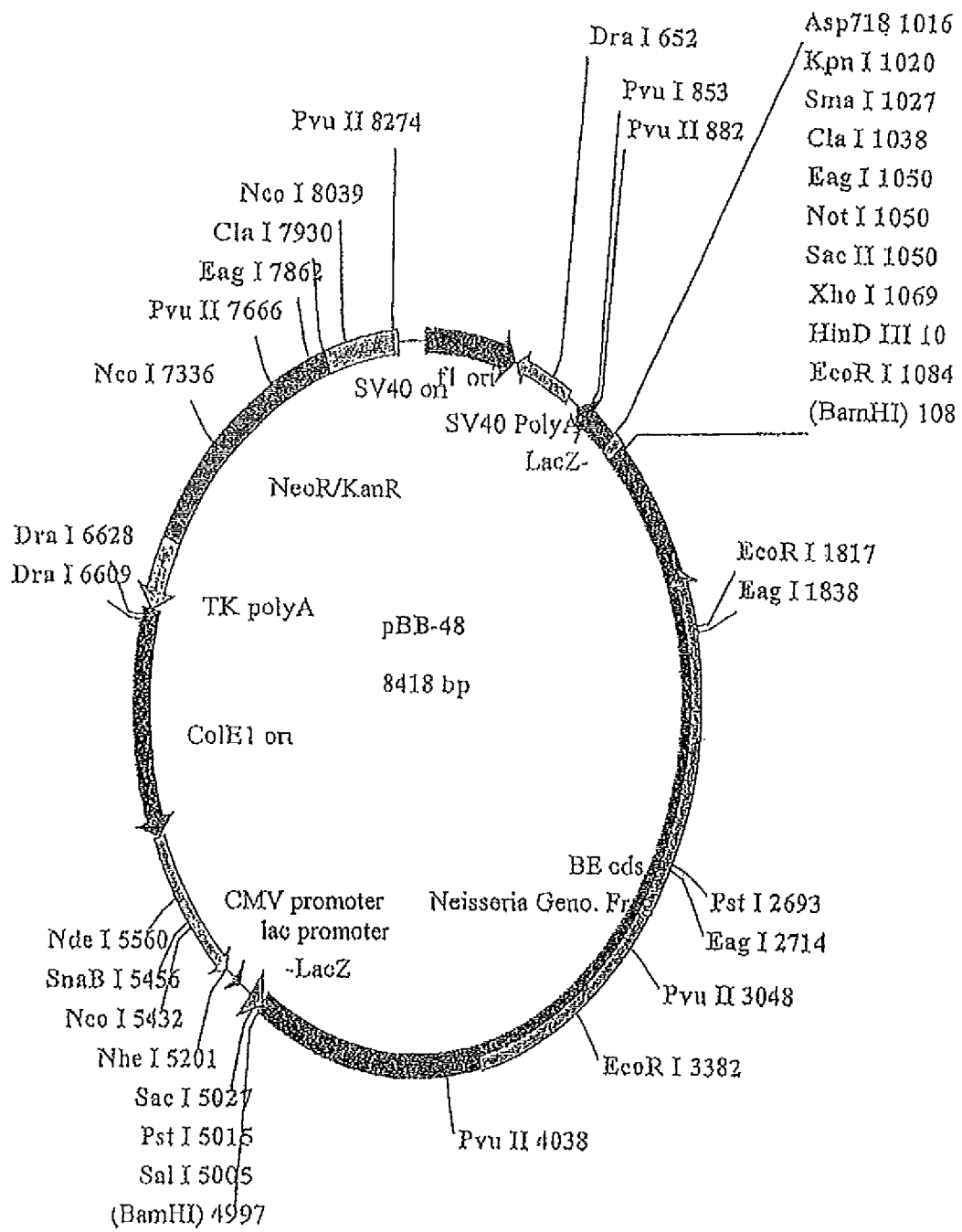
FIG. 1 schematically shows the structure of the plasmid pBB48 (DSM 12425).

FIG. 1 schematically shows the structure of the plasmid pBB48 (DSM 12425).

Figure 2:
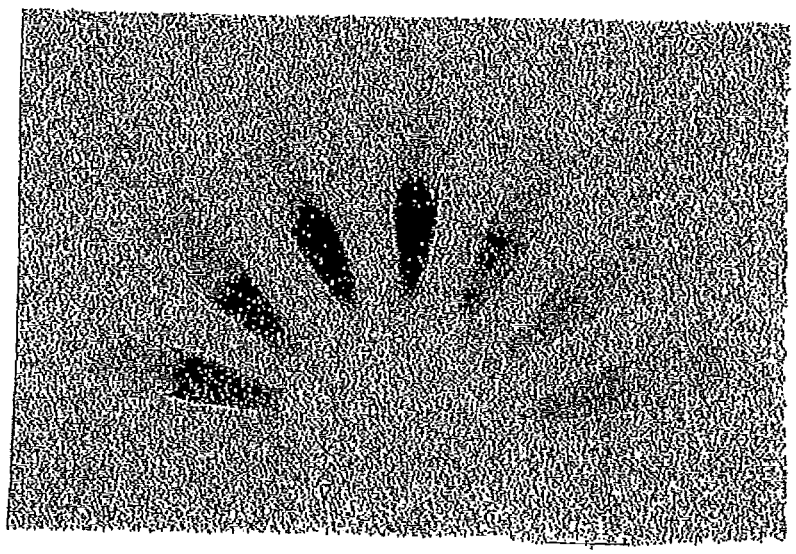
FIG. 2 shows a number of α-1,4-glucans having a varying degree of α-1,6-branchings which were produced by means of the method of the invention and which were subsequently dyed with Lugol's solution.

FIG. 2 shows a number of α-1,4-glucans having a varying degree of α-1,6-branchings which were produced by means of the method of the invention and which were subsequently dyed with Lugol's solution.

From left to right: amylosucrase (left), amylosucrase+decreasing amounts of branching enzyme activity. The maximum absorption of the corresponding samples were: 615 nm, 483 nm, 500 nm, 526 nm, 534 nm, 560 nm, 577 nm.

FIG. 3 shows a HPLC chromatograph of a highly branched process product (A) which has been debranched with isoamylase and a rat liver glycogen sample (B) which has been debranched with isoamylase.

FIG. 4 shows the scheme of the methylation analysis.

FIG. 5 shows a diagram of the results of the analysis of sample 7 described in Examples 9 and 10 after one and after two methylation steps. The values for the 2,3,6-methylation are 96.12% and 96.36%, respectively.

FIG. 6 shows a graphic illustration of the shares in terminal ("2346 Me") and 6-linked ("23 Me") glucose units of the glucan samples examined.

FIGS. 7 and 8 show gas chromatographs of the samples 3 and 7 described in the Examples.

FIG. 9 schematically shows the plasmid pBE-fnr-Km.

FIG. 10 shows an activity gel for the branching enzyme.

FIG. 11 shows the schematic illustration of an RVA profile.

FIG. 12 shows the distribution of granule size of the lines 143-13A and 143-59A compared to the wild type.

FIG. 13 shows the microscopic magnification of the starch granules of the lines 143-13A, 143-34A and 143-59A in comparison with the starch granules of wild type plants (light microscope by Leitz, Germany).

FIG. 14 shows the gel texture of the starches of different transgenic lines compared to starches from wild type plants. The texture was determined by means of a texture analyzer.

FIG. 15 shows the RVA profile of the starches of the lines 143-11A, 143-13A, 143-59A compared to the wild type.

FIGS. 16 to 18 show the results of HPLC chromatographies which represent the pattern of the distribution of the side-chains of the lines 143-WT (=wild type), 143-13A and 143-59A.

FIG. 19 shows the elution gradient that was used for the chromatographies depicted in FIGS. 16 to 18.

FIG. 20 shows the percentage deviation of side-chains having certain chain lengths of the starches analysed in FIGS. 16 to 18 from the wild type.

The following Examples illustrate the invention.

Materials:

disruption buffer: 100 mM Tris/HCl, pH 8.5; 5 mM Na$_2$EDTA; 2 mM DTT; 1 mM Pefabloc® washing buffer: 50 mM Tris/HCl, pH 8.5; 5 mM Na$_2$EDTA; 10% glycerol

HIC buffer: 50 mM potassium phosphate buffer, pH 7.0; 5 mM EDTA; 2 mM DTT; 10% glycerol oyster glycogen type II from oyster (Sigma G8751)

Methods:

Starch Analysis (a) Determination of the Amylose/Amylopectin Ratio

Starch was isolated from potato plants according to standard methods and the ratio of amylose to amylopectin was determined according to the method described by Hovenkamp-Hermelink et al. (Potato Research 31 (1988), 241-246).

(b) Determination of the Phosphate Content

In starch, the positions C2, C3 and C6 of the glucose units may be phosphorylated.

For determining the content of phosphate groups at the C6 position, 100 mg starch was hydrolysed in 1 ml 0.7 M HCl for 4 hours at 95° C. (Nielsen et al., Plant Physiol. 105 (1994), 11-117). After neutralising with 0.7 M KOH, 50 ml of the hydrolysate were subjected to an optical-enzymatic test for determining the glucose-6-phosphate. At 334 nm, the change in the absorption of the test mixture (100 mM imidazole/HCl; 10 mM MgCl$_2$; 0.4 mM NAD; 2 units glucose-6-phosphate-dehydrogenase from *Leuconostoc mesenteroides*; 30° C.) was determined.

The overall content of phosphate was determined according to the method by Ames (Methods in Enzymology VIII (1966), 115-118).

Approximately 50 mg starch are added to 30 μl of an ethanolic magnesium nitrate solution and ashed for 3 hours at 500° C. in a muffle furnace. 300 μl 0.5 M hydrochloric acid were added to the residue and incubated for 30 min at 60° C. Then, an aliquot is filled up to 300 μl 0.5 M hydrochloric acid, added to a mixture of 100 μl of 10% ascorbic acid and 600 μl of 0.42% ammonium molybdate in 2 M sulphuric acid and incubated for 20 min at 45° C.

Then, a photometric determination at 820 nm is carried out with a calibration curve using phosphate standards.

(c) Determination of the Gel Texture (Texture Analyzer)

2 g starch (TS) are pasted in 25 ml $H_2O$ (cf. RVA) and subsequently sealed airtight and stored at 25° C. for 24 hours. The samples are fixed under the probe (round stamp) of a texture analyzer TA-XT2 by Stable Micro Systems and the gel texture is determined with regard to the following parameters:

| | |
|---|---|
| test speed | 0.5 mm/s |
| penetration depth | 7 mm |
| contact area | 113 mm2 |
| pressure | 2 g |

(d) Viscosity Profile 2 g starch (TS) are added to 25 ml $H_2O$ and put in a Rapid Visco Analyzer (Newport Scientific Pty Ltd., Investment Support Group, Warriewod NSW 2102, Australia) for analysis. The device was operated according to the manufacturer's instructions. For determining the viscosity of the aqueous solution of the starch, first of all, the starch suspension is heated from 50° C. to 95° C. at a speed of 12° C. per minute. Then, the temperature is maintained for 2.5 minutes at 95° C. Subsequently, the solution is cooled down from 95° C. to 50° C. at a speed of 12° C. per minute. The viscosity is determined during the whole time.

The pastification temperature is determined by means of the slope of the viscosity graph depending on the time. If the slope of the graph is higher than 1.2 (this value is set by the user), the computer program identifies the temperature measured in this moment as pastification temperature.

(e) Determination of Glucose, Fructose and Sucrose

The content of glucose, fructose and sucrose is determined according to the method described by Stitt et al. (Methods in Enzymology 174 (1989), 518-552).

(f) Analysis of the Distribution of the Side-Chains of the Amylopectin

The distribution of the side-chains and the preparation are determined as described in Lloyd et al. (Biochem. J. 338 (1999), 515-521). It is pointed to the fact that, using said method, only the amylopectin is debranched and that the amylose is separated from the amylopectin before debranching by means of thymol precipitation. The following conditions for the elution are selected (simplified illustration, the exact elution profile is shown in FIG. 19):

| time min | 0.15M NaOH % | 1M NaAc in 0.15M NaOH % |
|---|---|---|
| 0 | 100 | 0 |
| 5 | 100 | 0 |
| 20 | 85 | 15 |
| 35 | 70 | 30 |
| 45 | 68 | 32 |
| 60 | 0 | 100 |
| 70 | 0 | 100 |
| 72 | 100 | 0 |
| 80 | 100 | 0 |

(g) Determination of the Granule Size

The size of the granules was determined with a photosedimentometer of the type "Lumosed" by Retsch GmbH, Germany.

The distribution of the granule size was determined in an aqueous solution and was carried out according to the manufacturer's indications as well as on the basis of the literature, e.g. H. Pitsch, Korngrößenbestimmung; LABO-1988/3 Fachzeitschrift für Labortechnik, Darmstadt.

(h) Determination of the Water-Binding Capacity

For determining the water-binding capacity, the residue was weighed after separating the soluble parts of the starch swelled at 70° C. by means of centrifugation. The water-binding capacity (WBV) of the starch was determined with reference to the initial weight that was corrected by the soluble mass.

$WBV$ (g/g)=(residue−(initial weight−soluble proportion))/(initial weight−soluble proportion).

EXAMPLE 1

Isolation of a Genomic DNA Sequence Encoding a Branching Enzyme from *Neisseria denitrificans*

For isolating the branching enzyme from *Neisseria denitrificans*, first of all, a genomic library was established. For this purpose, cells of *Neisseria denitrificans* of the strain deposited as ATCC 14686 at the ATCC were cultivated on Columbia blood agar plates and subsequently harvested. The genomic DNA was isolated and purified according to the method by Ausubel et al. (in: Current Protocols in Molecular Biology (1987); J. Wiley & Sons, NY). After a partial restriction digestion with the restriction endonuclease Sau3A, a ligation with BamHI-cleaved phage vector DNA (lambdaZA-PExpress by Stratagene) was carried out. After the in-vivo excision of the phage library, the plasmids obtained were transformed into the *E. coli* mutant (PGM-) (Adhya and Schwartz, J. Bacteriol. 108 (1971), 621-626). When growing on maltose, said mutant forms linear polysaccharides which turn blue after colouring with iodine. 60,000 transformants were plated onto YT agar plates with IPTG (1 mM), kanamycin (12.5 mg/l) and maltose (1%) and after incubation for 16 hours at 37° C., they were vaporized with iodine. 60 bacteria colonies which had a red, brown or yellow colour after vaporization with iodine were sleeted and plasmid DNA was isolated therefrom (Birnboim-Doly, Nucleic Acid Res. 7, 1513-1523). The isolated plasmids were then used for retransformation of the same *E. coli*-(PGM)-mutant (Adhya and Schwartz, J. Bacteriol. 108 (1971), 621-626). After repeated plating and vaporization with iodine, the clones could be reduced from 60 isolates to 4 isolates. A restriction analysis was carried out with these four plasmids showing an EcoRI fragment (1.6 kb) which had the same size in all four plasmids (FIG. 1).

EXAMPLE 2

Sequence Analysis of the Genomic Fragment of the Plasmid pBB48

The 1.6 kb EcoRI fragment was isolated (Geneclean, Bio101) from a clone obtained according to Example 1 (pBB48) which had an approx. 3.9 kb insert in the vector pBK-CMV (Stratagene). For DNA sequencing, the fragment was cloned into the vector pBluescript which had been cleaved with EcoRI. The plasmid obtained in this way was sequenced. Then, the entire DNA sequence encoding the branching enzyme as well as the sequence of flanking regions was determined by means of the starting plasmid pBB48 (SEQ ID NO. 1). The plasmid pBB48 is shown in FIG. 1. The plasmid is deposited under DSM 12425.

EXAMPLE 3

Expression of the Branching Enzyme in Recombinant *E. coli* Cells

In general, an endogenous branching enzyme (glgB) is expressed in the *E. coli* laboratory strains. For this reason, the G6MD2 mutant of *E. coli* was used for detecting the branching enzyme activity. The strain *E. coli* Hfr G6MD2 (*E. coli* Genetic Stock Center, Yale University, CGSC#5080) has an extended deletion in the region of the glucan synthesis genes (glgA, glgB, glgC). For detecting the branching enzyme activity, said mutant was transformed with the plasmid pBB48 and a crude extract was prepared of the propagated cells. The proteins of said crude extract were separated electrophoretically in a polyacrylamide gel and then incubated with and without rabbit phosphorylase B (100 mM sodium citrate, pH 7.0; AMP, glucose-1-phosphate) for determining the branching enzyme activity. Violet bands only appeared in the gel stimulated with phosphorylase, which indicated a strong branching enzyme activity.

EXAMPLE 4

In-Vitro Production of α-1,6-Branched α-1,4-Glucans with Protein Crude Extracts in a Cell-Free System For the expression of the branching enzyme, the mutant *E. coli* G6MD2 was transformed with the plasmid pBB48. The cells were cultivated with YT medium with kanamycin (12.5 mg/l) for 16 hours while shaking in an Erlenmeyer flask. After centrifugation (5000×g), the pellet obtained was washed with 100 mM Tris/HCl, pH 7.5, 1 mM DTT and, after suspension in the same buffer, the cells were disrupted with an ultrasonic probe. By another centrifugation (10,000×g), the cell debris was separated from the soluble proteins and a yellowish supernatant having a protein concentration of approx. 10 mg/ml was obtained.

From the protein crude extract obtained in that manner, different amounts (100 µl, 10 µl, 1 µl, 0.1 µl, 0.01 µl, 0.001 µl) were added to an unchanged amount of an amylosucrase in 50 ml 100 mM sodium citrate, pH 7.0 with 20% sucrose and 0.02% sodium azide. After a few hours, a first clouding was observed in the reaction mixture. After three days, the mixture was centrifuged and the products formed were washed with deionized water.

The products are soluble in DMSO and may be characterised by measuring an absorption spectrum with Lugol's solution by means of which the branching degree of the products formed may be estimated. For this purpose, the DMSO solution was strongly diluted with water and Lugol's solution was added and the spectrum from 400 nm to 700 nm was immediately measured in a Beckmann spectrophotometer (cf. FIG. 2).

Separation of the side-chains that were split off with isoamylase on a Carbopak PA100 column by means of HPLC (DIONEX; running agent: 150 mM NaOH with 1 M sodium acetate gradient) shows the same pattern for a strongly branched product as for a rat liver glycogen debranched with isoamylase (FIG. 3).

After incubation with a pullulanase, the side-chains were only split off to a very small extent.

EXAMPLE 5

Purification of the Branching Enzyme and N-Terminal Sequencing of the Protein

For isolating the branching enzyme of *Neisseria denitrificans* from recombinant Hfr G6MD2 *E. coli* cells (see above), which had been transformed with pBB48, first an overnight culture of said cells was centrifuged. The cell precipitate was then suspended in 3 volumes disruption buffer and disrupted in the French press at a pressure of approx. 16,000 to 17,000 psi. After centrifugation at 10,000 g for one hour, the supernatant was diluted to reach the 4-fold volume by adding washing buffer. Then, it was bound to DEAE cellulose DE52 using the batch-method and filled into a chromatography column which was washed with 2 to 3 column volumes of washing buffer. Subsequently, a linear 1 M NaCl gradient was applied for elution. The fractions with branching enzyme activity were combined (see Example 8), $(NH_4)_2SO_4$ was added (final concentration 20% (w/v)) and applied to a TSK butyl Toyopearl 650M column. After washing with 2 to 3 column volumes of HIC buffer, to which additionally an ammonium sulphate solution with a degree of saturation of 20% (114 g ammonium sulphate per liter) had been added before, the branching enzyme was eluted in HIC buffer using an ammonium sulphate gradient that falls linearly from 20% to 0%. Fractions with branching enzyme activity were combined. For concentrating the protein, the purification step with the combined fractions was subsequently repeated using a small TSK butyl Toyopearl 650M column (Tose Haas (Montgomery Ville, Pa.)). The purified protein was then applied to a polyacrylamide gel, blotted onto a PVDF membrane, dissolved again and sequenced N-terminally by WITA GmbH, Teltow, Germany, according to the Edman method. The sequence obtained was: MNRNXH (SEQ ID NO. 3).

EXAMPLE 6

Purification of an Amylosucrase

For producing an amylosucrase, *E. coli* cells were used which had been transformed with a DNA encoding an amylosucrase from *Neisseria polysaccharea*. The DNA has the nucleotide sequence depicted in SEQ ID NO. 4 and is derived from a genomic library of *N. polysaccharea*.

An overnight culture of said *E. coli* cells which secrete the amylosucrase from *Neisseria polysaccharea* was centrifuged off and resuspended in approx. 1/20 volume of 50 mM sodium citrate buffer (pH 6.5), 10 mM DTT (dithiothreitol), 1 mM PMSF (phenylmethylsulfonylfluoride). Then, the cells were disrupted twice with a French press at 16,000 psi. Subsequently, 1 mM $MgCl_2$ and benzonase (by Merck; 100,000 units; 250 units $µl_{-1}$) were added to the cell extract in a final concentration of 12.5 units $ml_{-1}$. After that, the mixture was incubated at 37° C. for at least 30 min while shaking gently. The extract was left to stand on ice for at least 1.5 hours. Then, it was centrifuged at 4° C. for 30 min at approx. 40,000 g until the supernatant was relatively clear.

A pre-filtration with a PVDF membrane (Millipore "Durapore", or similar) was carried out which had a pore diameter of 0.45 µm. The extract was left to stand over night at 4° C. Before carrying out the HI-(hydrophobic interaction) chromatography, solid NaCl was added to the extract and adjusted to a concentration of 2 M NaCl. Then, the mixture was again centrifuged at 4° C. for 30 min at approx. 40,000 mg. Subsequently, the remaining residues of *E. coli* were removed from the extract by filtering it with a PVDF membrane (Millipore "Durapore" of similar) which had a pore diameter of 0.22 μm. The filtered extract was separated on a butylsepharose-4B column (Pharmacia) (volume of the column: 93 ml, length: 17.5 cm). Approx. 50 ml of the extract having an amylose activity of 1 to 5 units $\mu l_{-1}$ were applied to the column. Then, non-binding proteins were washed off the column with 150 ml buffer B (buffer B: 50 mM sodium citrate, pH 6.5, 2 M NaCl). Finally, the amylosucrase was eluted by means of a falling linear NaCl gradient (from 2 M to 0 M NaCl in 50 mM sodium citrate in a volume of 433 ml at an influx rate of 1.5 ml $min_{-1}$) which had been generated by means of an automatic pumping system (FPLC, Pharmacia). The elution of the amylosucrase occurred between 0.7 M and 0.1 M NaCl. The fractions were collected, desalted on a PD10 sephadex column (Pharmacia), stabilised with 8.7% glycerol, examined for amylose sucrose activity and finally deep-frozen in storage buffer (8.7% glycerol, 50 mM citrate).

EXAMPLE 7

Determination of the Amylosucrase Activity

The amylosucrase activity was determined by incubating purified protein or protein crude extract in different dilutions at 37° C. in 1 ml reaction mixtures containing 5% sucrose, 0.1% dextrin and 100 mM citrate, pH 6.5. After 0 min, 30 min, 60 min, 120 min, 180 min, 240 min, 300 min and 360 min, 10 μl each are taken from said mixture, and the enzymatic activity of the amylosucrase is stopped by immediate heating to 95° C. Then, the proportion of the fructose released by the amylosucrase is determined in a combined photometric test. 1 μl to 10 μl of the inactivated sample are put in 1 ml 50 mM imidazole buffer, pH 6.9, 2 mM $MgCl_2$, 1 mM ATP, 0.4 mM $NAD_+$ and 0.5 U/ml hexokinase. After sequential addition of glucose-6-phosphate dehydrogenase (from *Leuconostoc mesenteroides*) and phosphoglucose isomerase, the change in the absorption is measured at 340 nm. Subsequently, the amount of fructose released is calculated by means of the Lambert-Beer law.

If the value obtained is brought into relation with the time when the sample is taken, the number of units (1 U=μmol fructose/min) (per μl protein extract or μg purified protein) can be determined.

EXAMPLE 8

Determination of the Enzyme Activity of a Branching Enzyme from *Neisseria denitrificans*

The enzymatic activity of the branching enzyme was determined in accordance with a method described in the literature (Krisman et al., Analytical Biochemistry 147 (1985), 491-496; Brown and Brown, Meth. Enzymol. 8 (1966), 395-403). The method is based on the principle of reduced iodine binding-affinity of branched glucans in comparison with non-branched α-1,4-glucans.

For determining the enzymatic activity of the branching enzyme, a series of samples of various dilutions of the branching enzyme was put into a cooled micro-titre plate. Then, the reaction was started by adding 190 μl of an amylose reaction mixture (preparation see below) and incubated at 37° C. in an incubator. Exactly after 30 min, the reaction was stopped by adding 100 μl of Lugol's solution (0.5 mM) and the samples were measured in a micro-titre reading device (Molecular Devices) at 650 nm. A mixture without amylose served as control. The reference sample with the maximum extinction value which contained amylose but no branching enzyme had an $OD_{650}$ of 1.2.

In order to be able to better compare independent assays, only the sample dilution is used for the calculation which leads to a decrease of the $OD_{650}$ by 0.5 units during an incubation time of 30 min Definition of an Activity Unit (U) of the Branching Enzyme:

The amount of enzymes causing a decrease of the $OD_{650}$ by 0.5 units from 1.2 to 0.7 in 30 min in the test described is half a unit of the branching enzyme.

Preparation of the Amylose Reaction Mixture:

While stirring, 1 ml of a 0.5% amylose solution (manufacturer: Fluka; amylose from potato) w/v in DMSO are added to 10 ml sodium citrate buffer (100 mM, pH 6.5, 0.02% w/v $NaN_3$). For measuring, the clear stock solution is again diluted with sodium citrate buffer to a ratio of 1:4 to 1:8. In the test, absorption with Lugol's solution should be at 1.2 in the reference sample used (maximum).

EXAMPLE 9

Production of α-1,6-Branched α-1,4-Glucans Having Different Branching Degrees

For producing α-1,6-branched α-1,4 glucans having different branching degrees, purified amylosucrase from *Neisseria polysaccharea* (cf. Example 6) and a purified branching enzyme from *Neisseria denitrificans* (cf. Example 5) were added to a 20% sucrose solution (w/v) in a reaction volume of 10.86 ml. Depending on the test mixture, the two enzymes were used in different protein activity ratios to each other (for the determination amylosucrase see Example 7; for the determination of the branching enzyme see Example 8) (see Table 1):

amylosucrase preparation: 6.2 U/mg; 1.8 mg/ml
branching enzyme preparation: 75 U/mg; 6.9 mg/ml

TABLE 1

| no. | μl BE | μl Amsu | units BE | units Amsu | units Amsu/ units BE |
|---|---|---|---|---|---|
| 1 | 725 | 140 | 375 | 1.6 | 1/234.4 |
| 2 | 181.3 | 140 | 94 | 1.6 | 1/58.8 |
| 3 | 45.5 | 140 | 24 | 1.6 | 1/15 |
| 4 | 11.4 | 140 | 5.90 | 1.6 | 1/3.7 |
| 5 | 2.8 | 140 | 1.45 | 1.6 | 1.1/1 |
| 6 | 0.713 | 140 | 0.37 | 1.6 | 4.3/1 |
| 7 | 0.179 | 140 | 0.09263 | 1.6 | 17.3/1 |
| 8 | 0.0446 | 140 | 0.02308 | 1.6 | 69.3/1 |
| 9 | 0.0112 | 140 | 0.00580 | 1.6 | 275.9/1 |
| 10 | 0.0028 | 140 | 0.00145 | 1.6 | 1103.4/1 |
| 11 | 0 | 140 | 0 | 1.6 | — |
| 13 | glycogen | from | *Mytillus* | *edulis* | — |

BE = branching enzyme
Amsu = amylosucrase
units = for determination see Examples 7 and 8

EXAMPLE 10

Determination of the Branching Degree by Means of Methylation Analysis

The branching degree of the glucans obtained was subsequently determined by means of a methylation analysis.

1. Examinations Carried Out
   - methylation of all free OH-groups of the glucan samples, each time double determination
   - hydrolysis of the permethylated polymers followed by a reduction at C-1 and acetylation of the monomer mixture
   - gas chromatographic analysis and quantification of the reaction products The branching degree of the glucan samples was established by means of a methylation analysis (cf. FIG. 4). The free OH-groups of the polymer are labelled by conversion into methylether.

The degradation to monomers is carried out in an acid hydrolytic manner and leads to partially methylated glucose molecules which are present in pyranosidic/furanosidic form and as α- and α-glucosides. These variants are focussed by reduction with $NaBH_4$ in the corresponding partially methylated sorbite derivative. By subsequent acetylation of free OH-groups the reaction products can be examined by means of gas chromatography.

The following table shows the texture and the DMSO solubility of the glucans obtained.

TABLE 2

| sample | Texture | DMSO solubility (cold) | DMSO solubility (100° C.) |
|---|---|---|---|
| 1 | plastic foam-like colourless | (+) | + (slightly cloudy solution) |
| 2 | n.d. | n.d. | n.d. |
| 3 | plastic foam-like colourless | (+) | + (slightly cloudy solution) |
| 4 | n.d. | n.d. | n.d. |
| 5 | colourless powder | + | + |
| 6 | n.d. | n.d. | n.d. |
| 7 | colourless powder | + | + |
| 8 | n.d. | n.d. | n.d. |
| 9 | colourless powder | + | + |
| 10 | n.d. | n.d. | n.d. |
| 11 | colourless powder | + | + |
| 13 | yellowish powder | (+) | + | n.d. = not determined

2. Experimental Part a) Preparation of the DMSO Solutions

1% solutions (w/v) were prepared in DMSO. Not all of the samples were well-soluble at room temperature: 1, 3 and 13 had to be heated for 30 minutes to 110° C. Apart from the solutions 1 and 3, which were slightly cloudy, there were optically clear solutions (cf. Table 2).

b) Methylation 2 ml of the DMSO solution (i.e. 20 mg polymer) were transferred to a 50 ml-nitrogen flask, added to 5 equivalents/OH (eq/OH) of freshly prepared dimsyl solution in an N2 stream and stirred for 30 minutes. The solutions turned cloudy and viscous. The content of the flask was frozen in an ice-bath, 10 eq/OH methyliodide were added and, after thawing, the mixture was stirred for at least 2 hours. Before the second deprotonation and methylation step, surplus methyliodide was removed in the vacuum.

After removing the surplus methyliodide, processing was carried out by adding 50 ml water and after extracting 5 times with 10 ml dichloromethane each. Any traces of DMSO were removed from the organic phase by extracting 3 times with water, then the organic phase was dried with $CaCl_2$, filtered and concentrated. The products were clear, yellowish films.

By means of sample 7, it was first checked how many methylation steps are necessary for the permethylation of the hydroxyl groups. After the first methylation, half of the mixture was processed, the other half was methylated again. After both samples had been degraded, the results of the GC-analyses were compared. First, it was found that the reaction had almost been quantitatively after one methylation step (cf. FIG. 5). For identifying a possible branching at C-3, which also may only seem to be present due to submethylation at said position, a second methylation was carried out in any case.

FIG. 5 shows a diagram of the results of the analysis of sample 7 after one and after two methylation steps; the values for 2,3,6-methylation are 96.12% and 96.36%, respectively.

c) Hydrolysis 2 mg of the methylated sample were weighed-in in a 1 ml-pressure glass, 0.9 ml 2 M trifluor acetic acid were added and it was stirred for 2.5 hours at 120° C. After cooling the glass, the mixture was concentrated in an Na stream. For removing traces of acid, three times toluene was added and blown off.

TABLE 3

| | Data of the methylation | | | | | | |
|---|---|---|---|---|---|---|---|
| | sample 1 | sample 3 | sample 5 | sample 7 | sample 9 | sample 11 | sample 13 |
| method 1 | | | | | | | |
| initial weight (mg) | 21.9 | 22.7 | 21.7 | 32.5 | 23.4 | 22.6 | 23.5 |
| (mmol) | 0.135 | 0.140 | 0.134 | 0.200 | 0.144 | 0.139 | 0.145 |
| resulting weight (mg) | 30.4 | 29.2 | 28.0 | 25 [1] | 27.7 | 28.8 | 30.4 |
| (mmol) | 0.149 | 0.143 | 0.137 | 0.122 [1] | 0.136 | 0.141 | 0.149 |
| % of theory | 110 | 102 | 102 | —[1] | 94 | 101 | 103 |
| method 2 | | | | | | | |
| initial weight (mg) | 23.7 | 22.1 | 20.7 | 20.8 | 23.1 | 21.5 | 19.5 |
| (mmol) | 0.146 | 0.136 | 0.128 | 0.128 | 0.142 | 0.133 | 0.120 |

TABLE 3-continued

Data of the methylation

|  | sample 1 | sample 3 | sample 5 | sample 7 | sample 9 | sample 11 | sample 13 |
|---|---|---|---|---|---|---|---|
| resulting weight (mg) | 31.1 | 30.6 | 27.5 | 16.0 [2] | 31.4 | 29.4 | 25.5 |
| (mmol) | 0.152 | 0.150 | 0.135 | 0.078 [2] | 0.154 | 0.144 | 0.125 |
| % of theory | 104 | 110 | 105 | 61 [2] | 108 | 108 | 104 |

[1] Half of this sample was already taken and processed after the first methylation step, thus, no exact data was available.
[2] The small amount is due to an error in processing.

d) Reduction 0.5 ml of an 0.5 M ammoniacal NaBD4 solution was added to the remainder of the previous reaction step and stirred for 1 hour at 60° C. The reagent was carefully destroyed with a few drops of glacial acetic acid. The resulting borate was removed by adding five times a 15% methanolic acetic acid and subsequently blowing off as boric acid trimethylester.

e) Acetylation

50 µl pyridine and 250 µl acetic acid anhydride was added to the remainder of the previous reaction step and stirred for 2 hours at 95° C. After cooling, the reacting mixture was dripped into 10 ml saturated NaHCO₃ solution and extracted five times with dichloromethane. The reaction products in the organic phase were examined by means of gas chromatography (product, cf. FIG. 4).

f) Gas Chromatography

The examinations by means of gas chromatography were carried out using a device by Carlo Erby GC 6000 Vega Series 2 with on-column inlet and FID detector. The separations were conducted on a fused-silica capillary column called Supelco SPB5 (inner diameter 0.2 mm, length 30 m) using hydrogen as carrier gas and a pressure of 80 kPa. The following temperature programme was used: 60° C. (1 min) –25° C./min→130° C. –4° C./min→280° C.

3. Results

The gas chromatographs were analysed by identifying the peaks, integrating the peak areas and correcting the data by means of the ECR concept by Sweet et al. (Sweet et al., Carbohydr. Res. 40 (1975), 217).

The 1,6-anhydro-compounds that could be observed in samples 1 and 3 are due to the high branching degree at C-6. During hydrolysis, this leads to monomers having a free OH-group at C-6 which may further react to form these derivatives under the reaction conditions. When calculating the branching degree, these proportions have to be added to the "2,3-Me" value.

FIG. 6 is an illustration of the proportions of terminal ("2346Me") and 6-linked ("23"Me) glucose units of the glucan samples examined.

TABLE 4

Results of the analysis in mol %: the abbreviations (A, B, etc.) correspond to the ones in FIG. 1; "16AnhPy" = 1,6-anhydro-4-O-acetyl-2,3-di-O-methyl-D-glucopyranose, "16AnhFu" = 1,6 anhydro-5-O-acetyl-2,3-di-O-methyl-D-glucofuranose; "Me1" and "Me2" denote two independent methylation analyses of the respective samples.

|  | sample 1 | | | sample 3 | | |
|---|---|---|---|---|---|---|
|  | Me1 | Me2 | average value | Me1 | Me2 | average value |
| 16AnhPy | 0.37 | traces | 0.19 | traces | traces | — |
| 16AnhFu | 0.53 | 0.47 | 0.50 | traces | traces | — |
| 2346-Me (A) | 11.73 | 11.94 | 11.84 | 9.49 | 10.68 | 10.08 |
| 234-Me (B) | traces | traces | — | — | — | — |
| 236-Me (C) | 76.37 | 77.80 | 77.09 | 82.97 | 80.67 | 81.82 |
| 23-Me (D) | 9.75 | 9.16 | 9.46 | 7.54 | 8.34 | 7.94 |
| 26-Me (E) | 0.45 | 0.31 | 0.38 | traces | 0.32 | 0.16 |
| 36-Me | 0.44 | 0.31 | 0.38 | traces | traces | — |
| 2-Me | 0.20 | — | 0.10 | — | — | — |
| 3-Me | — | — | — | — | — | — |
| 6-Me | — | — | — | — | — | — |
| Un-Me | 0.20 | — | 0.10 | — | — | — |

|  | sample 5 | | | sample 7 | | |
|---|---|---|---|---|---|---|
|  | Me1 | Me2 | average value | Me1 | Me2 | average value |
| 16AnhPy | — | — | — | — | — | — |
| 16AnhFu | — | — | — | — | — | — |
| 2346-Me (A) | 2.42 | 2.51 | 2.47 | 2.60 | 2.77 | 2.69 |
| 234-Me (B) | — | — | — | — | — | — |
| 236-Me (C) | 95.54 | 96.18 | 95.86 | 96.36 | 96.89 | 96.63 |
| 23-Me (D) | 1.36 | 1.05 | 1.21 | 0.48 | 0.33 | 0.41 |
| 26-Me (E) | 0.37 | traces | 0.19 | 0.26 | traces | 0.13 |
| 36-Me | 0.30 | 0.26 | 0.28 | 0.29 | traces | 0.15 |
| 2-Me | — | — | — | — | — | — |
| 3-Me | — | — | — | — | — | — |
| 6-Me | — | — | — | — | — | — |
| Un-Me | — | — | — | — | — | — |

|  | sample 9 | | | sample 11 | | |
|---|---|---|---|---|---|---|
|  | Me1 | Me2 | average value | Me1 | Me2 | average value |
| 16AnhPy | — | — | — | — | — | — |
| 16AnhFu | — | — | — | — | — | — |
| 2346-Me (A) | 2.89 | 2.79 | 2.84 | 2.60 | 2.49 | 2.55 |
| 234-Me (B) | — | — | — | — | — | — |
| 236-Me (C) | 95.62 | 95.62 | 95.62 | 96.21 | 97.20 | 96.70 |
| 23-Me (D) | 0.67 | 0.69 | 0.68 | 0.52 | 0.31 | 0.42 |
| 26-Me (E) | 0.36 | 0.42 | 0.39 | 0.36 | traces | 0.18 |
| 36-Me | 0.47 | 0.48 | 1.47 | 0.30 | traces | 0.15 |
| 2-Me | — | — | — | — | — | — |
| 3-Me | — | — | — | — | — | — |
| 6-Me | — | — | — | — | — | — |
| Un-Me | — | — | — | — | — | — |

|  | sample 13 | | |
|---|---|---|---|
|  | Me1 | Me2 | average value |
| 16AnhPy | traces | traces | — |
| 16AnhFu | traces | traces | — |
| 2346-Me (A) | 8.91 | 7.46 | 8.19 |
| 234-Me (B) | traces | traces | — |
| 236-Me (C) | 83.71 | 85.45 | 84.58 |
| 23-Me (D) | 7.07 | 6.87 | 6.97 |
| 26-Me (E) | 0.32 | 0.22 | 0.27 |

TABLE 4-continued

Results of the analysis in mol %: the abbreviations (A, B, etc.) correspond to the ones in FIG. 1; "16AnhPy" = 1,6-anhydro-4-O-acetyl-2,3-di-O-methyl-D-glucopyranose, "16AnhFu" = 1,6 anhydro-5-O-acetyl-2,3-di-O-methyl-D-glucofuranose; "Me1" and "Me2" denote two independent methylation analyses of the respective samples.

| | | | |
|---|---|---|---|
| 36-Me | traces | traces | — |
| 2-Me | — | — | — |
| 3-Me | — | — | — |
| 6-Me | — | — | — |
| Un-Me | — | — | — |

EXAMPLE 11

Production of α-1,6-Branched α-1,4-Glucans Having Different Molecular Weights

For producing α-1,6-branched α-1,4-glucans having different molecular weights, a purified amylosucrase from *Neisseria polysaccharea* (cf. Example 6) and a purified branching enzyme from *Neisseria denitrificans* (cf. Example 5) were added to a 20% sucrose solution (w/v) in a reaction volume of 10.86 ml. Depending on the test mixture, the two enzymes were used in different protein activity ratios (for the determination of the amylosucrase activity see Example 7; for the branching enzyme see Example 8) (cf. Table 1). The molecular weights and the radius of inertness $R_g$ were determined by means of light scattering (Light Scattering from Polymer Solutions; editor: Huglin, M. B., Academic Press, London, 1972). The dried samples 1-11 were dissolved in DMSO, $H_2O$ (at a ratio of 90:10) and different dilutions (approx. 2.5 g/l to 0.25 g/l) were analysed in a device for measuring the light scattering (SOFICA, Societé française d'instruments de contrôle et d'analyses. Le Mesnil Saint-Denis, France). The data obtained in this way were [ . . . ][1] according to Berry (J. Chem. Phys. 44 (1966), 4550 et seq.).

[1] translator's note: verb missing.

TABLE 5

| sample | ratio of amylosucrase:branching enzyme | radius of inertness Rg in nm | molecular weight in g/mol |
|---|---|---|---|
| 1 | 0.05 | 104 | 282 × 10⁶ |
| 2 | 0.2 | 154 | 499 × 10⁶ |
| 3 | 0.8 | 76 | 228 × 10⁶ |
| 4 | 3.21 | 64 | 76 × 10⁶ |
| 5 | 12.84 | 63 | 20 × 10⁶ |
| 6 | 51.22 | 38 | 1.1 × 10⁵ |
| 7 | 204.03 | 277 | 472,000 |
| 8 | 818.87 | n.d. | n.d. |
| 9 | 3275.49 | 170 | 469,000 |
| 10 | 13043.48 | n.d. | n.d. |
| 11 | no branching enzyme | 143 | 262,000 |
| 13 | glycogen (sea mussels) | 14.3 | 1.59 × 10⁶ g/mol (Burchard, W.: Macromolecules 10: 919 (1977)) | n.d. = not determined

EXAMPLE 12

Construction of an Expression Cassette for Transforming Plants for the Plastidial Expression of a Branching Enzyme from *Neisseria denitrificans*

The oligonucleotides BE-5' and BE-3' (SEQ ID NO. 6 and SEQ ID NO. 7) were used for amplifying the sequence coding for the branching enzyme from *Neisseria denitrificans* by means of PCR starting from the plasmid pBB48 (deposited with the Deutsche Sammlung von Mikroorganismen and Zellkulturen (DSMZ, German Collection of microorganisms and cell cultures) in Braunschweig with the accession number DSM 12425). The resulting amplified sequences therefrom were digested with the restriction endonucleases SalI and SdaI and cloned into the plasmid pBinAR-fnr which was cleaved with SalI and SdaI. The plasmid resulting therefrom was denoted pBE-fnr-Km (FIG. 9).

Conditions for the PCR:
Buffer and Polymerase by Boehringer Mannheim (Pwo Polymerase No.: 1644947)

| | |
|---|---|
| DNA | 0.2 ng |
| 10 × buffer + MgSO₄ | 5 µl |
| dNTPs (10 mM each) | 1 µl |
| primer BE-5' | 120 nM |
| primer BE-3' | 120 nM |
| Pwo polymerase | 1.0 units |
| distilled water | ad 50 µl |

Reaction Conditions

| | | |
|---|---|---|
| step 1 | 95° C. | 2:00 min |
| step 2 | 95° C. | 0:30 min |
| step 3 | 66° C. | 0:30 min |
| step 4 | 72° C. | 2:00 min (plus 1 sec. per cycle) |
| step 5 | 72° C. | 8:00 min |

Steps 2 to 4 were repeated in 40 cycles.

The plasmid pBE-fnr-Km was used for transforming potato plants according to standard methods (see above).

EXAMPLE 13

Identification and Detection of Transgenic Potato Plants with Branching Enzyme Activity By means of Northern blot analysis, it was possible to identify from the transgenic potato plants produced according to Example 12 plants which displayed an mRNA of a branching enzyme from *Neisseria denitrificans*. For detecting the activity of the branching enzyme in the stably transformed plants, leaf material of the plants to be examined was deep-frozen in liquid nitrogen and then ground in a mortar pre-cooled with liquid nitrogen. Before the ground material thawed, extraction buffer was added (50 mM sodium citrate, pH 6.5, 4 mM DTT, 2 mM calcium chloride). Approx. 200 µl extraction buffer were added to approx. 100 mg (fresh weight) of plant material. Solid components of the suspension of ground plant material and extraction buffer were separated by means of centrifugation (10,000×g). An aliquot of the clear supernatant obtained therefrom was mixed with a quarter of the extraction volume of running buffer (40% glycerol, 250 mM Tris, pH 8.8, 0.02% bromophenol blue) and separated in polyacrylamide gel (see below) at a constant intensity of current of 20 mA per gel. (Before the protein extracts were applied, an electrophoresis of the gels was carried out for 20 min under the conditions indicated above). After the dye bromophenol blue in the running buffer had run out of the gel, the electrophoresis was stopped. Then, the gel was equilibrated five times in washing buffer (100 mM sodium citrate, pH 6.5) at room temperature at a volume that was five times the gel volume for 20 minutes each while stirring. Subsequently, the gel was incubated in incubation buffer (100 mM sodium citrate, pH 6.5, 5% sucrose, 0.625 units of purified amylosucrase from *Neisseria polysaccharea* (for purification of the enzyme and determination of the activity see above)) in an amount that is five times the amount of the gel volume at 30° C. for 16 hours. After decanting the incubation buffer and after adding Lugol's solution (diluted at a ratio of 1:5), the glucan which is formed by the amylosucrase in combination with the branching enzyme becomes visible as bluish-brown band (FIG. 10). The entire remaining polyacrylamide gel turns blue due to the amylosucrase activity in the incubation buffer.

Composition of the Polyacrylamide Gel:

a) Separation Gel
   375 mM Tris, pH 8.8
   7.5% polyacrylamide (Biorad no. EC-890)
   For the Polymerization:
   1/2000 volumes TEMED
   1/100 volumes ammonium persulfate b) Collection Gel
   125 mM Tris, pH 6.8
   4% polyacrylamide (Biorad no. EC-890)
   For the Polymerization:
   1/2000 volumes TEMED
   1/100 volumes ammonium persulfate c) Electrophoresis Buffer
   375 mM Tris, pH 8.8
   200 mM glycine

EXAMPLE 14

Analysis of the Starch of Plants Having an Increased Branching Enzyme Activity

According to standard techniques, starch was isolated from transgenic potato plants which had been produced according to Examples 12 and 13 and examined with regard to its physical and chemical properties. It was found that the starch formed by the transgenic potato plants differs from starch synthesized in wild type plants, for example in its phosphate content and in the viscosity and pastification properties determined by means of RVA. The results of the physico-chemical characterisation of the modified starches based on the above-described analysis techniques are shown in the following table.

| no. | genotype | phosphate in C6 (%) | amylose content (%) | RVA max. (%) | RVA min. (%) | RVA fin. (%) | RVA set. (%) | RVA T (%) | gel texture (%) |
|---|---|---|---|---|---|---|---|---|---|
| 1 | Desiree (wild type) | 100 | 22.0 | 100 | 100 | 100 | 100 | 100 | 100 |
| 2 | 143-13A | 36 | 20.9 | 50 | 83 | 82 | 79 | 79 | 162 |
| 3 | 143-11A | — | 22.5 | 92 | 90 | 88 | 80 | 99.5 | — |
| 4 | 143-59A | 22 | 20.9 | 36 | 69 | 78 | 114 | 99 | 225 | legend:
143-13A, 143-11A, 143-59A = transgenic potato plants which over-express the branching enzyme from *Neisseria denitrificans*.
RVA = Rapid Visco Analyzer.
max = maximum viscosity = peak viscosity
min = minimum viscosity
fin. = viscosity at the end of the measurement
set. = setback = difference between min. and fin.
T = pastification temperature
Except for the amylose content, the percentage values refer to the wild type (=100%).

The results of the RVA analysis, the analysis of the distribution of the size of the starch granules and the gel texture are also shown in FIGS. 11 to 15.

Furthermore, FIGS. 16 to 18 show the results of the HPLC chromatographies which illustrate the pattern of the distribution of the side-chains of the lines 143-WT (=wild type), 143-13A and 143-59A. FIG. 19 shows the elution gradient used in connection with the HPLC analysis. In FIG. 20, the percentage deviation of side-chains having a certain chain length from the wild type is shown.

The following two tables explain how the proportions of side-chains were calculated.

TABLE 7

| | 143-59A (measurement 1) | | 143-59A (measurement 2) | | |
|---|---|---|---|---|---|
| name of the peak | peak area A 2 | proportion of the sum [%] B 2 | peak area C 2 | proportion of the sum [%] D 2 | average value of the area proportions E 2 |
| DP 6 | 577122 | 4.5 | 690167 | 5.08 | 4.79 |
| DP 7 | 504371 | 3.93 | 544770 | 4.01 | 3.97 |
| DP 8 | 341520 | 2.66 | 377170 | 2.77 | 2.72 |
| DP 9 | 387706 | 3.02 | 462686 | 3.40 | 3.21 |
| DP 10 | 511664 | 3.99 | 602911 | 4.43 | 4.21 |
| DP 11 | 684394 | 5.34 | 776228 | 5.71 | 5.52 |
| DP 12 | 884346 | 6.90 | 976001 | 7.18 | 7.04 |
| DP 13 | 1038389 | 8.10 | 1138027 | 8.37 | 8.23 |
| DP 14 | 1080589 | 8.43 | 1175544 | 8.65 | 8.54 |
| DP 15 | 1046585 | 8.16 | 1144404 | 8.42 | 8.29 |
| DP 16 | 977127 | 7.62 | 1016555 | 7.48 | 7.55 |
| DP 17 | 850092 | 6.63 | 881777 | 6.49 | 6.56 |
| DP 18 | 720854 | 5.62 | 739080 | 5.44 | 5.53 |
| DP 19 | 626277 | 4.88 | 627135 | 4.61 | 4.75 |
| DP 20 | 526159 | 4.10 | 522122 | 3.84 | 3.97 |
| DP 21 | 439356 | 3.43 | 431106 | 3.17 | 3.30 |
| DP 22 | 354956 | 2.77 | 336907 | 2.48 | 2.62 |
| DP 23 | 281320 | 2.19 | 266412 | 1.96 | 2.08 |
| DP 24 | 224165 | 1.75 | 200219 | 1.47 | 1.61 |
| DP 25 | 176641 | 1.38 | 169596 | 1.25 | 1.31 |
| DP 26 | 152651 | 1.19 | 145821 | 1.07 | 1.13 |
| DP 27 | 153046 | 1.19 | 123171 | 0.91 | 1.05 |
| DP 28 | 117125 | 0.91 | 103599 | 0.76 | 0.84 |
| DP 29 | 92294 | 0.72 | 85067 | 0.63 | 0.67 |
| DP 30 | 73885 | 0.58 | 59729 | 0.44 | 0.51 |
| | ΣA 2 | | ΣC 2 | | |
| sum | 12822634 | 100.00 | 13596204 | 100.00 | 100.00 |

The peak areas in columns A 1, A 2, C 1 and C 2 have been determined by means of the application program AI 450, version 3.31 by Dionex.

TABLE 8

| | 143-WT (measurement 1) | | 143-WT (measurement 2) | | |
|---|---|---|---|---|---|
| name of the peak | peak area A 2 | proportion of the sum [%] B 2 | peak area C 2 | proportion of the sum [%] D 2 | average value of the area proportions E 2 |
| DP 6 | 123190 | 1.75 | 160046 | 1.68 | 1.72 |
| DP 7 | 95526 | 1.36 | 137396 | 1.45 | 1.40 |
| DP 8 | 87365 | 1.24 | 126639 | 1.33 | 1.29 |
| DP 9 | 158742 | 2.26 | 210845 | 2.22 | 2.24 |
| DP 10 | 308544 | 4.39 | 382957 | 4.03 | 4.21 |
| DP 11 | 465107 | 6.61 | 581774 | 6.12 | 6.36 |
| DP 12 | 574882 | 8.17 | 721814 | 7.59 | 7.88 |
| DP 13 | 634154 | 9.01 | 796824 | 8.38 | 8.70 |
| DP 14 | 633566 | 9.01 | 798684 | 8.40 | 8.70 |
| DP 15 | 594327 | 8.45 | 766484 | 8.06 | 8.25 |
| DP 16 | 537537 | 7.64 | 699141 | 7.35 | 7.50 |
| DP 17 | 470522 | 6.69 | 609229 | 6.41 | 6.55 |
| DP 18 | 403081 | 5.73 | 539584 | 5.67 | 5.70 |

… TABLE 8-continued

| | 143-WT (measurement 1) | | 143-WT (measurement 2) | | |
|---|---|---|---|---|---|
| name of the peak | peak area A 2 | proportion of the sum [%] B 2 | peak area C 2 | proportion of the sum [%] D 2 | average value of the area proportions E 2 |
| DP 19 | 352504 | 5.01 | 486633 | 5.12 | 5.06 |
| DP 20 | 313708 | 4.46 | 432720 | 4.55 | 4.51 |
| DP 21 | 265289 | 3.77 | 385358 | 4.05 | 3.91 |
| DP 22 | 211722 | 3.01 | 323248 | 3.40 | 3.20 |
| DP 23 | 179015 | 2.54 | 274938 | 2.89 | 2.72 |
| DP 24 | 148758 | 2.11 | 227219 | 2.39 | 2.25 |
| DP 25 | 119135 | 1.69 | 197839 | 2.08 | 1.89 |
| DP 26 | 103902 | 1.48 | 177493 | 1.87 | 1.67 |
| DP 27 | 88686 | 1.26 | 147919 | 1.56 | 1.41 |
| DP 28 | 67024 | 0.95 | 131325 | 1.38 | 1.17 |
| DP 29 | 61086 | 0.87 | 104515 | 1.10 | 0.98 |
| DP 30 | 37850 | 0.54 | 87704 | 0.92 | 0.73 |
| | ΣA1 | | ΣC1 | | |
| sum | 7035222 | 100.00 | 9508328 | 100.00 | 100.00 |

The invention claimed is:

1. Starch prepared by the process that comprises extracting starch from transgenic plants or parts thereof that comprise transgenic plant cell containing a nucleic acid molecule linked to regulatory sequences guaranteeing the transcription in plant cells, wherein said nucleic acid molecule encodes a branching enzyme from a bacterium of the genus *Neisseria* selected from the group consisting of
   (a) nucleic acid molecules encoding a protein which comprises the amino acid sequence depicted in SEQ ID NO. 2;
   (b) nucleic acid molecules comprising the coding region depicted in SEQ ID NO. 1;
   (c) nucleic acid molecules encoding a protein which comprises the amino acid sequence encoded by the insert in plasmid DSM 12425;
   (d) nucleic acid molecules comprising the coding region for a branching enzyme, which is contained in the insert of the plasmid DSM 12425; and
   (e) nucleic acid molecules encoding a protein the sequence of which has, in the first 100 amino acids, a homology of at least 65% to the amino acid sequence depicted in SEQ ID NO. 2;
   wherein said starch has a phosphate content that is at last 20% reduced as compared to starch from a corresponding wild type plant.

2. The starch according to claim 1, wherein the composition of the starch is modified in such a way that it has at least one of the properties selected from the group consisting of an increased gel texture, a reduced phosphate content, a reduced peak viscosity, a reduced pastification temperature, a reduced size of starch granules and a modified distribution of side-chains when compared to the starch from corresponding wild type plant.

3. The starch according to claim 1, wherein said starch has a modified distribution of side-chains in that the proportion of side-chains with a DP of 6 to 8 is increased by at least 25% in comparison to the proportion of side-chains with the corresponding degree of polymerization of amylopectin from a corresponding wild-type plant.

4. The starch according to claim 1, wherein said protein sequence has a homology of at least 95% to the amino acid sequence depicted in SEQ ID NO. 2.

* * * * *